United States Patent
Amoako-Tuffour et al.

(10) Patent No.: US 10,172,598 B2
(45) Date of Patent: Jan. 8, 2019

(54) INGESTIBLE MEDICAL DEVICE

(71) Applicant: PROGENITY, INC., San Diego, CA (US)

(72) Inventors: Yaw Amoako-Tuffour, Montreal (CA); Mitchell Jones, Montreal (CA); Satya Prakash, Brossard (CA)

(73) Assignee: Progenity, Inc., San Diego, CA (US)

( * ) Notice: Subject to any disclaimer, the term of this patent is extended or adjusted under 35 U.S.C. 154(b) by 1113 days.

(21) Appl. No.: 14/460,893

(22) Filed: Aug. 15, 2014

(65) Prior Publication Data

US 2015/0011874 A1 Jan. 8, 2015

Related U.S. Application Data

(63) Continuation of application No. PCT/CA2013/000133, filed on Feb. 15, 2013.

(Continued)

(51) Int. Cl.
*A61B 10/04* (2006.01)
*A61B 5/07* (2006.01)
(Continued)

(52) U.S. Cl.
CPC .............. *A61B 10/04* (2013.01); *A61B 5/064* (2013.01); *A61B 5/065* (2013.01); *A61B 5/07* (2013.01); *A61B 5/073* (2013.01); *A61M 31/002* (2013.01); *A61B 5/0059* (2013.01); *A61B 5/01* (2013.01); *A61B 5/0538* (2013.01); *A61B 5/14539* (2013.01); *A61B 10/0096* (2013.01);

(Continued)

(58) Field of Classification Search
CPC ......... A61B 10/04; A61B 5/064; A61B 5/065; A61B 5/07; A61B 5/073; A61M 31/002
USPC ......................................................... 600/573
See application file for complete search history.

(56) References Cited

U.S. PATENT DOCUMENTS 3,057,344 A  10/1962 Abella et al.
3,118,439 A   1/1964 Perrenoud
(Continued)

FOREIGN PATENT DOCUMENTS

CA    2139822    7/1995
CA    2347274    4/2000
(Continued)

OTHER PUBLICATIONS

Luciano Boquete et al., "Dynamically Programmable Electronic Pill Dispenser System," J. Med. Sys., 34:357-366 (2010).
(Continued)

*Primary Examiner* — Daniel Cerioni
(74) *Attorney, Agent, or Firm* — Fish & Richardson P.C.

(57) ABSTRACT

Various embodiments are described herein for a device and method for an ingestible medical device with a rotatable element. In some described embodiments, the ingestible medical device includes a storage sub-unit with multiple chambers each having an opening for collecting or dispensing substances from the GI tract. The device further comprises a chamber enclosure with an access port. One of the chamber enclosure and the storage sub-unit are rotatable to allow for aligning the access port with a chamber opening. The ingestible medical device includes a sensor for positioning the access port of the chamber enclosure or the storage sub-unit as one of these elements rotates.

55 Claims, 38 Drawing Sheets

Related U.S. Application Data

(60) Provisional application No. 61/600,029, filed on Feb. 17, 2012.

(51) Int. Cl.

| | |
|---|---|
| *A61B 5/06* | (2006.01) |
| *A61M 31/00* | (2006.01) |
| *A61B 5/00* | (2006.01) |
| *A61B 5/01* | (2006.01) |
| *A61B 5/053* | (2006.01) |
| *A61B 5/145* | (2006.01) |
| *A61B 10/00* | (2006.01) |
| *G01D 5/14* | (2006.01) |
| *G01D 5/347* | (2006.01) |

(52) U.S. Cl.
CPC . *A61B 2010/0061* (2013.01); *A61B 2562/162* (2013.01); *A61B 2562/164* (2013.01); *G01D 5/145* (2013.01); *G01D 5/347* (2013.01)

(56) References Cited

U.S. PATENT DOCUMENTS

| | | | |
|---|---|---|---|
| 4,036,214 A | 7/1977 | Bucalo | |
| 4,172,446 A | 10/1979 | Bucalo | |
| 4,239,040 A | 12/1980 | Hosoya et al. | |
| 4,481,952 A | 11/1984 | Pawelec | |
| 5,167,626 A | 12/1992 | Casper et al. | |
| 5,316,015 A | 5/1994 | Sinaiko | |
| 5,604,531 A | 2/1997 | Iddan et al. | |
| 5,738,110 A | 4/1998 | Beal et al. | |
| 5,971,942 A | 10/1999 | Gu et al. | |
| 6,836,377 B1 | 12/2004 | Kislev et al. | |
| 6,934,093 B2 | 8/2005 | Kislev et al. | |
| 7,144,366 B2 | 12/2006 | Takizawa et al. | |
| 7,160,258 B2 | 1/2007 | Imran et al. | |
| 7,347,817 B2 | 3/2008 | Glukhovsky et al. | |
| 7,433,133 B2 | 10/2008 | Kislev et al. | |
| 7,460,896 B2 | 12/2008 | Iddan | |
| 7,553,276 B2 | 6/2009 | Iddan | |
| 7,643,865 B2 | 1/2010 | Iddan et al. | |
| 7,647,090 B1 | 1/2010 | Frisch et al. | |
| 7,662,093 B2 | 2/2010 | Gilad et al. | |
| 7,662,094 B2 | 2/2010 | Iddan | |
| 7,684,840 B2 | 3/2010 | Palti | |
| 7,763,014 B2 | 7/2010 | Houzego et al. | |
| 7,796,043 B2 | 9/2010 | Euliano et al. | |
| 7,797,033 B2 | 9/2010 | D'Andrea et al. | |
| 7,801,584 B2 | 9/2010 | Iddan et al. | |
| 7,813,789 B2 | 10/2010 | Glukhovsky | |
| 7,821,564 B2 | 10/2010 | Avron et al. | |
| 7,824,347 B2 | 11/2010 | Imran et al. | |
| 7,857,767 B2 | 12/2010 | Ferren et al. | |
| 7,938,775 B2 | 5/2011 | Rabinovitz et al. | |
| 7,946,979 B2 | 5/2011 | Gilad et al. | |
| 7,998,065 B2 | 8/2011 | Avni | |
| 8,000,784 B2 | 8/2011 | Ferren et al. | |
| 8,005,536 B2 | 8/2011 | Imran | |
| 8,206,285 B2 | 6/2012 | Blijevsky | |
| 8,216,130 B2 | 6/2012 | Glukhovsky et al. | |
| 8,213,698 B2 | 7/2012 | Wang | |
| 8,262,566 B2 | 9/2012 | Gilad et al. | |
| 8,360,976 B2 | 1/2013 | Imran | |
| 8,491,495 B1 | 7/2013 | Shuck | |
| 8,500,630 B2 | 8/2013 | Gilad et al. | |
| 8,512,219 B2 | 8/2013 | Ferren et al. | |
| 8,540,623 B2 | 9/2013 | Blijevsky | |
| 8,659,696 B2 | 2/2014 | Avron et al. | |
| 8,660,642 B2 | 2/2014 | Ferren et al. | |
| 8,915,863 B2 | 12/2014 | Shuck | |
| 8,926,526 B2 | 1/2015 | Shuck | |
| 8,956,281 B2 | 2/2015 | Wilson | |
| 2004/0162469 A1 | 8/2004 | Imran | |
| 2004/0199054 A1 | 10/2004 | Wakefield et al. | |
| 2005/0154277 A1 | 7/2005 | Tang et al. | |
| 2007/0122488 A1* | 5/2007 | Windhab | A61K 9/5073 424/490 |
| 2007/0173738 A1 | 7/2007 | Stoltz | |
| 2008/0033569 A1 | 2/2008 | Ferren et al. | |
| 2008/0051633 A1 | 2/2008 | Blijevsky | |
| 2008/0114224 A1* | 5/2008 | Bandy | A61B 1/00016 600/302 |
| 2008/0194912 A1* | 8/2008 | Trovato | A61B 1/00055 600/118 |
| 2009/0124872 A1 | 5/2009 | Uchiyama et al. | |
| 2009/0275923 A1 | 11/2009 | Shimizu et al. | |
| 2010/0049012 A1* | 2/2010 | Dijksman | A61B 1/041 600/302 |
| 2010/0063486 A1 | 3/2010 | Dijksman et al. | |
| 2010/0303200 A1 | 12/2010 | Kimchy et al. | |
| 2010/0324381 A1 | 12/2010 | Glukhovsky et al. | |
| 2011/0092959 A1 | 4/2011 | Zou et al. | |
| 2011/0106063 A1 | 5/2011 | Dijksman et al. | |
| 2011/0156799 A1* | 6/2011 | Zanardi | G01K 3/005 327/512 |
| 2011/0275880 A1 | 11/2011 | Ferren et al. | |

FOREIGN PATENT DOCUMENTS

| | | |
|---|---|---|
| CA | 2390153 | 6/2001 |
| CA | 2451807 | 1/2003 |
| CA | 2616010 | 2/2007 |
| DE | 19801573 | 7/1999 |
| EP | 0662304 | 1/1996 |
| EP | 1530950 | 5/2005 |
| EP | 1861007 | 7/2006 |
| EP | 1954197 | 5/2007 |
| EP | 1868487 B1 | 12/2007 |
| EP | 2 117 104 | 11/2009 |
| GB | 993734 | 6/1965 |
| JP | 53049880 | 5/1978 |
| SE | 101738 | 6/1941 |
| WO | 7900811 | 10/1979 |
| WO | 2002102243 | 12/2002 |
| WO | 200414227 | 2/2004 |
| WO | 200459568 | 7/2004 |
| WO | 200464636 | 8/2004 |
| WO | 200546485 | 5/2005 |
| WO | 2006077530 A2 | 7/2006 |
| WO | 2006103684 A2 | 10/2006 |
| WO | 2007013952 A2 | 2/2007 |
| WO | 2007045859 | 4/2007 |
| WO | 2007061305 A2 | 5/2007 |
| WO | 2009154707 A2 | 12/2009 |

OTHER PUBLICATIONS

International Search Report dated Jun. 12, 2013, International Application No. PCT/CA2013/000133.
Written Opinion dated Jun. 10, 2013, International Application No. PCT/CA2013/000133.
International Preliminary Report on Patentability dated Aug. 19, 2014, International Application No. PCT/CA2013/000133.
Ingestible Medical Devices, NRC CNRC, dated Feb. 9, 2009.
11 RU 86FG 3MR1—Enteric Film Coating for Bile Intake Capsules Technology Collaboration Request, Enterprise Europe Network in Yorkshire 2011, Apr. 10, 2011.
Quirini et al., "Design of a Pill-Sized 12-legged Endoscopic Capsule Robot", 2007 IEEE International Conference on Robotics and Automation, Roma, Italy, Apr. 10-14, 2007, 1856-1862.
Tan et al., "Design of Accelerometer-Based Inertial Navigation Systems", IEEE Transactions on Instrumentation and Measurement, vol. 54, No. 6, Dec. 2005, 2520-2530.
"Redefining Capsule Endoscopy" Brochure, Olympus, Created Oct. 25, 2007.
Tortora et al., "Propeller-based wireless device for active capsular endoscopy in the gastric district", Informa Healthcare, Minimally Invasive Therapy, 2009; 18:280-290.
Toennies et al., "Swallowable medical devices for diagnosis and surgery: the state of the art", Proc. IMechE vol. 224, Part C: J. Mechanical Engineering Science, 1397-1414.

(56) References Cited

OTHER PUBLICATIONS

Susilo et al., "A Miniaturized Wireless Control Platform for Robotic Capsular Endoscopy Using Advanced Pseudokernel Approach", Sensors and Actuators A 156 (2009), 49-58.
Valdastri et al., "Transmission Power Requirements for Novel ZigBee Implants in the Gastrointestinal Tract", IEEE Transactions on Biomedical Engineering, vol. 55, No. 6, Jun. 2008, 1705-1710.
SmartPill Product Overview, The SmartPill Corporation, 2010.
SmartPill: The data you need to evaluate motility disorders, The SmartPill Corporation, 2009.
SmartPill pH.p. Capsule Operational Specifications, The SmartPill Corporation, 2003.
Extended European Search Report in corresponding EP Application No. 337862EP/CMH, dated Oct. 5, 2015, pp. 1-9.

* cited by examiner

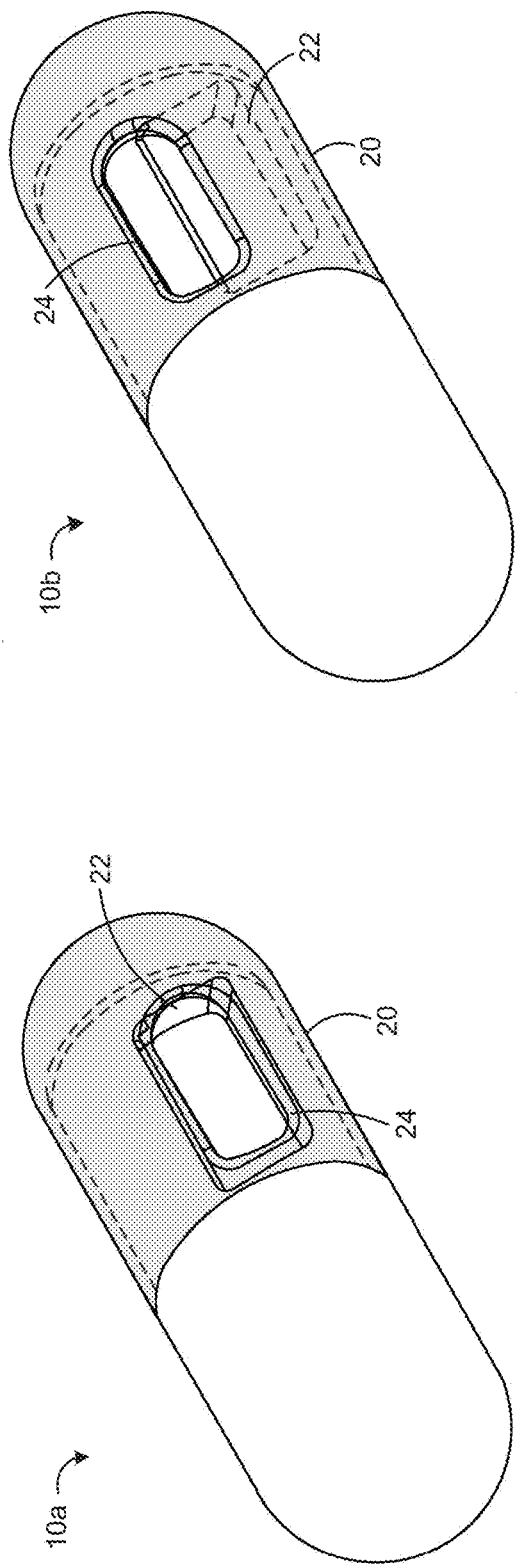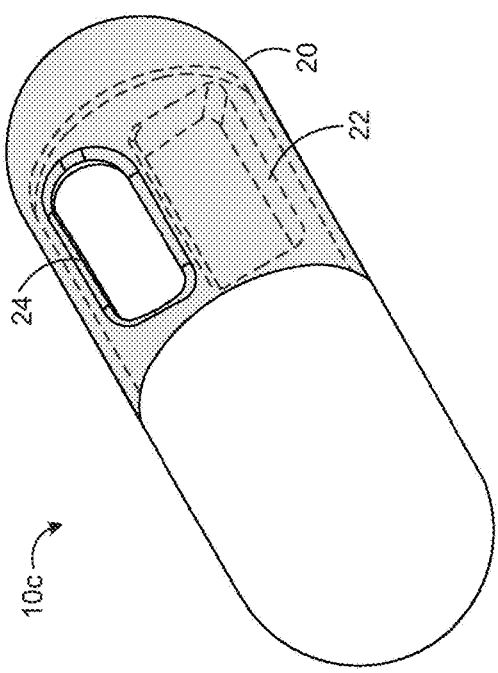

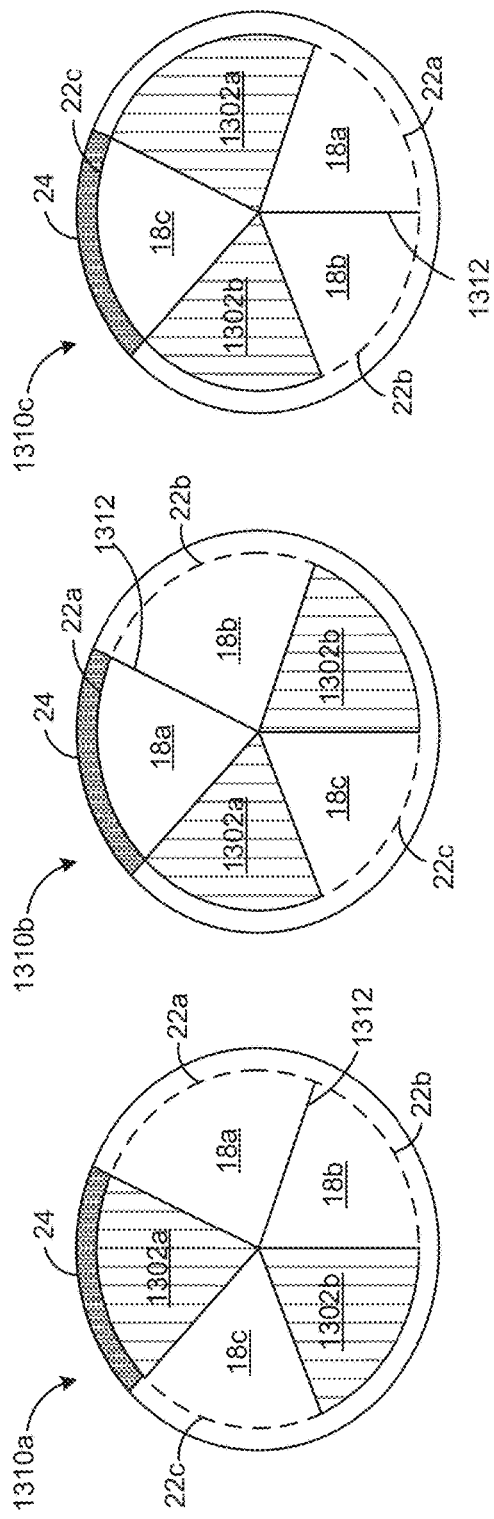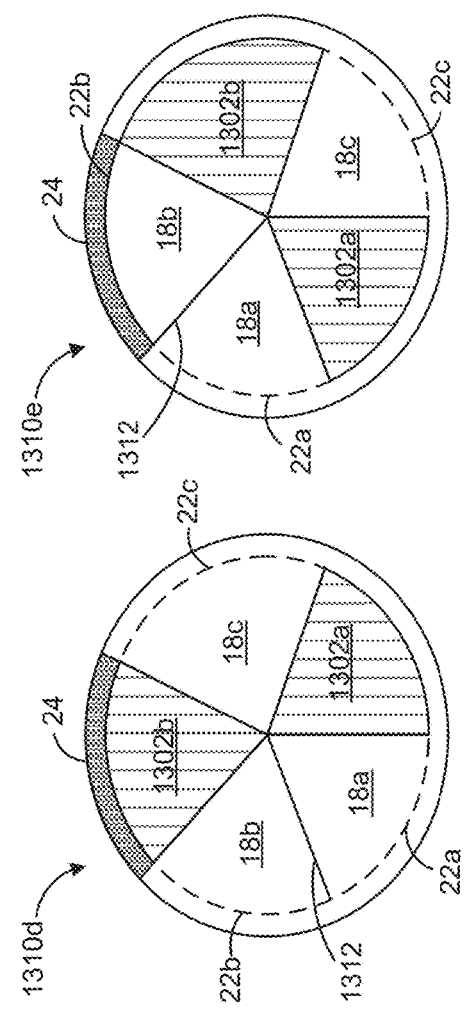
FIG. 13A FIG. 13B FIG. 13C FIG. 13D FIG. 13E

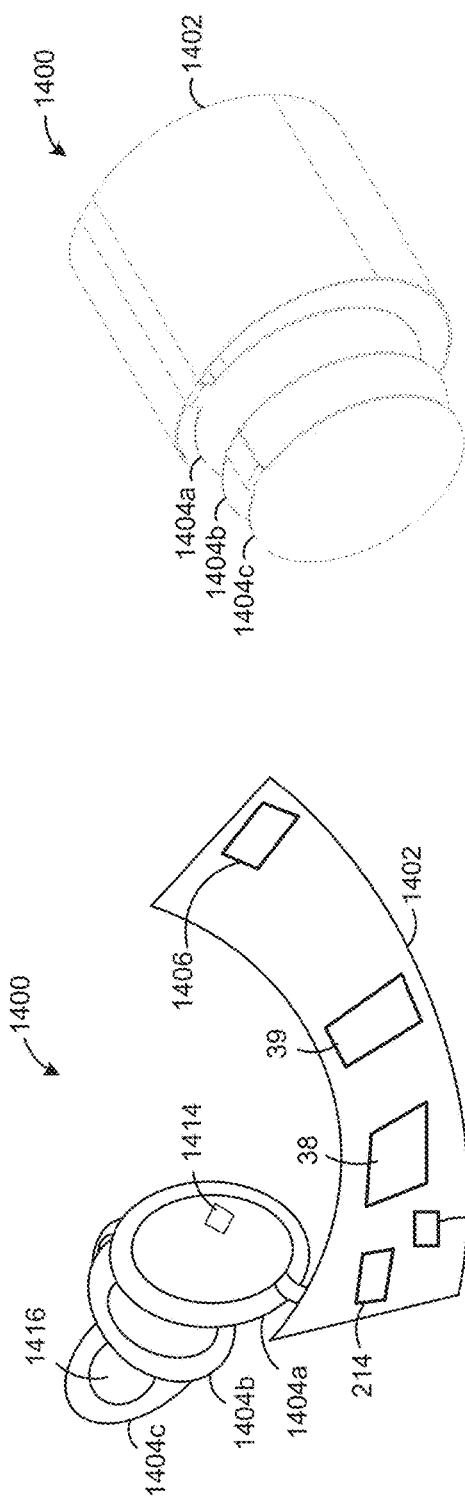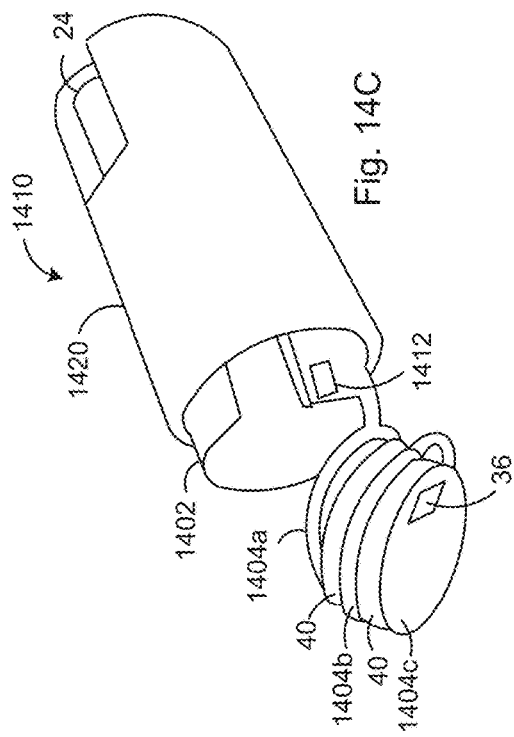

INGESTIBLE MEDICAL DEVICE

CROSS-REFERENCE TO RELATED APPLICATIONS

This application is a continuation of PCT Patent Application No. PCT/CA2013/000133, filed Feb. 15, 2013, which claims priority from U.S. Provisional Patent Application No. 61/600,029, filed Feb. 17, 2012. The entire contents of PCT Patent Application No. PCT/CA2013/000133 and U.S. Provisional Patent Application No. 61/600,029 are hereby incorporated by reference.

FIELD

The various embodiments described herein generally relate to an ingestible medical device, and methods thereof, for collecting and/or releasing a substance.

BACKGROUND

The gastrointestinal (GI) tract generally contains a wealth of information regarding an individual's body. For example, contents in the GI tract may provide information regarding the individual's metabolism. An analysis of the contents of the GI tract may also provide information for identifying relationships between the GI content composition (e.g., relationship between bacterial and biochemical contents) and certain diseases.

Present methods and devices for analyzing the gastrointestinal (GI) tract are limited in terms of the type and amount of data that can be retrieved from the GI tract. For example, conventional devices and methods are generally directed to provide basic information about the GI tract, such as environment conditions (e.g., acidity level, electrical impedance, pressure, temperature, etc.) and/or whether a particular substance (e.g., blood) is present or not. Other relevant information regarding the GI tract (e.g., temporal and spatial information about the bacterial and chemical populations and interactions) is generally unavailable with present technology. However, these conventional devices are generally triggered to sample or release substances when the devices come into contact with particular GI substances, which may limit their effectiveness.

SUMMARY OF VARIOUS EMBODIMENTS

In one aspect, in at least one embodiment described herein, there is provided an ingestible medical device for performing at least one of collecting samples and distributing substances within the GI tract of a body. The medical device comprises a storage sub-unit comprising at least one chamber having a chamber opening, the at least one chamber providing a space for a collected sample to be stored or from which a substance is distributed; a chamber enclosure enclosing the storage sub-unit, the chamber enclosure having an access port to expose or cover the chamber opening of the at least one chamber for sample distribution and sample collection respectively; a position encoder sub-unit configured to generate a positioning signal for determining a distance of the access port relative to the chamber opening of the at least one chamber; a motor coupled to the rotatable element for rotating the rotatable element to align the access port with the chamber opening of the at least one chamber to obtain the collected sample or release the substance to be distributed; and a main microcontroller coupled to the motor and the position encoder unit, the main microcontroller being configured to rotate the motor based on the positioning signal. One of the storage sub-unit and the chamber enclosure is rotatable.

In another aspect, in at least one embodiment described herein, there is provided a method for performing at least one of collecting samples and distributing substances within the GI tract of a body using an ingestible medical device. The method comprises providing a storage sub-unit comprising at least one chamber having a chamber opening to provide a space for a collected sample to be stored or from which a substance is distributed; providing a chamber enclosure enclosing the storage sub-unit, the chamber enclosure having an access port to expose or cover the chamber opening of the at least one chamber for sample distribution and sample collection respectively; generating a positioning signal for determining a distance of the access port relative to the chamber opening of the at least one chamber using a position encoder sub-unit; and rotating the rotatable element using a motor based on the positioning signal to align the access port with the chamber opening of the at least one chamber to obtain the collected sample or release the substance to be distributed. One of the storage sub-unit and the chamber enclosure is rotatable.

In another aspect, in at least one embodiment described herein, there is provided a system for performing at least one of collecting samples and distributing substances within the GI tract of a body. The system comprises an ingestible medical device as described herein and a base station. The base station comprises a chamber engagement dock for coupling with the storage sub-unit for processing at least one of the chambers of the storage sub-unit, wherein the chamber engagement dock comprises at least one needle engagement element for engaging with the at least one chamber; a charging dock comprising at least one electrical contact for engaging with a corresponding charging connector in the ingestible medical device for charging the ingestible medical device; a programming component for programming the ingestible medical device; a Universal Serial Bus (USB) connection port for receiving operating instructions and operating parameters; and a fluid connection port 908 comprising at least one tube coupled to the at least one needle engage element for allowing passage of substances therebetween.

In another aspect, in at least one embodiment described herein, there is provided a computer readable medium comprising a plurality of instructions executable on a microprocessor of a device for adapting the device to implement a method of performing at least one of collecting samples and distributing substances within the GI tract of a body using an ingestible medical device. The method comprises positioning a chamber enclosure and a storage sub-unit relative to one another, the storage sub-unit comprising at least one chamber having a chamber opening to provide a space for a collected sample to be stored or from which a substance is distributed and the chamber enclosure encloses the storage sub-unit and has an access port to expose or cover the chamber opening of the at least one chamber for sample distribution and sample collection respectively; generating a positioning signal for determining a distance of an access port relative to the chamber opening of the at least one chamber using a position encoder sub-unit; and rotating one of the chamber enclosure and the storage sub-unit using a motor based on the positioning signal to align the access port with the chamber opening of the at least one chamber to obtain the collected sample or release the substance to be distributed, wherein one of the storage sub-unit and the chamber enclosure is a rotatable element.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and in which:

FIGS. 2A to 2C are diagrams of a chamber enclosure of the ingestible medical device in operation;

FIGS. 13A to 13E are diagrams of a storage sub-unit of the ingestible medical device in operation in one example embodiment;

FIGS. 14A and 14B are block diagrams of a flexible PCB in an example embodiment;

FIG. 14C is a block diagram of the flexible PCB of FIGS. 14A and 14B within an ingestible medical device;

DETAILED DESCRIPTION OF THE EMBODIMENTS

Figure 1:
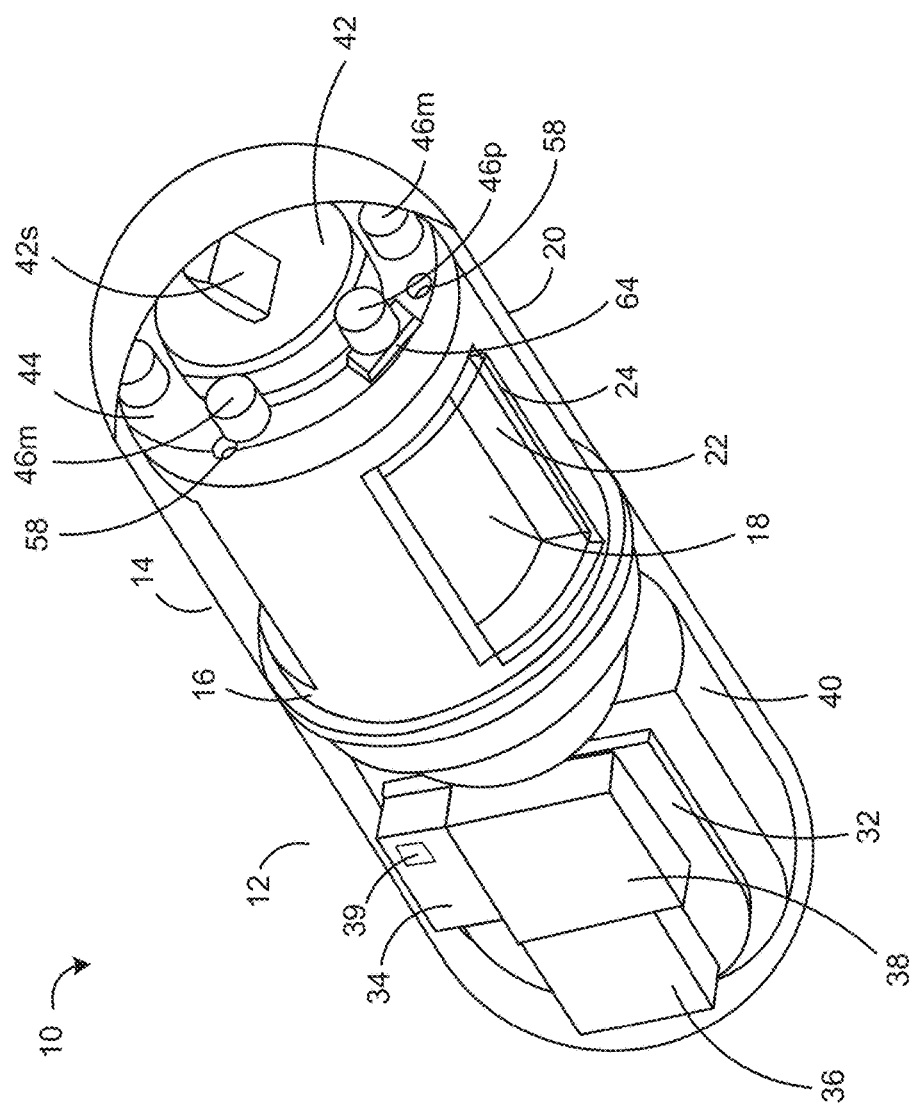
FIG. 1 is a partial view of an example embodiment of an ingestible medical device.

Various apparatuses or processes will be described below to provide an example of an embodiment of each claimed invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses or processes described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

The various embodiments described herein generally relate to an ingestible medical device for collecting and/or releasing of substances in the GI tract. In this field of art, while there have been other devices that have been constructed for these purposes, these other devices use actuation and control means that are less sophisticated and do not allow for a complicated sequence of operations to be performed such as releasing a substance from one chamber and then sampling another substance with the same chamber, dealing with obstructions that can affect the collection or dispensing of substances, performing serial collection or dispensing of multiple substances multiple times or continuously, collecting tissue samples, applying stabilizing reagents to collected substances, delivering drugs to targeted locations, dispensing of contrast agents and/or nuclear tagging agents for providing better visualization when imaging the GI tract, and/or providing a physiochemical, biological and/or topographical mapping of the GI tract, to name just a few examples. Furthermore, these other devices are generally unable to handle substances that are viscous, heterogeneous, and/or large in size.

It should be noted that the term "coupled" used herein indicates that two elements can be directly coupled to one another or coupled to one another through one or more intermediate elements. Furthermore, the term "body" typically refers to the body of a patient or a subject who receives the ingestible medical device. The patient or subject is generally a human or other animal.

Referring now to FIG. 1, shown therein is a partial view of an example embodiment of an ingestible medical device 10 in which a portion of the enclosure of the ingestible medical device 10 has been removed. The ingestible medical device 10 may be used for collecting and/or releasing substances. The ingestible medical device 10 may generally be in the shape of a capsule, like a conventional pill. Accordingly, the shape of the ingestible medical device 10 provides for easier ingestion and is also familiar to healthcare practitioners and patients.

Unlike a conventional pill, the ingestible medical device 10 is designed to withstand the chemical and mechanical environment of the GI tract (e.g., effects of muscle contractile forces and concentrated hydrochloric acid in the stomach). However, unlike other devices that are intended to stay inside a patient's body (e.g., medical implants), the ingestible medical device 10 is designed to only temporarily travel within the body. Accordingly, the regulatory rules governing the materials and manufacture of the ingestible medical device 10 may be less strict than for the devices that are intended to stay inside the body. Nevertheless, since the ingestible medical device 10 still enters the body, the material(s) used to manufacture the ingestible medical device 10 are generally selected to at least comply with the standards for biocompatibility (e.g., ISO 10993). Furthermore, components inside the ingestible medical device 10 are free of any restricted and/or toxic metals and are lead-free pursuant to the Directive 2002/95/EC, which is also known as the Restriction of Hazardous Substances (RoHS).

There is a broad range of materials that may be used for manufacturing the ingestible medical device 10. Different materials may be used for each of the different components of the ingestible medical device 10. Examples of these materials include, but are not limited to, thermoplastics, fluoropolymers, elastomers, stainless steel and glass complying with ISO 10993 and USP Class VI specifications for biocompatibility. In certain embodiments, these materials may further include liquid silicone rubber material with a hardness level of 10 to 90 as determined using a durometer (e.g., MED-4942™ manufactured by NuSil™), a soft biocompatible polymer material such as, but not limited to, polyvinyl chloride (PVC), polyethersulfone (PES), polyethylene (PE), polyurethane (PU) or polytetrafluoroethylene (PTFE), and a rigid polymer material coated with a biocompatible material that is soft or pliable (e.g., a poly(methyl methacrylate) (PMMA) material coated with silicone polymer). Use of different materials for different components may enable functionalization of certain surfaces for interaction with proteins, antibodies, and other biomarkers. For example, Teflon® may be used as a material in the ingestible medical device 10 for any movable components in order to reduce friction between these components. Other example materials may include other materials commonly used in micro-fabrication, such as polydimethylsiloxane (PDMS), borosilicate glass, and/or silicon.

Generally, an enclosure of the ingestible medical device 10 may be manufactured from a type of plastic, such as a photosensitive acrylic polymer material. The enclosure may be formed by coupling two enclosure ends together. The enclosure, in effect, protects the interior of the ingestible medical device 10 from its external environment and also protects the external environment (e.g., the GI tract) from components inside the ingestible medical device 10.

Furthermore, the ingestible medical device 10 may include one or more additional layers of protection. The additional protection may protect the patient against any adverse effects arising from any structural problems associated with the enclosure (e.g., the two enclosure ends falling apart or a fracture developing in the enclosure). For example, a power supply inside the ingestible medical device 10 may be coated with an inert and pliable material (e.g., a thin layer of silicone polymer) so that only electrical contacts on the power supply are exposed. This additional protection to the power supply may prevent chemicals inside the ingestible medical device 10 from seeping into the patient's body.

Also, a surface of the ingestible medical device 10 and surfaces of the different components in the ingestible medical device 10 may receive different treatments that vary according to an intended use of the ingestible medical device 10. For example, the surface of the ingestible medical device 10 may receive plasma activation for increasing hydrophilic behavior. In another example, for minimizing cross-contamination in the collected samples and/or substances for release, certain storage components that may come into contact with these samples and/or substances may receive hydrophilic treatment while certain other components may receive hydrophobic treatments.

The components of the ingestible medical device 10 are generally too small and complex for fabrication with conventional tools (e.g., lathe, CNC, drill-press) but are also too large for efficient construction using microfabrication techniques. Fabrication techniques that fall between the above two techniques include 3D printing (e.g., Multi-jet Modeling (MJM)), and 3D mechanical computer-aided design (CAD). Software packages by SolidWorks™ and/or Alibr™ are example CAD software that may be used to design the components of the ingestible medical device 10.

The different components of the ingestible medical device 10 may be fabricated using different conventional manufacturing techniques such as injection molding, computer numerical control (CNC) machining and by using multi-axial lathes. For example, the enclosure of the ingestible medical device 10 can be fabricated from CNC machined polycarbonate material and the storage component can be fabricated by applying a biocompatible material, such as silicone polymer, to a 3D-printed mold or cast.

Silicone polymer can provide certain advantages to the fabrication process of the ingestible medical device 10. For instance, components in the ingestible medical device 10 that are formed using the silicone polymer material can be fabricated using conventional methods, such as molding techniques. Silicone polymer material is also a pliable material. Therefore, components that are formed from silicone polymer material can accommodate a greater range of design deviations during the manufacturing stage and can also be adapted for compression fitting. For example, a component formed using silicone polymer material can be larger in size than an opening that is to receive that component. Due to the pliable nature of the silicone polymer material, that component can fit through the opening and can then expand to fill any crevice or hole within the opening. As a result, that component can act as a seal for the opening. However, it will be understood that the pliable nature of the silicone polymer material may cause a component formed using the silicone polymer material to be susceptible to external pressure. For example, a storage component formed using silicone polymer can be affected by pressure from the intestine and thus, the storage component needs to be formed with an appropriate thickness to withstand that pressure. For example, a divider between two adjacent chambers in the storage component can have a thickness of approximately 2.5 mm. The divider may taper away from the center of the ingestible medical device 10 and accordingly decrease in thickness to approximately 1.5 mm.

Referring still to FIG. 1, as illustrated therein, the structure of the ingestible medical device 10 comprises first portions and second portions 12 and 14. The first portion 12 includes control electronics, a power supply, and a communication system. The second portion 14 is generally configured to interact with the GI tract, such as, for example but not limited to, sample collection, substance delivery and environmental monitoring. The second portion 14 includes a storage sub-unit 16 with one or more chambers 18 and a chamber enclosure 20 that encloses or overlays the storage sub-unit 16. Each chamber 18 has a corresponding chamber opening 22. The chamber enclosure 20 has an access port 24. In this example embodiment, the ingestible medical device 10 comprises three chambers 18, but there can be other embodiments that have one, two or more than three chambers 18.

Referring now to FIGS. 2A to 2C, shown therein are diagrams illustrating an operational function of the ingestible medical device 10. Generally, the chamber enclosure 20 operates as a "closed-loop" revolver mechanism. The chamber enclosure 20 rotates, in a controlled manner, to align the access port 24 with each of the chamber openings 22 for collecting, at targeted locations, samples of the contents in the GI into the corresponding chamber 18, and/or for delivering substances stored in the chambers 18 to targeted locations within the body.

Generally, during collection of samples, the rotation of the chamber enclosure 20 may be described as a "closed-loop" revolver mechanism because each chamber opening 22 is exposed only once during the passage of the ingestible medical device 10 within the body in order to avoid cross-contamination of the collected samples. In other words, the chamber enclosure 20 ideally rotates only once when collecting samples during each usage of the ingestible medical device 10 so that the access port 24 aligns with each of the chamber openings 22 serially and only once. That is, during collection of samples, the access port 24 does not bypass any chamber opening 22 and also does not return to a previous chamber opening 22 during its rotation.

In some embodiments, the chamber enclosure 20 can rotate in a bidirectional motion before completing one revolution and/or perform multiple revolutions during one usage of the ingestible medical device 10 so that at least one chamber opening 22 is exposed multiple times. A chamber opening 22 may need to be exposed multiple times if its corresponding chamber stores solids or semi-solid reagents, sensors or cleaning agents for cleaning the GI tract.

As illustrated in FIG. 2A, shown therein generally is the ingestible medical device 10 in an open position 10a in which the access port 24 on the chamber enclosure 20 is aligned with a chamber opening 22. In this configuration, the ingestible medical device 10 may collect and/or release substances through the chamber opening 22. In other words, the contents of the GI tract may be forced into the exposed chamber 18 through muscular contractions (e.g., peristalsis) and/or the substance stored in the exposed chamber 18 may be released into the body through diffusion depending on the mode of operation of the ingestible medical device 10.

Thereafter, the chamber enclosure 20 may rotate to seal the chamber opening 22. As illustrated in FIG. 2B, shown therein generally is the ingestible medical device 10 with a partially open/partially closed position 10b in which the access port 24 has been rotated such that the chamber enclosure 20 partially seals the chamber opening 22.

In FIG. 2C, generally illustrated therein is the ingestible medical device 10 in a closed position 10c, in which the chamber enclosure 20 has been rotated a distance such that the access port 24 completely seals the chamber opening 22. If the chamber enclosure 20 has not rotated one revolution, the chamber enclosure 20 may continue to rotate in the same direction in order to align the access port 24 with another chamber opening 22 depending if the ingestible medical device 10 has been configured to perform another operation (i.e. sampling or distribution).

In another example embodiment, the chamber enclosure 20 may be stationary and the storage sub-unit 16 may instead rotate to align its one or more chamber openings 22 with the access port 24. Rotating the storage sub-unit 16 instead of the chamber enclosure 20 may provide greater control over the rotation motion and a more constant motion since the storage sub-unit 16 would not be subjected to a varying viscosity arising from the contents in the GI tract. This arrangement, however, may limit a volume of at least one of the chambers 18. This example embodiment is described in more details below with reference to FIGS. 10A to 10C and 11A to 11E.

In some embodiments, the chamber enclosure 20 or the storage sub-unit 16 may rotate in a predetermined sequence of bidirectional rotational motions. As described above, when the storage sub-unit 16 is configured to rotate instead of the chamber enclosure 20, the volume of at least one of the chambers 18 can be limited. In order to avoid having to limit the volume of the chambers 18, non-recess areas that may be used to separate different chambers 18 in the storage sub-unit 16 may be minimized in volume or removed. An example embodiment with such a storage sub-unit configuration is described in more detail with reference to FIGS. 20A to 20L. Also, the operation of an ingestible medical device 10 with at least two chambers 18, or two adjacent chambers, that are not separated by a non-recess area is generally described with reference to FIGS. 13A to 13E. Briefly, the ingestible medical device 10 can rotate in a first direction for aligning the access port 24 with one of the two adjacent chambers. The ingestible medical device 10 can be configured to rotate in a second direction that is opposite to the first direction in order to avoid cross contamination between samples collected into or substances released from those two adjacent chambers.

As briefly described above, the ingestible medical device 10 may generally be used to carry out different tasks. In some cases, the ingestible medical device 10 may be used for collecting usable samples from the contents of the GI tract (e.g., 100 μL sized samples) and maintaining each sample in isolation from one another until the samples are extracted.

In some embodiments, the ingestible medical device 10 may be used for releasing substances into the body in a controlled manner. In this case, prior to introducing the ingestible medical device 10 into the body, at least one of the chambers 18 in the ingestible medical device 10 may be loaded with a substance, either in a liquid or dry-powder format. The ingestible medical device 10 may be configured to perform a controlled release of one or more substances at a predetermined time depending on how many chambers 18 are provided with substances. Alternatively, or in addition thereto, the ingestible medical device 10 may be configured to perform a controlled release of the substances in the different chambers 18 at the same time. In either case, the same or different samples can be provided to different chambers 18. If different samples are provided to the different chambers 18, then the ingestible medical device 10 can be used to perform a controlled release of different drug combinations.

In some embodiments, the ingestible medical device 10 may be configured to collect samples after releasing one or more substances into the body (in a predefined sequence in the case of multiple reagents) and the ingestible medical device 10 may then collect a resulting physical sample from the body. For example, substances that may inhibit enzymatic and chemical processes may be released into the body before a sample is collected (e.g., for preventing potential degradation of the collected samples in order to obtain a "snap-shot" of the environment from which the sample was collected).

In some embodiments, the ingestible medical device 10 may also be configured to conduct in-vivo measurements. The ingestible medical device 10 is introduced into the body with some of the chambers 18 being empty and some of the chambers 18 carrying at least one reagents. At a predefined location in the body, the ingestible medical device 10 is configured to collect a sample from the GI tract and to store the sample into a chamber carrying at least one reagent. After collection, in-vivo analysis may be conducted based on how the collected sample interacts with the reagent inside the chamber 18. For example, the ingestible medical device 10 may use a biochemistry assay, such as an enzyme-linked immunosorbent assay (ELISA), for performing in-situ experiments on collected samples. Alternatively, peripherals can be included into the chambers 18 for changing the dynamics of several in-vivo analysis and measurements. The peripherals may include a light source, a receiver, a transducer, a heater, and the like. In general, the in-vivo experiments vary according to the type of information that is being sought.

Example reagents include, but are not limited to, pH adjustment reagents and buffers, acids such as HCl, bases such as NaOH, metal ion chelating agents such as EDTA for metalloprotein enzymes, competitive inhibitors of enzymes, organic and inorganic inhibitors, stabilizing chemicals (e.g., DNAase/RNAase inhibitors or DNA/RNA protect solution), enzyme inhibitors for inhibiting a progression of an enzymatic reaction (e.g., enzyme protect solutions), and the like. It will be understood that these are merely examples of what may be carried in the ingestible medical device 10 and that other substances may be used in other applications.

Referring now to FIGS. 3A to 3G, shown therein is an exploded view of the components of the ingestible medical device 10 in one example embodiment. The first portion 12 of the ingestible medical device 10 includes an end closure 30, and electronic components embedded on a main printed circuit board (PCB) 32 including a communication subsystem having communication peripherals 34 and a transceiver 36, a main microcontroller (i.e. processor) 38, a power supply 40 and other peripheral components described in further detail below. The second portion 14 of the ingestible medical device 10 generally includes a motor 42, the storage sub-unit 16, a secondary PCB 44, an encoding magnet arrangement 46 and the chamber enclosure 20. Generally, by placing the main PCB 32 and the secondary PCB 44 in distinct regions inside the ingestible medical device 10, they may be prevented from experiencing the same electrical or physical hazards. Each of these components is described in more detail below.

Each of the PCBs (e.g., 32 and 44) may be embedded with one or more electronic components that form the control infrastructure of the ingestible medical device 10. In some embodiments, rigid boards may be used as the PCBs 32 and 44. Alternatively, flexible printed circuits may be used as the PCBs 32 and 44. The flexible printed circuits may reduce the number of components required to operate the ingestible medical device 10 by enabling two PCBs to be joined together directly. These flexible printed circuits may also maximize the utilization of space within the ingestible medical device 10 by enabling easier conformation to the dimensional constraints of the ingestible medical device 10 where necessary. Increased flexibility means that there can be more twisting, bending, and shaping of the PCB or certain parts of the PCB, ultimately leading to a smaller pill.

As generally illustrated in FIGS. 14A to 14F, a flexible PCB 1400 may be used as the main PCB 32 in an ingestible medical device 1410 in an example of an alternative embodiment. Although not currently shown in FIGS. 14A to 14C, electronic components located on the flexible PCB 1400 are connected with one or more electronic signal pathways, traces, or tracks.

The flexible PCB 1400 may be fabricated using a combination of a flexible plastic material and a rigid material, such as a woven fiberglass cloth material. The resulting flexible PCB 1400 can therefore exhibit both a flexible quality and a rigid quality. The flexible quality of the flexible PCB 1400 enables the electronic components located on the flexible PCB 1400 to more easily conform to the dimensional constraints of the ingestible medical device 1410. In particular, as generally illustrated in FIG. 14C, the flexible PCB 1400 can be inserted into a chamber enclosure 1420 along with the storage sub-unit 16. At the same time, the rigid quality of the flexible PCB 1400 enables reinforcement of areas that may be susceptible to high levels of physical stress. For example, contact terminals that are used for connecting the flexible PCB 1400 to the power supply 40 and/or the motor 42 may require added reinforcement.

As generally illustrated in FIGS. 14A to 14C, the flexible PCB 1400 can comprise one or more separate, but connected, segments. For example, the flexible PCB 1400 can include a main PCB segment 1402 and one or more smaller PCB segments 1404 such as smaller PCB segments 1404a, 1404b and 1404c. The smaller PCB segments 1404 can be directly or indirectly connected to the main PCB segment 1402. As shown in FIGS. 14A to 14C, the main PCB segment 1402 can be rolled to conform to the structural dimension of the ingestible medical device 1410.

An example embodiment of an ingestible medical device 1410 that uses the flexible PCB 1400 is described in further detail with reference to FIGS. 20A to 20L. The smaller PCB segments 1404a, 1404b and 1404c can be folded into one or more overlapping layers and fitted into the ingestible medical device 1410. In some embodiments, the smaller PCB segments 1404a, 1404b and 1404c can be layered around the power supply 40. It will be understood that the flexible PCB 1400 can have different configurations, such as different shapes and sizes, and/or a different number of segments.

The flexible PCB 1400 includes the main microcontroller 38, a magnetic switch 39, an optical encoder 1406, the transceiver 36, a motor driver 214, and a shunt resistor 1408. The shunt resistor 1408, as will be described in further details below, can be used for measuring the amount of current being drawn by the motor 42 in the ingestible medical device 1410. In this example embodiment, the optical encoder 1406 can be an infrared emitter/detector although other types of optical encoders can be used in other embodiments. Furthermore, in this example embodiment, the transceiver 36 can be an infrared emitter and a corresponding infrared detector although other types of transceivers can be used in other embodiments.

The electronic components can be located on any one of the main PCB segment 1402 or the smaller PCB segments 1404a, 1404b and 1404c. For example, as illustrated in FIG. 14A and the schematic circuit diagram 1450 of the flexible PCB 1400 in FIG. 14F, the main PCB segment 1402 can include the optical encoder 1406, the main microcontroller 38, the magnetic switch 39, the motor driver 214, the shunt resistor 1408 and a motor contact terminal 1412 for connecting to the motor 42. The small PCB segment 1404a can include a programming terminal 1414 for receiving operating instructions from an external device, such as the base station. The smaller PCB segment 1404c can include a power supply contact terminal 1416 for engaging the power supply 40 and also the transceiver 36. In other embodiments, other arrangements of these components on the flexible PCB 1400 are possible.

Figure 14D:
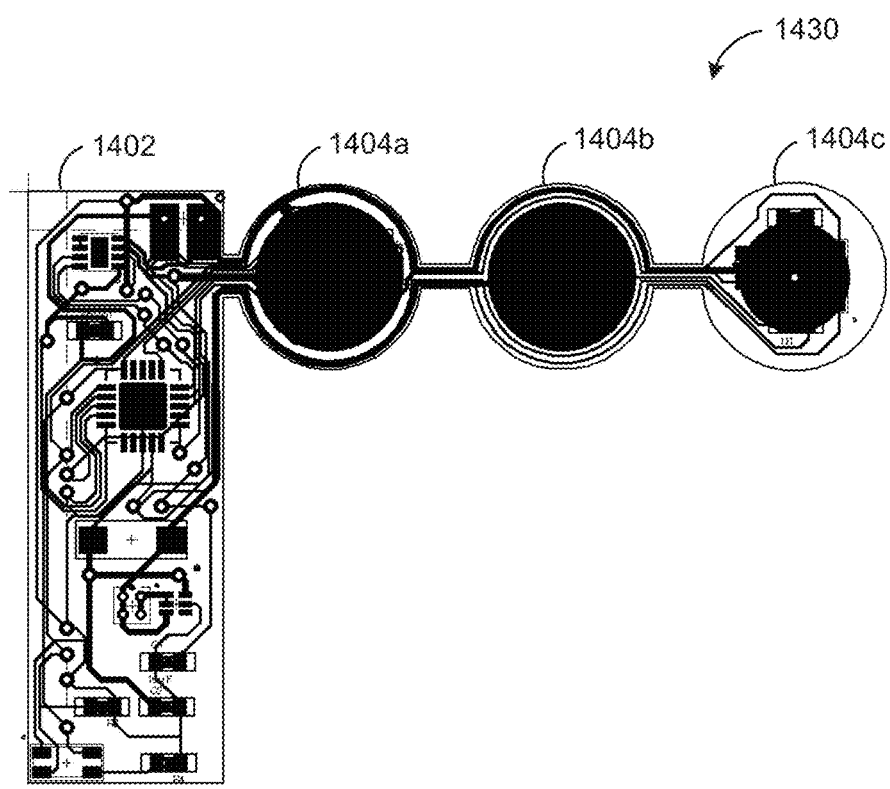
FIGS. 14D to 14F are example embodiments of circuit designs of the flexible PCB of FIGS. 14A and 14B.
Figure 14E:
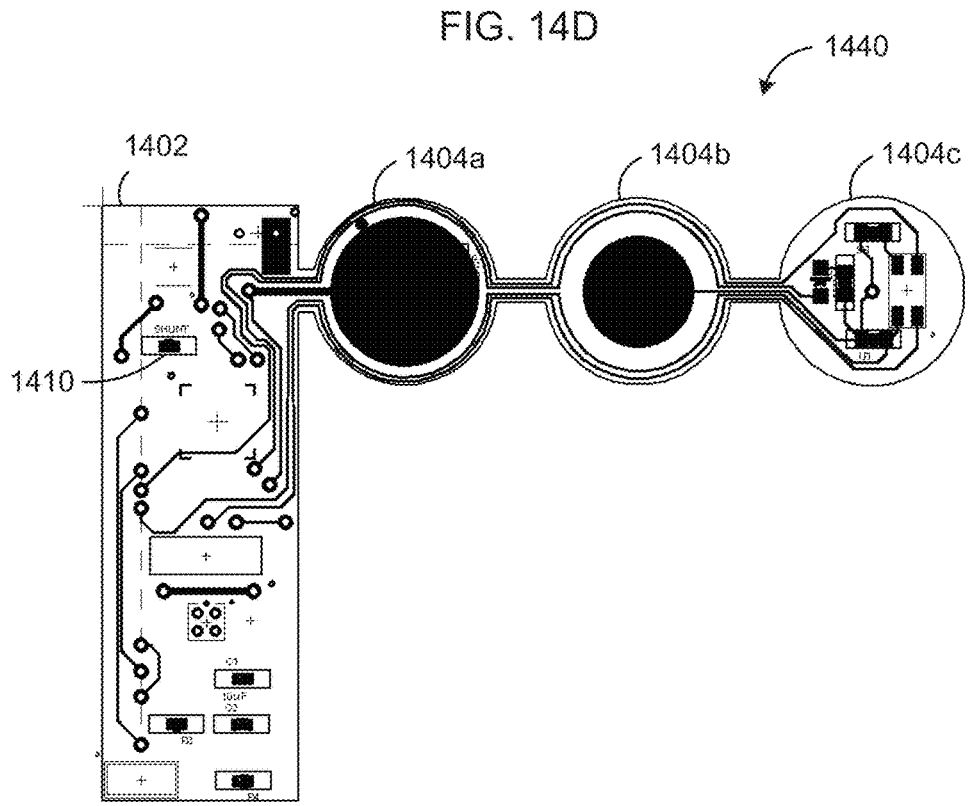
Figure 14F:
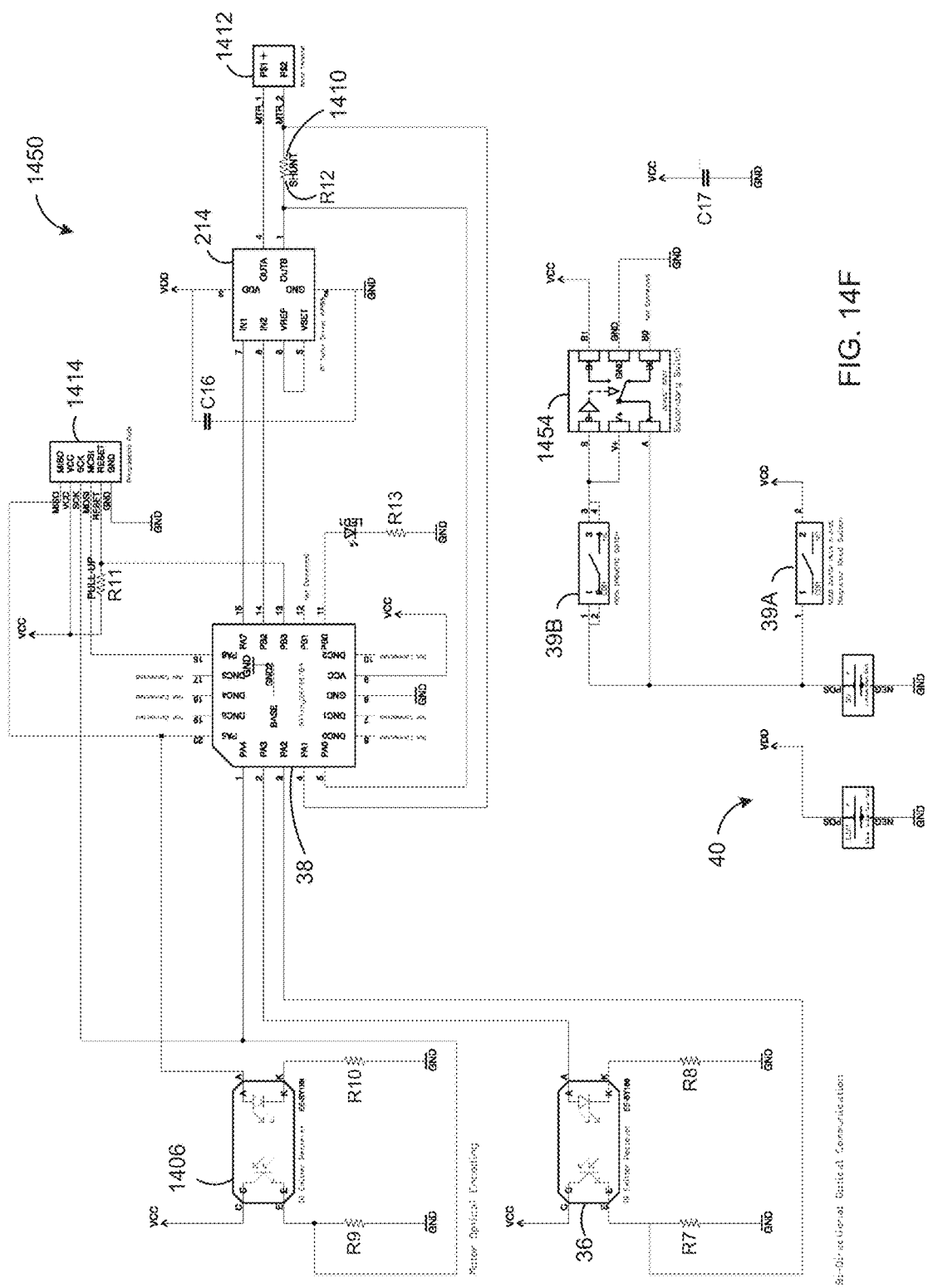

In the schematic circuit diagram 1450 of FIG. 14F, two magnetic switches 39A and 39B are included on the flexible PCB 1400. In this case, the magnetic switch 39B is a Microelectromechanical systems (MEMS) magnetic switch and therefore, a secondary SPDT switch 1454 is required. In some embodiments, only one magnetic switch 39 is located on the flexible PCB 1400. The magnetic switch 39 can be the MEMS magnetic switch 39B and so, the secondary SPDT switch 1454 is also required. It will be understood, though, the MEMS magnetic switch 39B may not always be available. Accordingly, the magnetic switch 39 can be another type of magnetic switch, as will be described below.

Example values for the components C16, C17 and R7 to R13 of FIG. 14F are provided in Table 1, below.

TABLE 1

Example Electronic Component Values for FIG. 14F

| Components | Range |
|---|---|
| C16 | 10 uF |
| C17 | 10 uF |
| R7 | 100 kΩ |
| R8 | 180 Ω |
| R9 | 100 kΩ |
| R10 | 180 Ω |
| R11 | 4.7 kΩ |
| R12 | <1 Ω |
| R13 | 30-120 Ω |

Each of the PCBs 32 and 44 includes various safety measures. For example, each of the PCBs 32 and 44 may include a back-up sub-circuit and a main sub-circuit. Both the back-up and the main sub-circuits are designed so that they can each independently handle the system current that flows though the ingestible medical device 10. As a consequence, when operating in tandem, the back-up and main sub-circuits can each handle half of the system current. However, if any area of the PCB 32 is damaged, either sub-circuit can still handle the full system current without any problems and thus, the PCB 32 can still operate without a breakdown in functionality or decrease in system performance. Accordingly, mechanical or electrical damage to a specific area of a board does not necessarily cause a breakdown in functionality or decrease in system performance.

Another safety measure that may be included is the use of digital fuses in each of the PCBs 32 and 44. The digital fuses may prevent components on the PCBs from inadvertent damage. The digital fuses may be reset by the main microcontroller 38 after the problem that caused one of the digital fuses to trip is resolved. Furthermore, in some embodiments, critical regions on the main PCB 32 and/or the secondary PCB 44 may include dual electrical pathways.

Similar to the PCBs 32 and 44, the flexible PCB 1400 may also include redundant electrical pathways, such as the back-up and main sub-circuits described above, as a safety measure. Unlike the PCBs 32 and 44, the flexible PCB 1400 does not require fuses. As will be described below, separate power supplies can be provided to each of the main microcontroller 38 and the motor 42. Accordingly, even though the main microcontroller 38 monitors and controls the amount of current being drawn by the motor 42, a failure at a power supply caused by an operation of the motor 42 will not compromise the operation of the other components. That is, despite the failure at the power supply of the motor 42, the main PCB 32 can continue to conduct measurements, to maintain a timer and to log data. However, in some embodiments, fuses may be provided on the flexible PCB 1400 as an additional safety measure.

The end enclosure 30 generally encloses the components in the first portion 12 of the ingestible medical device 10. Generally, the end enclosure 30 may be fabricated with optically and radio translucent or transparent material. This type of material allows for radio communication (e.g., for receiving and/or transmitting electromagnetic signals from the transceiver 36) as well as visual identification or inspection of the ingestible medical device 10. In some embodiments, the end enclosure may be fabricated from plastic.

Figure 3A:
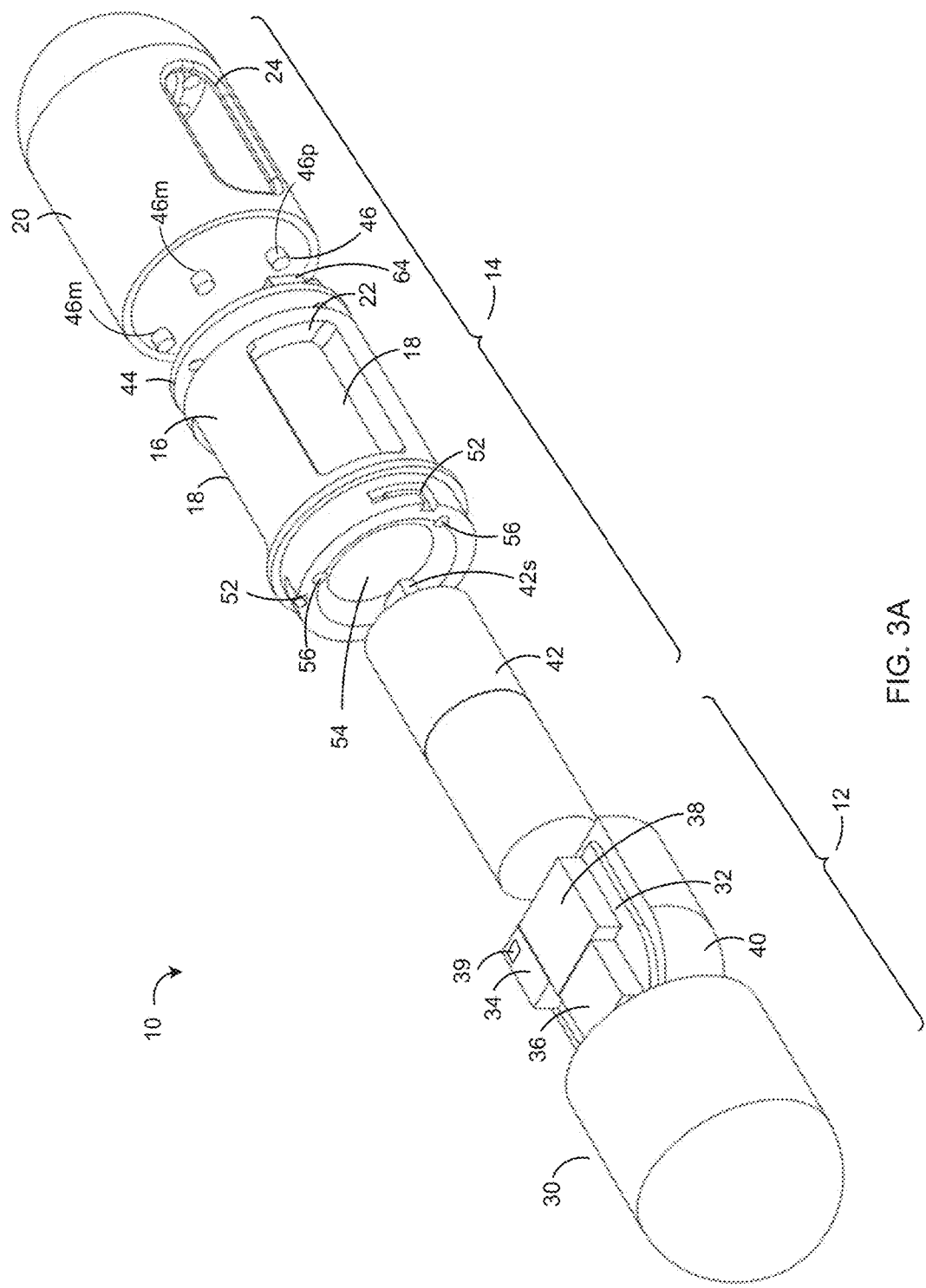
FIG. 3A is an exploded view of the ingestible medical device of FIG. 1.
Figure 3C:
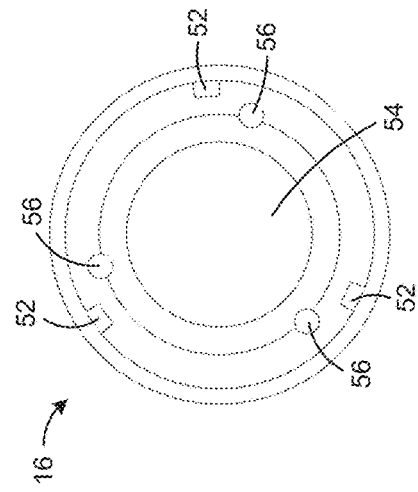
FIGS. 3B to 3G are views of the various components of the medical device shown in FIG. 3A.
Figure 3E:
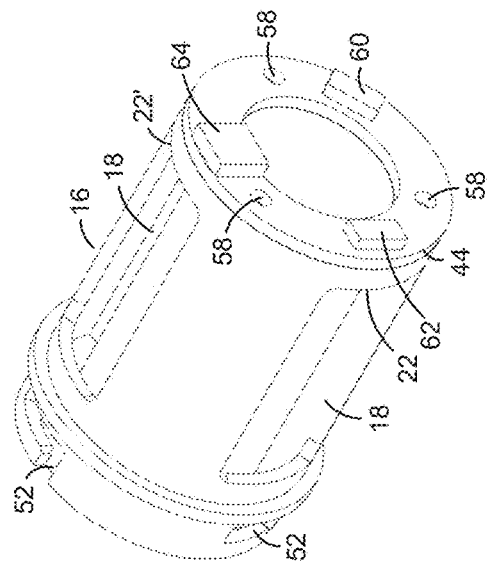
Figure 3B:
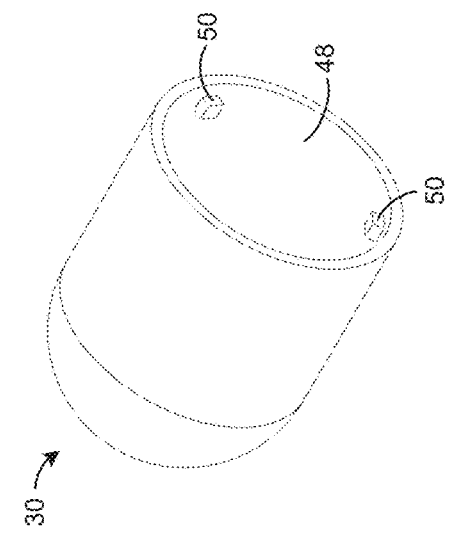

Referring now to FIG. 3B, shown therein is a view of the interior of the end enclosure 30. The end enclosure 30 provides a hollow space defined by an inner wall 48 that is cylindrical with a domed end portion. The end enclosure 30 also includes engagement members 50 for aligning and releasably engaging with the storage sub-unit 16 to releasably lock the end enclosure 30 in place during operation. In particular, the engagement members 50 releasably engage complementary structures 52 in the storage sub-unit 16 (e.g., as illustrated in FIG. 3A). When the end enclosure 30 locks with the storage sub-unit 16, the end enclosure 30 overlaps with a rear of the storage sub-unit 16 and creates a seal. In some embodiments, the overlap between the end enclosure 30 and the storage sub-unit 16 may span a width of 3 millimeters.

Referring again to FIG. 3A, the communication subsystem includes the communication peripherals 34 and the transceiver 36, at least one of which interfaces with the main microcontroller 38. The communication peripherals 34 typically include an antenna and a crystal oscillator. The antenna may be fabricated from a flexible PCB material. Since the crystal oscillator is external to the main microcontroller 38, it may be more accurate than an oscillator located inside the main microcontroller 38 since the internal oscillator may drift in oscillation frequency due to changes in temperature inside the main microcontroller 38 and thus, compromise wireless communication. By using the external crystal oscillator in the communication subsystem, wireless communication between the ingestible medical device 10 and a base station can be more reliable.

The transceiver 36 is used for communicating with an external transceiver located in the base station (e.g., an RF transceiver on a dock or an infrared transmitter and/or receiver on the dock). The base station may be used for initially programming the ingestible medical device 10 with operating instructions and/or communicating with the ingestible medical device 10 during operation in real-time or after the ingestible medical device 10 is extracted from the body.

The transceiver 36 includes a radio, for example, an infrared (IR) transmitter and receiver, and/or a radio-frequency (RF) transmitter and/or receiver. In embodiments that utilize IR communication, the IR transmitter and receiver can be configured to operate using modulated infrared light, i.e. light within a wavelength range of 850 nm to 930 nm. Furthermore, the IR receiver may be included in the ingestible medical device 10 for receiving programming instructions from the IR transmitter at the base station and the IR transmitter may be included in the ingestible medical device 10 for transmitting data to the IR receiver at the base station. Bidirectional IR communication between the ingestible medical device 10 and the base station can therefore be provided.

In embodiments that utilize RF, an RF receiver may be included for receiving programming instructions or a RF transceiver may be included for receiving and transmitting data. In some embodiments, the transmission capability on the RF transceiver may be deactivated. Both the RF receiver and RF transceiver can be configured to operate using a wireless communication protocol, such as ZigBee™ or ANT™.

In some embodiments, the transceiver 36 may be implemented using a System-In-Package (SIP) in which the transceiver 36 is an integrated chip that is separate from the main microcontroller 38. The associated wireless protocol stack is contained within and managed by the transceiver 36. The transceiver 36 may interface with the main microcontroller 38 through Serial Peripheral interface (SPI) or Single Wire Interface (SWI) protocols.

Alternatively, in some embodiments, a single-chip solution such as a System-on-Chip (SoC), or an Application-Specific Integrated Circuit (ASIC) may be used. The ASIC can combine the transceiver 36 and the main microcontroller 38 by incorporating an internal radio and other related supporting components in the main microcontroller 38.

The main microcontroller 38 generally controls the operation of the ingestible medical device 10. Accordingly, the main microcontroller 38 includes programmable and control circuitries for holding and executing firmware and coordinating all functions of the ingestible medical device 10 and the other peripherals embedded on the main PCB 32. For example, the main controller 38 may control the amount of current provided to the motor 42 based on a positioning signal provided from the secondary PCB 44. The main microcontroller 38 may be implemented using an 8-bit microcontroller, such as the ATtiny family of microcontrollers from ATMEL™, or a 32-bit microcontroller, such as the STM32 family of microcontrollers from STMicroelectronics™.

The main microcontroller 38 also includes one or more memory elements (e.g., a flash memory) for storing a core program, an oscillator or crystal, and an Analog-to-Digital (A/D) converter (e.g., a 10-bit A/D converter). The A/D converter may be used for receiving signals that are used to determine a position of an encoding magnet on the encoding magnet arrangement 46 as well as for receiving signals to measure a current drawn by the motor 42 during operation. In some embodiment, the A/D converter may also be used with one or more environmental sensors (e.g., an Ion-Selective Field Effect Transistors (ISFETs) for sensing pH levels, Resistive Thermal Devices (RTDs) for sensing temperature, and/or piezoelectric elements for measuring pressure, etc.).

Examples of peripheral components that may be embedded on the main PCB 32 include a high-current switch, one or more LEDs, a magnetic switch 39, another A/D converter, one or more environmental sensors (e.g., the ISFETs, the RTDs and the piezoelectric system) and one or more passive electrical components.

Still referring to FIG. 3A, the power supply 40 is attached coupled to the ventral side of the main PCB 32. Generally, metallic slots on the main PCB 32 may act as both electrical contacts and holders for legs of the power supply 40. The holders on the main PCB 32 receive the legs of the power supply 40 and hold them in place.

For a majority of the time that the ingestible medical device 10 is in operation, the main microcontroller 38 is the only component that draws power. When the microcontroller 38 is not in use, the peripheral components are generally powered down.

In general, the main microcontroller 38 is designed to supply and/or sink a small amount of current. For example, when implementing the main microcontroller 38 with an ATtiny13A microcontroller, each of the General Input Output Pins (GPIOS) can supply/sink a maximum of 40 mA with a system maximum of 200 mA. In a low power mode, the ATtiny13A microcontroller consumes as low as 190 µA at 1.8 V and 1 MHz. As a result, the ingestible medical device 10 may generally be operable using the power supply 40 for more than 24 hours, with five minutes of motor actuation. This battery life may typically be sufficient for the ingestible medical device 10 to endure a passage of the GI tract of most individuals, and to endure an additional amount of time for retrieval and extraction.

In some embodiments, a bare-cell battery (e.g., a lithium-polymer battery) without a rigid housing may be used so that the battery can be molded or manufactured to a desired shape. The shape of the bare-cell battery, thus, is flexible and can more easily conform to the capsule shape of the ingestible medical device 10.

In some embodiments, the power supply 40 may include a silver oxide battery. For example, a silver oxide coin cell type battery, such as those manufactured by Renata™, may be used since the silver oxide coin cell battery has discharge characteristics that suit the operation of the ingestible medical device 10.

In some embodiments, the power supply 40 may be removed from the ingestible medical device 10 to be recharged by recharging circuitry that is external to the ingestible medical device 10. Alternatively, in some embodiments, the power supply 40 may be recharged while in the medical device when recharging circuitry is included on the main PCB 32.

Unlike the main microcontroller 38, the motor 42 generally requires a high discharge capacity. For example, at 3V operating voltage, a 6 mm pager gear motor may draw a current of 120 mA when unloaded and a current of 230 mA when stalled. It will be understood that the 6 mm motor is merely an example of a motor that can be used in the ingestible medical device 10 and that other types of motor with similar operating characteristics and varying dimensions may be used. The power supply 40, thus, needs to supply a high energy density and to discharge a high current on demand (e.g., to discharge a high level of current for momentary periods of time). An example of such a power supply may be a lithium-polymer battery (e.g., a 20 mAh battery that operates at 3.7V). Lithium polymer chemistry provides high energy density and can discharge high current on demand (e.g., a discharge of 10 Coulombs continuously and a maximum of 20 Coulombs). The high energy density of the lithium polymer chemistry also indicates that the lithium battery has a long battery life. Batteries formed using lithium polymer chemistry may also have a compact form.

The power supply 40 can include one or more batteries formed from different chemical compositions. This can be helpful in accommodating the different power requirements of the various components in the ingestible medical device 10. Also, splitting the power supply 40 can also prevent a temporary interruption or change at the power supply 40 from affecting the overall operation of the ingestible medical device 10. For example, as described above, the motor 42 requires a battery with a high discharge capacity since the motor 42 needs to draw a high level of current in order to overcome the static friction associated with rotating the chamber enclosure 20 or the storage sub-unit 16. Due to the high level of current draw, the voltage of the battery drops temporarily. However, the temporary voltage drop at the battery could negatively affect the operation of the other components relying on that battery. For example, the voltage drop at the battery could cause the main microcontroller 38 to reset.

Accordingly, the power supply 40 can include a first battery cell group for supplying power to the motor 42 and a second battery cell group for supplying power to the other components in the ingestible medical device 10. The first and second battery cell groups each have at least one battery cell. For example, a silver oxide battery could be included in the power supply 40 of the first battery cell for supplying power to the motor 42 and a lithium battery (e.g., a lithium coin cell battery operating at 3.3V) could be included in the power supply 40 of the second battery cell for supplying power to the other components in the ingestible medical device 10.

In some embodiments, the power supply 40 may include a silver oxide battery cell for supplying power to the motor 42 and one or more silver oxide battery cells for supplying power to the other components in the ingestible medical device 10. The battery cells that supply power to the power supply 40 may operate at 1.55V, for example.

As briefly described above, since the main microcontroller 38 controls the amount of power supplied to the motor 42, an intermediary component may be included between the main microcontroller 38 and the motor 42 for electrical protection. The intermediary component may protect the main microcontroller 38 from the high current discharge so that a power supply 40 that meets both the power requirements of the motor 42 and the electrical limitations of the main microcontroller 38 may be used.

In some embodiments, the intermediary component is a switch that is capable of handling high levels of current (e.g., an analog Single-Pole Double Throw (SPDT) switch). Alternatively, in some embodiments, the intermediary component is a Double-Pole Double-Throw (DPDT) switch. The DPDT switch enables an applied polarity to be arbitrarily switched for facilitating bidirectional motion of the motor 42 (and thus, also the chamber enclosure 20 since it is rotated by the motor 42 or in an alternative embodiment the rotational motion of the storage sub-unit 16).

The DPDT switch includes two common legs each of which may be connected to either of a pair of terminals (or "throwing legs"). That is, each pair of terminals may include an analog ground terminal and an analog power terminal (e.g., about 3.7 V). Each of the two common legs may switch from connecting to the analog ground terminal and connecting to the analog power terminal. The other end of each of the two common legs is connected to either contact on the motor 42. The direction that the motor 42 rotates depends on the polarity that is applied to the contacts on the motor 42. Bidirectional motion thus may be available with a DPDT switch. A resistor and a diode are also included on the main PCB 32 to further protect the main microcontroller 38 from current surge and motor kickback current.

In other embodiments, a dual bridge motor driver is included on the main PCB 32 to protect the main microcontroller 38 from current surge and motor kickback current. The dual bridge motor driver integrates the DPDT switch, the resistor and the diode components together into a single package that is well suited for handling inductive loading.

As described above, the motor 42 is coupled to the main microcontroller 38 for receiving power from the power supply 40. The motor 42 may then rotate the chamber enclosure 20 around the storage sub-unit 16. Generally, the motor 42 is implemented such that it provides a high torque without external gearing. In some embodiments, the motor 42 is a miniature DC motor. In some embodiments, the DC motor may be brushless. For example, a 6 mm diameter pager motor with 25:1 reduction planetary gearing (e.g., as manufactured by Firgelli Automations) may be used. The 25:1 reduction planetary gearing generally provides a proportional increase in torque and decrease in revolutions per minute (RPM).

As illustrated in FIG. 3A, two concentric layers form around the motor 42. In order to maximize space inside the ingestible medical device 10, the storage sub-unit 16 and the chamber enclosure 20 are built to fit concentrically around the motor 42. A first layer around the motor 42 is the storage sub-unit 16 and a second layer around the motor 42 is the chamber enclosure 20. Generally, the storage sub-unit 16 may be manufactured using plastic.

Referring to FIG. 3C, illustrated therein is a top view of the storage sub-unit 16. The motor 42 is inserted into a motor compartment 54 that is located in the center of the storage sub-unit 16. Also shown in FIG. 3C are access holes 56 and engagement members 52 located on the storage sub-unit 16. The access holes 56 are passages for wires connecting the main PCB 32 to the secondary PCB 44. The engagement members 52 are for receiving the engagement members 50 located within the end enclosure 30 in order to align and releasably lock the end enclosure 30 to the storage sub-unit 16. In alternative embodiments, there can be a different number of access holes 56 and engagement members 52 as is needed for proper operation and connection of elements.

Figure 3D:
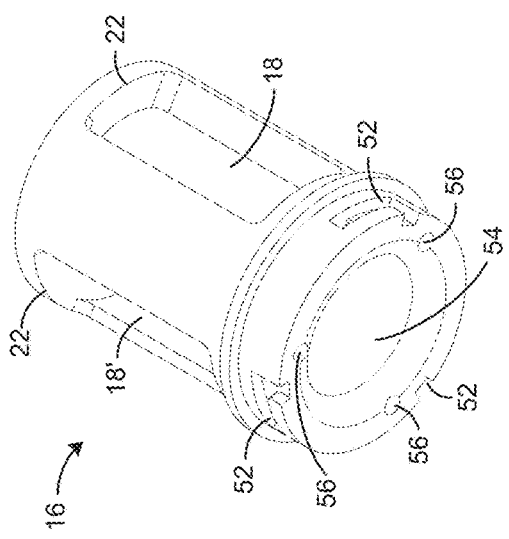

Referring now to FIG. 3D, illustrated therein is an exploded view of the storage sub-unit 16. The storage sub-unit 16 includes several chambers 18. The chambers 18 are generally long rectangular grooves along the length of the cylindrical-shaped storage sub-unit 16. However, it will be understood that the chambers 18 can take any shape and the shape may vary depending on the intended application of the ingestible medical device 10. For example, if more chambers 18 are required, smaller chambers 18 can be used. In another example, the chambers 18 can be shaped so that samples can be more easily collected, such as altering the edges of the chamber openings 22 to reduce surface tension and also provide a two-phase flow. Each of the chambers 18 is isolated from one another so that one or more discrete substances may be stored either from sampling during operation or to be stored prior to usage for release during operation. Generally, each of the chambers 18 has dimensions to store a usable sample size, such as for example a volume of about 100 μL. There can be embodiments in which there are an alternative number of chambers 18 such as one, two or more than three.

In at least some embodiments, each of the chambers 18 and the spacing between the chambers 18 may be subjected to hydrophilic and hydrophobic treatments, respectively, to minimize cross-contamination between stored substances.

Each chamber 18 has a corresponding chamber opening 22. In some embodiments, the chamber openings 22 and the chambers 18 are evenly distributed around the circumference of the storage sub-unit 16. For example, in the example embodiment of the ingestible medical device 10, the storage sub-unit 16 includes three separate chambers 18 having corresponding chamber openings 22 with centers that are spaced 120° apart from each other. The chamber openings 22 may span an arc of approximately 60°. Therefore, areas that are not recessed (e.g., each with a span of approximately 60°) may be provided between each of the chamber openings 22 on the storage sub-unit 16. In some embodiments, the chamber openings 22 and the corresponding chambers 18 are unevenly distributed around the circumference of the storage sub-unit 16. For example, the chamber openings 22 and the corresponding chambers 18 may be located closer together when it is undesirable for the ingestible medical device 10 to pause between each collection or release of a substance. In alternative embodiments, the chamber opening 22 can span an arc having a different circumferential extent.

In some embodiments, a span at which the chamber 18 is recessed into the storage sub-unit 16 may correspond with the span of the corresponding chamber opening 22. For example, if the chamber opening 22 spans an arc of 60°, the span at which the corresponding chamber 18 is recessed into the storage sub-unit 16 is also 60°.

Alternatively, in some other embodiments, a chamber in the storage sub-unit 16 is an extended chamber 18', as illustrated in FIG. 3D. The extended chamber 18' has a greater volume than a regular chamber 18 because the extended chamber 18' is recessed further around a circumferential span of the storage sub-unit 16 than a regular chamber 18. In this way, the extended chamber 18' is only partially exposed by its corresponding chamber opening 22. For example, while the chamber opening 22 of the corresponding extended chamber 18' has a circumferential span of 60°, the extended chamber 18' can be recessed around a circumferential span of 90° or 120°. As a result, only two-thirds or a half of the extended chamber 18' is exposed by the corresponding chamber opening 22.

In some embodiments, the walls of the chambers 18 can be angled and/or tapered.

Alternatively, in some embodiments, one or more electrical devices may be used within the chambers 18 since the chambers 18 are located so close to the electrical wires (or buses) that pass through the access holes 56. For example, micro-peltier chips may be used in at least one of the chambers 18 for thermoelectric cooling of a substance stored therein.

Alternatively, in some embodiments, space between the chambers 18 in the storage sub-unit 16 may be recessed and outfitted for additional functionality, such as performing in-vivo experiments. For example, an extended chamber 18' can be partitioned for storing reagents that interact with collected samples for performing in-vivo experiments. In another example, a portion of the extended chamber 18' can be partitioned and merged with the electrical wires passing through the access holes 56 for storing electrical devices to be used for performing in-vivo experiments.

In some embodiments, the storage sub-unit 16 and the chamber enclosure 20 may be physically altered according to an intended use of the ingestible medical device 10. For example, if the ingestible medical device 10 is to be used for releasing a substance into a body, the ingestible medical device 10 may be, in addition to software changes, physically varied. For example, each chamber 18 may be further subdivided into one or more compartments. This will allow different reagents to be stored in one chamber 18 but isolated within the chamber 18 by storing each of the reagents in a different compartment of the chamber 18. For example, the chamber 18 can be subdivided into halves or quadrants, and each half or quadrant is used to store a different reagent. Correspondingly, the access port 24 on the chamber enclosure 20 may also be modified in order to accommodate the multiple compartments in the chambers 18. For example, the access port 24 can be constricted in size to vary the rate at which reagents inside the chamber 18 are released into the body. Specifically, certain reagents may be highly active and only a small quantity needs to be released into the body.

As described above, the chambers 18 in the storage sub-unit 16 may be used for storing samples that are collected from the GI tract and/or storing substances for release into the GI tract. Therefore, both the chamber openings 22 and the access port 24 are sufficiently large to accommodate movement of materials of interest from the GI into the chambers 18 through peristaltic motion.

Reference is now made to FIGS. 13A to 13E, which are diagrams illustrating an ingestible medical device 1310 operating with a bidirectional rotation. As described above, the storage sub-unit 16 of the ingestible medical device 1310 may have a N number of chambers 18 and a N−1 number of areas 1302 that are not recessed (e.g., non-recessed areas) separating the chambers 18. Therefore, two chambers 18 are not separated by a non-recessed area 1302 and are adjacent to each other, such as a first chamber 18a and second chamber 18b. The ingestible medical device 1310 shown in the example embodiment of FIGS. 13A to 13E includes three chambers 18, namely chambers 18a, 18b and 18c, and two non-recessed areas 1302a and 1302b. As illustrated in FIGS. 13A to 13E, the first chamber 18a and the second chamber 18b are adjacent chambers because they are separated by a divider 1312 but not by a non-recessed area 1302.

In order for the ingestible medical device 1310 to continue to apply the "closed-loop" revolver mechanism to avoid cross contamination between samples being collected into and/or substances being released from each of the chambers 18, a predetermined sequence of bidirectional rotations can be used. In the example embodiment shown in FIGS. 13A to 13E, the storage sub-unit 16 is the rotational element. However, in embodiments in which the chamber enclosure 20 is configured to rotate, the chamber enclosure 20 can similarly operate in the bidirectional rotation described with reference to FIGS. 13A to 13E.

When the ingestible medical device 1310 is at a closed position 1310a (FIG. 13A), the storage sub-unit 16 can rotate in a first direction, such as a counter-clockwise direction, to align the access port 24 with a chamber opening 22a of the first chamber 18a (FIG. 13B). After a collection or release operation is completed at the first chamber 18a, the storage sub-unit 16 can rotate in a second direction, such as a clockwise direction, to return the ingestible medical device 1310 to the closed position 1310a shown in FIG. 13A.

Each position illustrated in each of FIGS. 13A to 13E corresponds to an alignment of the access port 24 with a chamber opening 22 of a chamber 18 or with a non-recessed area 1302. To move from one position to another position, the rotatable element of the ingestible medical device 1310 can move one or more rotational steps. For example, the rotatable element can move from the position 1310a to the position 1310b in one rotational movement or in multiple rotational steps.

The storage sub-unit 16 can continue to rotate in the second direction to continue to collect samples into and/or to release substances from the remaining chambers 18, such as in the positions 1310c, 1310d and 1310e of the ingestible medical device 1310 illustrated respectively in FIGS. 13C to 13E. After the storage sub-unit 16 rotates in the second direction a certain number of positions so that the access port 24 is aligned with a chamber opening 22b of the second chamber 18b (FIG. 13E), the storage sub-unit 16 can again rotate in the first direction to avoid aligning the access port 24 with the first chamber 18a again. The ingestible medical device 1310 is therefore returned to the closed position 1310e shown in FIG. 13D. For example, the storage sub-unit 16 may rotate in the second direction for a predetermined number of stages as determined from the below formula:

# of Positions in Second Direction=2×(N−1), where N is the number of chambers 18 in the storage sub-unit 16, before the storage sub-unit 16 again rotates in the first direction to complete the collection and/or release operation.

Referring now to FIG. 3E, illustrated therein is an isometric view of the storage sub-unit 16 coupled with the secondary PCB 44. The secondary PCB 44 is coupled to the main PCB 32 by wires (e.g., flexible cables) that pass through one or more access holes 58 in the secondary PCB 44 from corresponding one or more access holes 56 on the storage sub-unit 16. These wires carry power from the main PCB 32 to the secondary PCB 44 as well as other signals such as a positioning signal from the secondary PCB 44 to the main microcontroller 38.

The secondary PCB 44 is annular and includes one or more peripheral electronic components (e.g., a capacitor 62 and a resistor 60, which can be used as a pull-up resistor), and a sensor 64. The sensor 64 may be placed behind a thin wall of plastic to protect it against mechanical, liquid and/or chemical damage. The sensor 64 is a magnetic sensor such as an omnidirectional hall-effect sensor. For example, the sensor 64 can be an omnidirectional hall-effect sensor that is implemented in an integrated circuit. Generally, the sensor 64 operates by sensing a magnetic signal provided from the encoding magnet arrangement 46 and generates a corresponding positioning signal that is provided to the main microcontroller 38.

Generally, if the sensor 64 is aligned with a center of a chamber opening 22, then that chamber opening 22 may then be referred to as a primary chamber opening 22' to provide a frame of reference. For example, as described above, in an example embodiment in which three chambers 18 are included in the storage subunit 16, each center of a chamber opening 22 is spaced approximately 120° from one another. Accordingly, a center of a first chamber opening 22 is located approximately 120° from the center of the primary chamber opening 22', and a third chamber opening 22 is located approximately 240° (or alternatively −120°) from the center of the primary chamber opening 22'. The relative positions of the sensor 64 and the encoding magnet arrangement result in different activity in the positioning signal which indicates the location of the access port 24 with respect to one of the chamber openings 22, as will be explained in further detail with regards to FIGS. 5 and 6.

Generally, the sensor 64 may be any contactless and compact proximity sensor. In alternative embodiments, the sensor 64 may be based on any of a capacitive, resistive, and/or optical encoding technique. For each of these encoding techniques, the encoding magnet arrangement 46 is not used. Instead, dielectric materials, metal, or semi-conductive material that correspond to the particular sensor configuration may be used.

For example, an optical technique may include the use of a diode-receiver pair and patterns etched into the chamber enclosure 20 that create corresponding areas of high and low reflection. A sinusoidal pattern is then generated during the rotation of the chamber enclosure 20 which can be used for determining the position of the access port 24.

An example optical encoding technique that relies on the operation of the optical encoder 1406 is described below with reference to FIG. 19. Generally, the optical encoder 1406 replaces the sensor 64 and operates to detect a position of the storage sub-unit 16 in relation to the access port 24. For example, the optical encoder 1406 may determine the position of the storage sub-unit 16 by detecting a location of one or more protrusion members provided on the storage sub-unit 16. In another example, the optical encoder 1406 may determine the position of the storage sub-unit 16 by distinguishing between light regions and dark regions that are printed directly onto the motor 42. In this case, the dark regions are used as location markers.

Figure 3F:
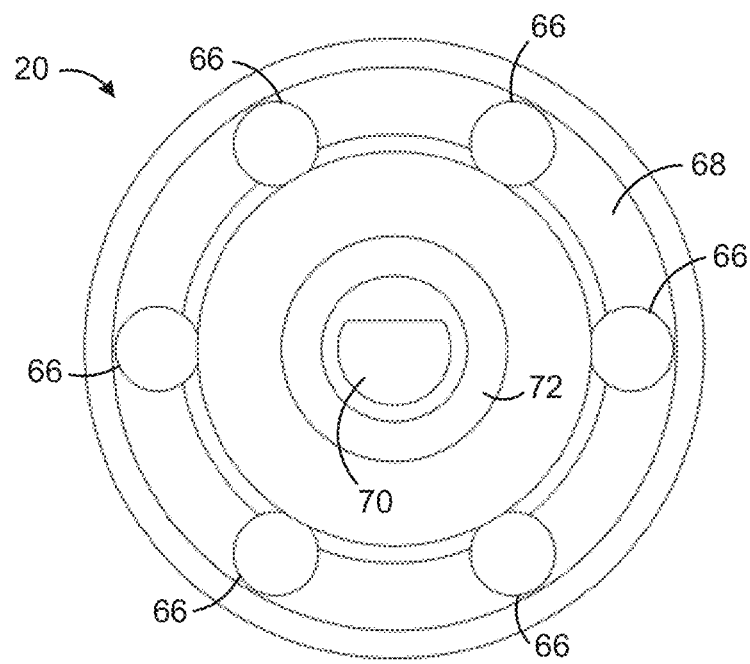

Referring back to FIG. 3A, the encoding magnet arrangement 46 is generally illustrated to be located across from the secondary PCB 44. With reference now to FIG. 3F, illustrated therein is an interior view of the chamber enclosure 20 which shows that each encoding magnet of the encoding magnet arrangement 46 is positioned into a corresponding aperture 66 around a circumference of the interior of the chamber enclosure 20. The apertures 66 can protrude from the inner walls of the chamber enclosure 20 or can be situated on a flat ring or annular shoulder 68 within the chamber enclosure 20. A truncated aperture 70 is also provided from another portion of the inner wall of the chamber enclosure 20 or another flat ring or annular shoulder 72 within the chamber enclosure 20. The truncated aperture 70 is used to couple a shaft 42s of the motor 42 to the chamber enclosure 20 in order to rotate the chamber enclosure 20. Since the encoding magnet arrangement 46 is coupled to the chamber enclosure 20, the encoding magnet arrangement 46 also rotates along with the chamber enclosure 20.

Generally, the encoding magnet arrangement 46 includes one or more encoding magnets 46m. The number of magnets 46m can be selected based on a size and strength of the magnets 46m. For example, if the magnets 46m are very strong and located very close together, the resulting magnetic field lines may overlap and the sensor 64 may be unable to identify which magnetic field lines correspond with which magnets 46m and the encoding magnet arrangement 46 may appear to the sensor 64 as a single annular magnet.

The encoding magnets 46m can be any sufficiently strong and compact disc-shaped magnets with a biocompatible coating. For example, a gold-plated neodymium magnet may be used for the encoding magnets 46m. The encoding magnets 46m can have a diameter of 1.5 millimeters and a depth 0.75 millimeter, for example.

In some embodiments, the encoding magnet arrangement 46 may have a magnet that is designated as a primary magnet 46p for use as a point of reference on the ingestible medical device 10, as illustrated in FIG. 3A. Since the ingestible medical device 10 is closed when it is first initialized, all chamber openings 22 are sealed and the magnet 46m located in front of the sensor 64 will be designated the primary magnet 46p. In cases where there is more than one magnet 46m in the encoding magnet arrangement 46, the magnets 46m are distributed around a circumference of the chamber enclosure 20 at intervals that correspond with the distribution of the chambers 18 in the storage sub-unit 16 since the magnets 46m are used for aligning the access port 24 with each of the chambers 18. For example, the magnets 46m are distributed at evenly spaced intervals if the chambers 18 are evenly distributed. However, if the chambers 18 are closely grouped together, the magnets 46m are also grouped together according to the configuration of the chambers 18.

In some embodiments, the number of magnets 46m used in the encoding magnet arrangement 46 is less than a total number of open and closed states in one revolution of the chamber enclosure 20, or, in other words, there are fewer than two magnets 46m for each chamber 18. For example, in a storage sub-unit 16 with three chambers 18 that are each separated by three areas that are not recessed, the total number of open and closed states during one revolution of the chamber enclosure 20 is six. The number of magnets 46m used in the encoding magnet arrangement 46 can, thus, be less than six. For example, one magnet 46m can be used in the encoding magnet arrangement 46. As described above, this magnet 46m may be referred to as the primary magnet 46p and is located at the center of the access port 24 within the chamber enclosure 20.

For this configuration of the encoding magnet arrangement 46, an analog positioning technique, as described below, is used for positioning the access port 24 with each of the chamber openings 22. One advantage of using fewer magnets 46m in the encoding magnet arrangement 46 is that less space is required for coupling the magnet to the storage sub-unit 16. As a result, the construction and assembly of the ingestible medical device 10 is simplified and the cost of construction is reduced. One limitation, however, is that the A/D converter on the main microcontroller 38 must have sufficient resolution (e.g., a number of bits) for accurately positioning the access port 24.

In some embodiments, the number of magnets 46m used in the encoding magnet arrangement 46 is equal or greater than a total number of open and closed states in one revolution of the chamber enclosure 20, or there are at least two magnets 46m for each chamber 18. For example, as described above, in a storage sub-unit 16 with three chambers 18 that are each separated by three areas that are not recessed, the total number of open and closed states during one revolution of the chamber enclosure 20 is six. The number of magnets 46m used in the encoding magnet arrangement 46 can, thus, be six or greater than six. For this configuration of encoding magnet arrangement 46, a digital positioning technique (described below) is used for positioning the access port 24 with each of the chamber openings 22.

One advantage of the digital positioning technique, and thus, of using a greater number of magnets 46m, is that the A/D converter on the main microcontroller 38 is not required to have a minimum resolution. As is described below, the resolution attainable by the digital positioning technique corresponds with the number of magnets 46m used in the encoding magnet arrangement 46. Therefore, as more magnets 46m are used on the encoding magnet arrangement 46, the resolution, or the degree of accuracy at which the access port 24 can be positioned increases which also allows an increase in the speed for performing this measurement and hence alignment of the access port 24 with one of the chamber openings 22.

In some embodiments in which the storage sub-unit 16 has three chambers 18, six magnets 46m can be used in the encoding magnet arrangement 46. As described above, the six magnets 46m can be evenly distributed around the circumference of the chamber enclosure 20 to correspond with three evenly distributed chambers 18 and one of the six magnets 46m (e.g., the primary magnet 46p) is aligned with the sensor 64 when the ingestible medical device 10 is initially in a closed position. Another magnet 46m is located at the center of the access port 24 within the chamber enclosure 20. The center points of each of the magnets 46m are separated from one another by a circular arc of about 60°.

In some embodiments in which the storage sub-unit 16 has three chambers 18, twelve magnets 46m can be used in the encoding magnet arrangement 46. As previously described, the twelve magnets 46m can be evenly distributed around a circumference of the chamber enclosure 20, if the three chambers 18 are also evenly distributed, and one of the twelve magnets 46 (e.g., the primary magnet 46p) is aligned with the sensor 64 when the ingestible medical device 10 is initially in a closed position. Another magnet 46m is located at the center of the access port 24 within the chamber enclosure 20. The center points of each of the magnets 46m are separated from one another by a circular arc of about 30°.

Generally, the secondary PCB 44 operates with the encoding magnet arrangement 46 and the sensor 64 to form a position encoder sub-unit. The position encoder sub-unit provides a positioning signal (e.g., a feedback signal) to the main microcontroller 38 for determining the position of the access port 24 relative to the chambers 18.

There are several advantages to using a position encoder sub-unit that is external to the motor 42. For example, the components of the position encoder sub-unit are less expensive than a feedback system that is directly integrated into the motor 42. Also, the external position encoder sub-unit helps prevent any misalignment that may occur if a stepper motor is used and skips steps.

Figure 3G:
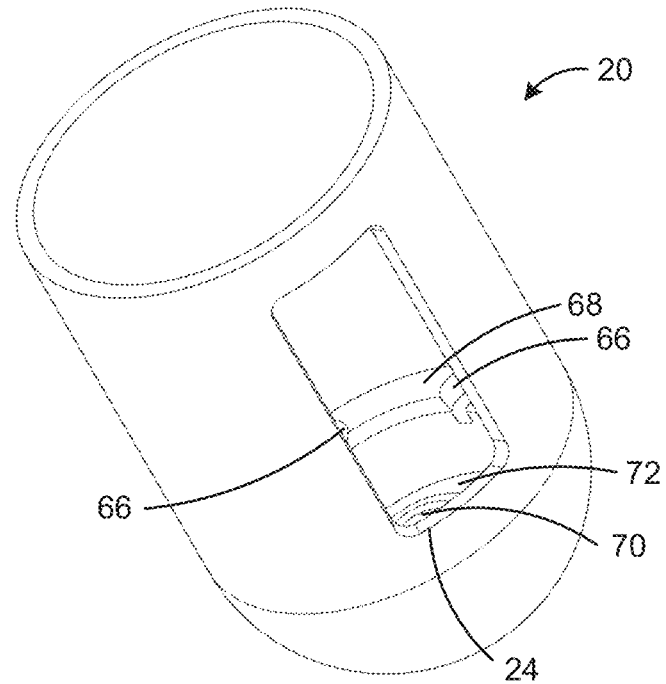

The chamber enclosure 20 is the second concentric layer that surrounds the motor 42 and also serves as an enclosure for the second portion 14 of the ingestible medical device 10. Referring now to FIG. 3G, illustrated therein is an isometric view of the chamber enclosure 20. The access port 24 of the chamber enclosure 20 allows a substance to enter into a chamber 18 of the storage sub-unit 16 and/or be released from a chamber 18 of the storage sub-unit 16 into the body when the access port 24 is aligned with a corresponding chamber opening 22.

As described above with reference to FIGS. 2A to 2C, as the chamber enclosure 20 rotates, the access port 24 may become aligned with a first chamber opening 22 (e.g., FIG. 2A). After a sample is collected or a substance is released, the motor 42 continues to rotate the chamber enclosure 20 so that the access port 24 is no longer aligned with the first chamber opening 22 (e.g., FIG. 2C). At this point, the access port 24 overlays non-recessed regions of the storage sub-unit 16 so that no substance may enter into or exit from any of the chambers 18. These non-recessed regions of the storage sub-unit 16 in conjunction with the inner walls of the chamber enclosure 20 act as "seals" for the chambers 18.

Figure 4:
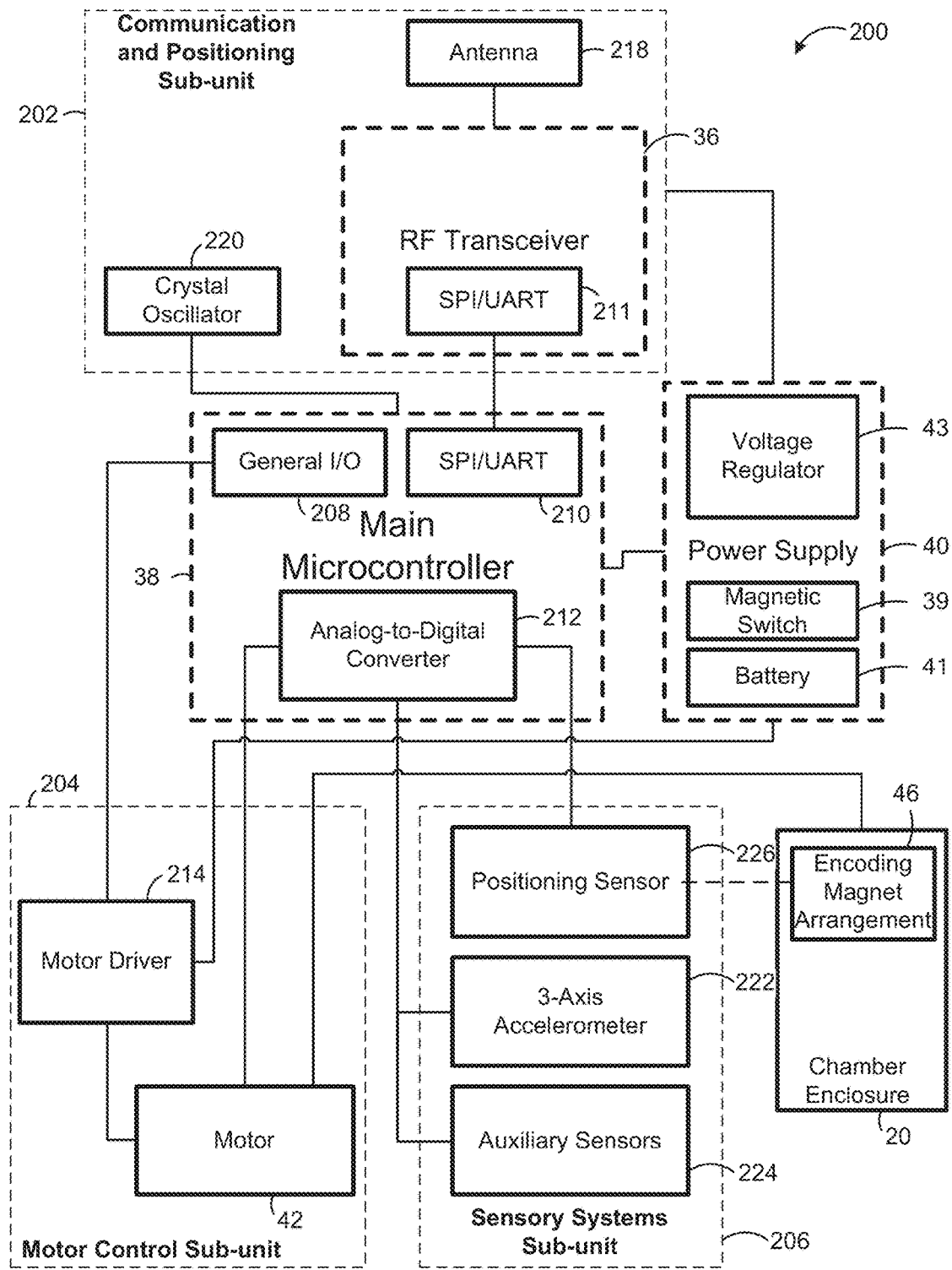
FIG. 4 is a block diagram of the electrical components of the ingestible medical device of FIG. 1.

Referring now to FIG. 4, shown therein is a block diagram 200 of the electrical components of the ingestible medical device 10 including the main microcontroller 38, the power supply 40, the chamber enclosure 20, a communication and positioning sub-unit 202, a motor control sub-unit 204, and a sensory systems sub-unit 206.

As described above, the main microcontroller 38 includes programming, control and memory circuits for holding and executing firmware and coordinating all functions of the ingestible medical device 10 and the other peripherals embedded on the main PCB 32. The main microcontroller 38 includes, at least, a general input/output (I/O) interface 208, a SPI or a Universal Asynchronous Receiver/Transmitter (UART) interface 210, and an Analog-to-Digital Converter (A/D Converter) 212. The main microcontroller 38 may consider the A/D Converter 212 to be a peripheral device.

The general I/O interface 208 includes a fixed number of general input/output pins (GPIOs). These GPIOs may be grouped into groups of two or three pins for implementing a variety of communication protocols, such as for example Single-Wire Interface (SWI), a two-wire interface (e.g., an Inter-Integrated Circuit or I$^2$C) and/or SPI. The groups of GPIOs that are delegated to these communication protocols may serve as a bus for connecting the main microcontroller 38 with one or more peripheral devices. For example, the main microcontroller 38 may connect to a motor driver 214 such as a Dual Full Bridge Driver, (as illustrated in the motor control sub-unit 204) via a group of GPIOs.

Using any of the above listed communication protocols, the main microcontroller 38 may send a series of requests to addresses associated with specific groups of GPIOs for detecting which peripheral devices, if any, are present on the bus. If any of the peripheral devices are present on the bus, the peripheral device that is present returns an acknowledging signal to the main microcontroller 38 within a designated time frame. If no response is received within this designated time frame, the peripheral device is considered absent.

The SPI/UART interface 210 is used for communicating with an SPI/UART interface 211 located on the transceiver 36. Also, the A/D Converter 212 is coupled with the motor 42 in the motor control sub-unit 204 and any of the sensors in the sensory systems sub-unit 206. For example, the A/D Converter 212 may allow for measurement of an amount of current drawn by the motor 42.

The communication and positioning sub-unit 202 includes an antenna 218, a crystal oscillator 220 and the RF transceiver 36. In some embodiments, the ingestible medical device 10 can communicate by infrared, in which case an IR-sensitive phototransistor and a resistor coupled to the A/D converter 212 are included in the communication and positioning sub-unit 202. Each of these components has been described in detailed above with reference to FIG. 3A. As described above, communication between the ingestible medical device 10 and the base station generally requires use of the antenna 218, the crystal oscillator 220 and the RF transceiver 36.

The RF transceiver 36 is considered to be a peripheral device to the main microcontroller 38. Therefore, the main microcontroller 38 may initiate RF communications by sending the RF transceiver 36 data specifying the channel on which the RF transceiver 36 is to transmit, power, frequency, and other parameters that are required for RF communication as well as data that is specific to the operation of the ingestible medical device 10.

In some embodiments, the communication and positioning sub-unit 202 may also enable determination of a position of the ingestible medical device 10 inside a body. Generally, the position of the ingestible medical device 10 may be determined from a triangulation based on the relative signal intensity from a signal transmitted between the ingestible medical device 10 and one or more external transmitters. The one or more external transmitters may serve as reference points in a Cartesian coordinate system. The signals that are triangulated may be electromagnetic (EM) or acoustic (e.g., with the use of a MEMs microphone).

The sensory systems sub-unit 206 generally includes one or more sensors. Example sensors include a positioning sensor 226, such as a hall-effect sensor 64 or the optical encoder 1406, a three-axis accelerometer 222 and one or more auxiliary sensors 224. As illustrated in FIG. 4, the positioning sensor 226 is a magnetic sensor that operates in conjunction with the encoding magnet arrangement 46. Various combinations of auxiliary sensors 224 can be included in various embodiments to expand the functionality of the ingestible medical device 10. For example, the auxiliary sensors 224 may include at least one environmental sensor (e.g., a pH level sensor such as an ISFET, a field-effect biosensor (BioFET), a temperature sensor such as RTD, piezoelectric systems, an optical sensor, etc.) that will interface with the ingestible medical device 10 primarily through instrumentation amplifiers and extra channels of the A/D Converter 212.

The auxiliary sensors 224 may also be used for determining a position of the ingestible medical device 10 inside the body of the subject. In this case, the auxiliary sensors 224 can be used in combination with the communication and positioning sub-unit 202. The auxiliary sensors 224 can provide supplemental information regarding the environment within the body. The supplemental information may be used for triggering an operation of the ingestible medical device 10, such as whether to trigger an internal timer of the ingestible medical device 10. Generally, the ingestible medical device 10 moves within the body at a variable speed but the ingestible medical device 10 moves at a less variable pace when it is inside the small intestine. Therefore, the supplemental information provided by the auxiliary sensors 224 can be used to more accurately determine if the ingestible medical device 10 is inside the small intestine. Once inside the small intestine, the operation of the ingestible medical device 10 can be triggered in accordance with time.

As described above, the auxiliary sensors 224 may include one or more environmental sensors, such as a pH level sensor, a light sensor, an impedance sensor, a temperature sensor and/or a capacitance sensor. The supplemental information provided from the auxiliary sensors 224 can be used alone and/or in combination for determining a position of the ingestible medical device 10 inside the body.

Figure 15B:
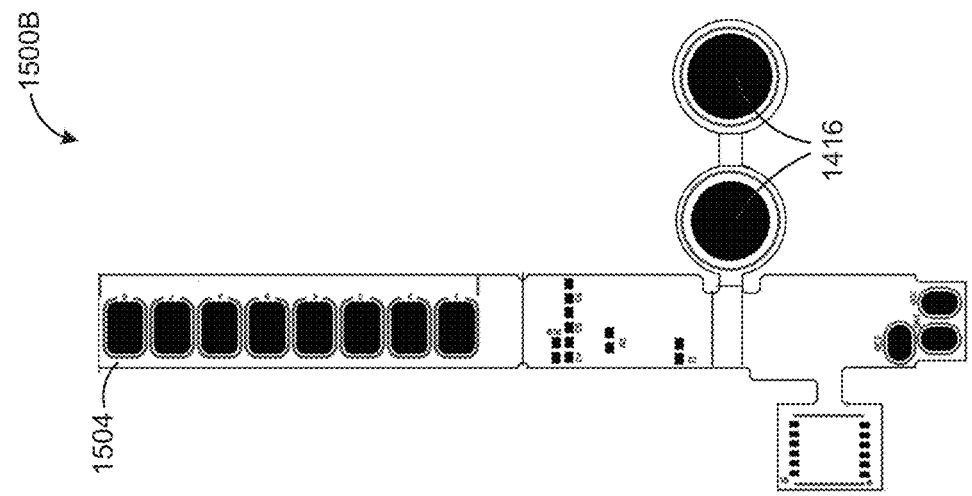
FIGS. 15A and 15B are block diagrams of a flexible PCB in another example embodiment.
Figure 15A:
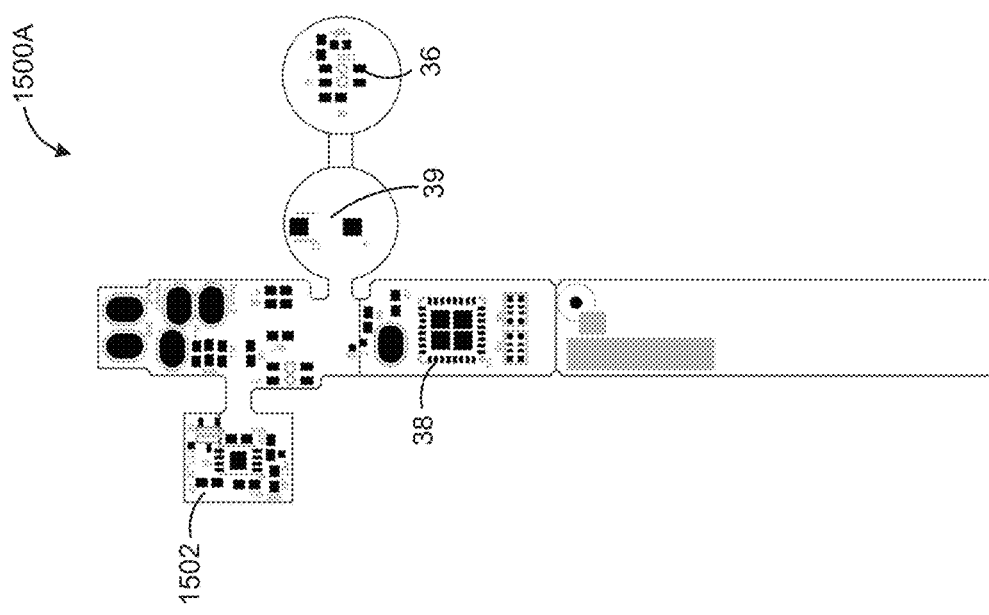

Reference is now made to FIGS. 15A and 15B, illustrated therein are a front view 1500A and a rear view 1500B, respectively, of a main PCB 1500 that incorporates several environmental sensors in accordance with an example embodiment. It will be understood that other environmental sensors may similarly be included in the main PCB 1500. The main PCB 1500 is a flexible PCB that can be used in a sensing probe. The main microcontroller 38 provided on the main PCB 1500 includes multiple capacitive sensing input channels for receiving sensor data from the capacitance sensor 1504 provided on the main PCB 1500.

As illustrated in FIG. 15A, the main PCB 1500A can include a pH level sensor 1502.

The pH level sensor 1502 can provide supplemental information for locating the ingestible medical device 10 because the acidity variation along the gastrointestinal tract is generally well characterized. For example, after the ingestible medical device 10 travels through the pyloric sphincter, the acidity level would decrease drastically causing the pH level to rise indicating that the ingestible medical device 10 has entered the small intestine. The pH level sensor 1502 may be implemented by an ISFET, which can cause a measurable cascade of electrons when exposed to various concentrations of hydrogen ions.

Figure 16:
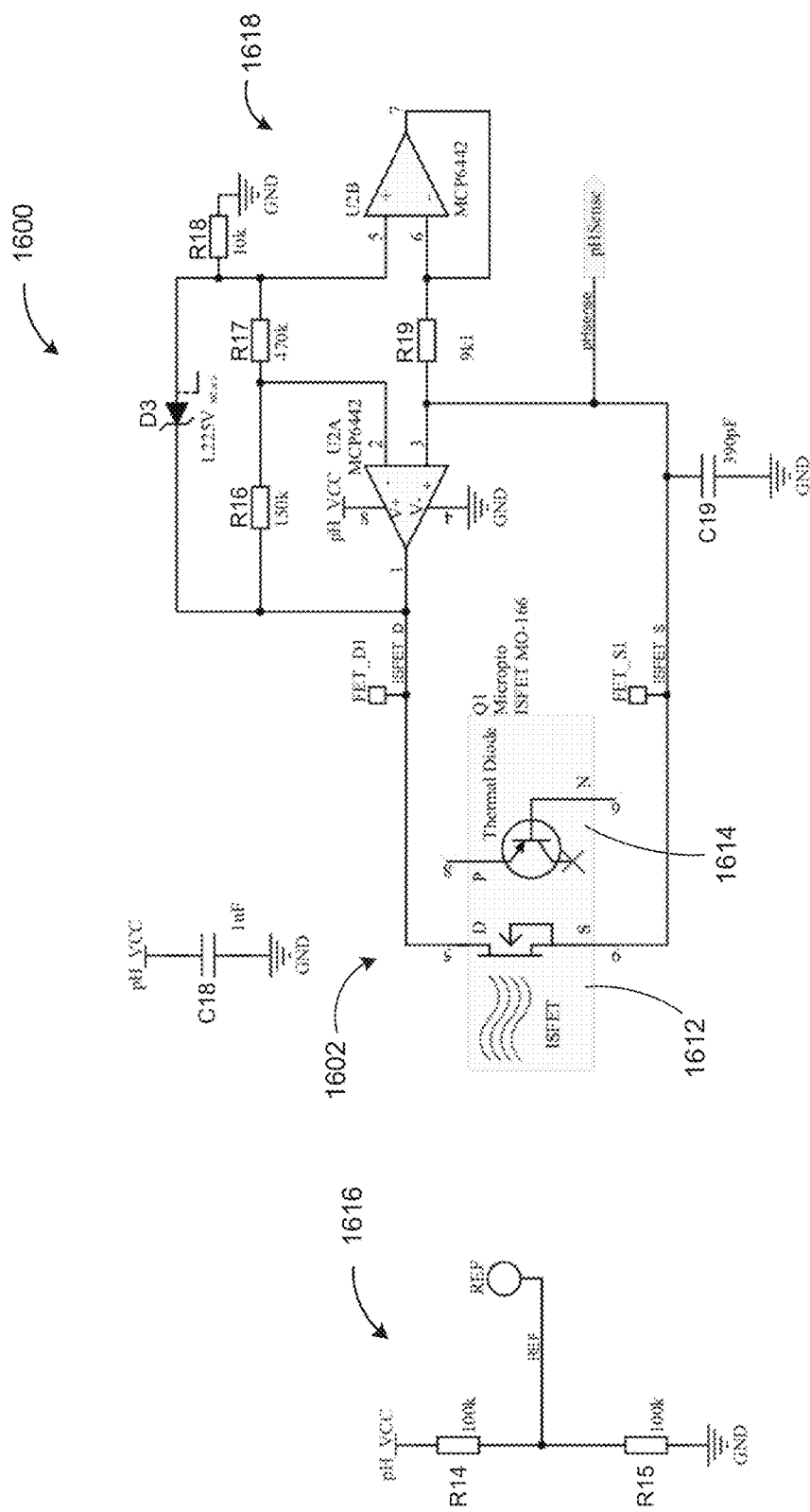
FIG. 16 is an example circuit design of a pH level sensor in an example embodiment.

A schematic circuit diagram 1600 of an example pH level sensor 1502 is generally illustrated in FIG. 16.

In the circuit diagram 1600, an ISFET 1602 shares a power connection and a ground connection with a main circuit of the ingestible medical device 10. The main circuit is generally the circuit on which the microcontroller 38 is provided.

The circuit diagram 1600 also includes a contact region 1612 that can come into contact with fluid and is sensitive to hydrogen ions. The ISFET 1602 generally operates as a field effect transistor that is sensitive to the presence of hydrogen ions. A gate of the ISFET 1602 allows for electrons to pass when the ISFET 1602 is in the presence of hydrogen ions. The flow or cascade of electrons, or the current, at the gate of the ISFET 1602 can be approximately proportional to the concentration level of the hydrogen ions. However, the cascade of electrons is generally not linearly proportional to the concentration level of hydrogen ions. Instead, the cascade of electrons can be affected by temperature variations. The circuit diagram 1600, therefore, also includes a temperature diode 1614 for correcting any temperature variations.

The circuit diagram 1600 also includes a reference electrode 1616. The reference electrode 1616 provides a reference potential to be compared with a potential generated by the cascade of electrons. The output signal from the ISFET 1602 is amplified through an amplifier sub-circuit 1618 comprising of one or more operational amplifiers.

The A/D Converter 212 receives the signal from the ISFET 1602 for determining the concentration level of the hydrogen ions and therefore, the surrounding environment of the ingestible medical device 10. The A/D Converter 212 may receive the output signal from the ISFET 1602 via one or more operational amplifiers, such as the amplifier sub-circuit 1618 described above. The A/D Converter 212 may receive the output signal from the ISFET 1602 via a pH level sensor input terminal on the main microcontroller 38.

Example values for components R14 to R19, C18, C19 and D3 of FIG. 16 are provided in Table 2, below.

TABLE 2

Example Electronic Component Values for FIG. 16

| Components | Range |
| --- | --- |
| R14 | 100 kΩ |
| R15 | 100 kΩ |
| R16 | 150 kΩ |
| R17 | 470 kΩ |
| R18 | 10 kΩ |
| R19 | 9 kΩ |
| C18 | 1 nF |
| C19 | 390 pF |
| D3 | 1.225 V |

In embodiments that use a light sensor (not shown), the light sensor includes one or more sets of LED emitter and receiver components that are evenly distributed around the ingestible medical device 10. The light sensor may provide measurement data for indicating whether the ingestible medical device 10 is inside the stomach, the pyloric sphincter or the small intestine. In particular, the light sensor is likely to provide more inconsistent measurement data when the ingestible medical device 10 is inside the stomach than when the ingestible medical device 10 is inside the small intestine because the ingestible medical device 10 is more physically constrained when it is inside the small intestine.

In embodiments that use an impedance sensor (not shown), the impedance sensor includes electrodes for measuring a current in the surrounding environment. For example, an exterior surface of the ingestible medical device 10 may include two or more electrodes. A known voltage is applied to one of the electrodes while the other electrode is used to measure the current being conducted in the surrounding environment. The electrodes may be circular in shape and located on a circumferential region on the ingestible medical device 10. Other shapes and particular locations for the electrodes can be used in other embodiments. Unlike the capacitance sensor described below, the operation of the impedance sensor is not limited by the charge time of a capacitor component and therefore, the impedance sensor generally has a higher data acquisition rate than the capacitance sensor.

Referring again to FIG. 15B, the main PCB 1500B can include a capacitance sensor 1504. The capacitance sensor 1504 may be an array of one or more capacitance sensing terminals. Each of these capacitance sensing terminals can be connected to at least one of the capacitive sensing input channels of the main microcontroller 38.

Figure 17:
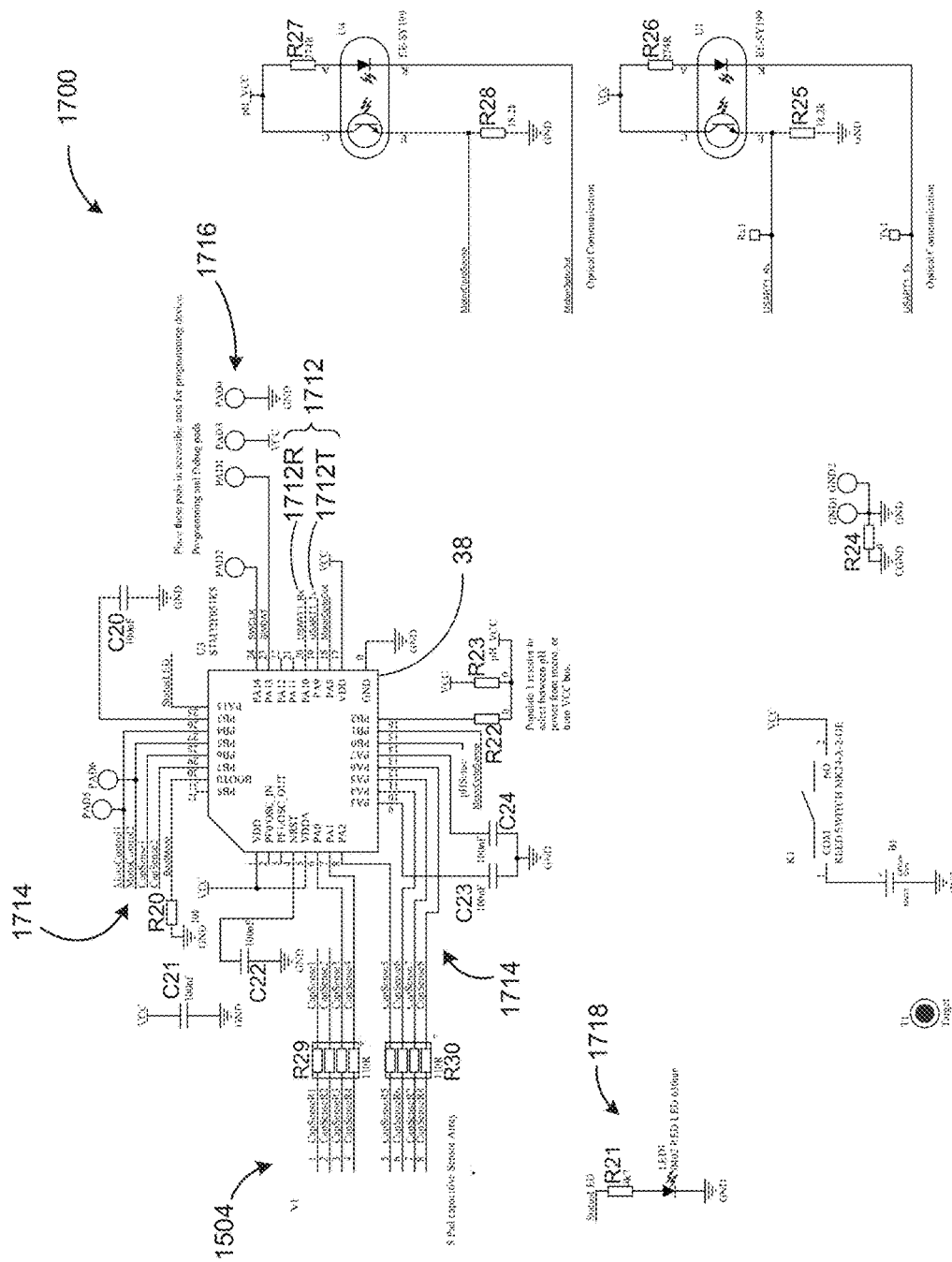
FIG. 17 is an example circuit design of the flexible PCB of FIG. 15B.

A schematic circuit diagram 1700 for another example embodiment of the main PCB 32 is generally illustrated in FIG. 17. Unlike the embodiments of the main PCB 32 described above with reference to FIGS. 7A to 7D, the circuit diagram 1700 includes the capacitive sensor 1504.

Also, the main microcontroller 38 in the circuit diagram 1700 is a 32-bit microcontroller with eight capacitive sensing channels, shown generally at 1714, and a hardware UART port 1712 with a receiving terminal 1712R and a transmitting terminal 1712T.

In some embodiments, the UART is implemented using an IR emitter and an IR receiver. For example, the receiving terminal 1712R is connected to the IR receiver and the transmitting terminal 1712T is connected to the IR emitter.

The capacitive channels 1714 connect to corresponding capacitive sensor terminals, such as the capacitive sensors 1504 located on the rear view 1500B of the flexible PCB 1500. The main microcontroller 38 can then measure a capacitance of the surrounding environment based on sensor information received via the capacitive channels 1714.

In this case, the circuit diagram 1700 also includes a programming array 1716 of pads or terminals. The programming array 1716 can receive instructions or a program to be stored, or burned, onto the main microcontroller 38. The programming array 1716 may not be necessary if the main microcontroller 38 is programmed during manufacturing but prior to being attached to the main PCB 32.

The circuit diagram 1700 further includes an indicator LED 1718 for providing visual feedback during operation. The circuit diagram 1700 also includes one or more pull-up resistors and pull-down resistors to ensure stable logic within the main PCB 32, and one or more capacitors for acting as a bulwark against rapid fluctuations in power.

Example values for the components C20 to C24 and R20 to R30 of FIG. 17 are provided in Table 3, below.

TABLE 3

Example Electronic Component Values for FIG. 17

| Components | Range |
| --- | --- |
| C20 | 100 nF |
| C21 | 100 nF |
| C22 | 100 nF |
| C23 | 100 nF |
| C24 | 100 nF |
| R20 | 10 kΩ |
| R21 | 4.7 kΩ |
| R22 | 0 Ω |
| R23 | 0 Ω |
| R24 | 0 Ω |

TABLE 3-continued

Example Electronic Component Values for FIG. 17

| Components | Range |
|---|---|
| R25 | 18.2 kΩ |
| R26 | 270 Ω |
| R27 | 270 Ω |
| R28 | 18.2 kΩ |
| R29 | 110 Ω |
| R30 | 110 Ω |

The capacitance sensor 1504 can provide supplemental information for positioning the ingestible medical device 10 by detecting and measuring any perturbation of an electrical field within a dielectric material. The capacitance sensor 1504 may be located around an inner circumference of the ingestible medical device 10 so that the capacitance sensor 1504 can more readily measure a capacitance of the environment immediately external to the ingestible medical device 10. The variation of the structure of the stomach, the small intestine and the large intestine can affect the capacitance measured by the capacitance sensor 1504 as the ingestible medical device 10 travels through the body.

Based on at least capacitance measurements captured by the capacitance sensor 1504, the main microcontroller 38 can determine a position of the ingestible medical device 10. It was determined that capacitance measurements inside the stomach are generally erratic whereas capacitance measurements inside the small intestine may be affected by the rhythmic muscular contractions associated with peristalsis. That is, the rhythmic muscular contractions inside the small intestine are generally associated with a characteristic and quasi-periodic duration and therefore, associated with a high frequency and bimodal oscillation. Accordingly, the main microcontroller 38 can process the capacitance measurements and determine whether the measured capacitance corresponds to a pattern associated with capacitance measurements that are expected within the small intestine. In an example embodiment, the main microcontroller 38 includes an accumulator component for maintaining an operational count.

The operational count may include a first and a second accumulator count. The first accumulator count is a count of a number of factors that indicate a positive transition into the target location. The second accumulator count is a total energy caused by muscular contractions and can generally correspond to capacitive values. As described above, the main microcontroller 38 can measure capacitance at an exterior of the ingestible medical device 10 as muscle contracts and relaxes around the ingestible medical device 10. When the second accumulator count reaches a predetermined energy threshold, the second accumulator count can also be included into the first accumulator count. Therefore, the operational count can be rapidly increased with the combination of the first and the second accumulator counts. Generally, a high operational count indicates a high likelihood that the ingestible medical device 10 has reached the target location.

It should be noted that there can be embodiments which use a particular combination of the light sensor, pH level sensor, impedance sensor, temperature sensor and capacitance sensor and corresponding algorithms that incorporate measurements from these sensors to more accurately determine the location of the ingestible medical device 10.

Figure 18:
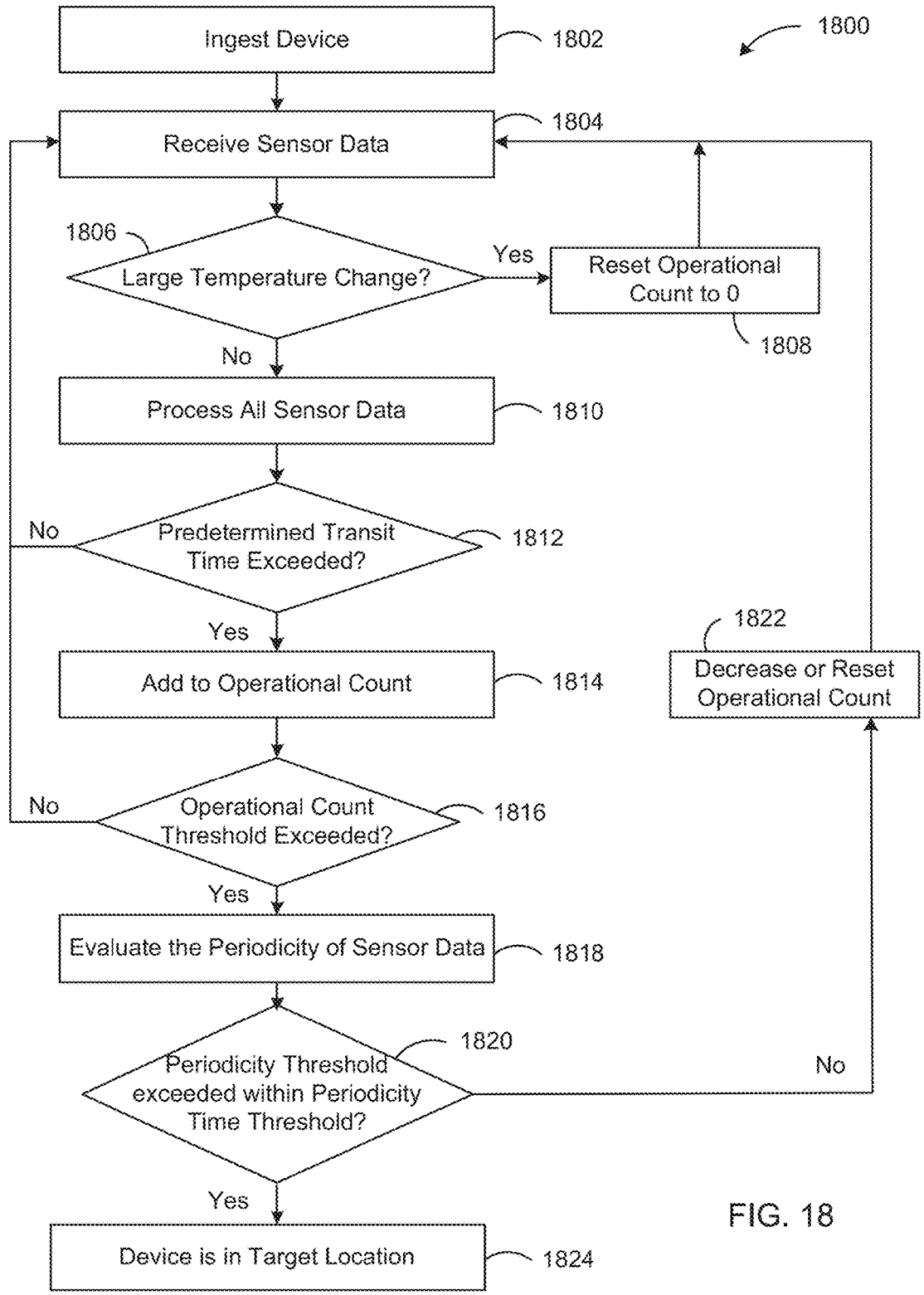
FIG. 18 is a flowchart of an example embodiment of an operation of the ingestible medical device.

In some embodiments, supplemental information measured by other auxiliary sensors 224 can be used in combination with the capacitance measurements. A flowchart 1800 illustrating an example method for determining a position of the ingestible medical device 10 using supplemental information provided by the auxiliary sensors 224 is generally illustrated in FIG. 18.

After the ingestible medical device 10 is ingested into the body at 1802, the auxiliary sensors 224 operate to capture and retrieve sensor data at 1804.

At 1806, the method 1800 involves determining whether a large temperature change has occurred. For example, the capacitance sensor 1504 can be reset if data captured by the temperature sensor exceeds a threshold value. The stomach is susceptible to significant changes in temperatures. Therefore, when a significant increase or decrease in temperature is detected by the temperature sensor at 1806, the method 1800 may determine that the ingestible medical device 10 is still inside the stomach despite any capacitance measurements provided by the capacitance sensor 1504. The method 1800 then involves resetting the accumulator component to zero (at 1808). Otherwise, the method 1800 proceeds to 1810 to process the sensor data received from the other auxiliary sensors 224.

At 1812, the method 1800 determines whether a predetermined minimum transit time is exceeded. The predetermined minimum transit time is an estimated time that the ingestible medical device 10 will take to reach the target location. The ingestible medical device 10 may include an internal timer for tracking an initial transit time and a target transit time. The initial transit time indicates an amount of time before the ingestible medical device 10 reaches the target location. The target transit time indicates an amount of time that has passed since the ingestible medical device 10 reached the target location. If the method 1800 determines that the initial transit time has exceeded the predetermined transit time period, the operational count, or specifically the first accumulator count, maintained by the accumulator component is increased at 1814. Otherwise, the auxiliary sensors 224 continue to collect data at 1804.

At 1816, the method 1800 determines whether an operational count threshold is exceeded. If the operational count threshold is exceeded, the periodicity of the sensor data is determined at 1818. Otherwise, the auxiliary sensors 224 continue to collect data at 1804.

The periodicity of the sensor data may also be considered in determining a position of the ingestible medical device 10 (at 1820). For example, when the ingestible medical device 10 is inside the small intestine, the transitions in the capacitance signal sensed by the capacitance sensors 1504 should occur at approximately the same frequency for a given amount of time. For example, mathematical techniques, such as variations of the Fourier Transform, can be applied to the sensor data for determining a concentrated capacitance signal or a high power density at specific frequencies. If the method 1800 identifies a concentrated capacitance signal in the sensor data that exceeds a periodicity threshold within a predetermined periodicity time threshold (at 1824), the sensor data can be considered stationary and periodic, and the method 1800 determines that the ingestible medical device 10 is inside the small intestine. Otherwise, the operational count is reset to zero or decreased (at 1822) since inaccurate sensor data was captured and therefore, the auxiliary sensors 224 continue to collect data at 1804. The predetermined periodicity time threshold is a time period within which the capacitance signal needs to meet the periodicity threshold before the periodicity threshold can be considered to be exceeded.

The power supply 40 comprises the magnetic switch 39 as well as a battery 41 and a voltage regulator 43. The magnetic switch 39 and battery 41 have been previously described. As described above, the battery 41 can comprise of one or more different types of battery cell groups for providing different amount of power to the different components of the ingestible medical device 10. The voltage regulator 43 provides a relatively constant voltage to the components of the ingestible medical device 10 that require power. Various designs can be used for the voltage regulator 43 as is commonly known by those skilled in the art.

As briefly described above, the position encoder sub-unit and the main microcontroller 38 operate together to determine a location of the access port 24 relative to each of the chamber openings 22. The position encoder sub-unit may include a magnetic sensor or an optical encoder 1406.

When the magnetic sensor is used for determining a location of the access port 24, an encoding magnet arrangement 46 is also included in the ingestible medical device 10. As a magnet 46m in the encoding magnet arrangement 46 rotates over the sensor 64, the sensor 64 senses the magnet 46m and generates a corresponding positioning signal, which can be a quasi-sinusoidal or square wave depending on the particular implementation.

In embodiments in which the number of magnets 46m used in the encoding magnet arrangement 46 is fewer than a total number of open and closed states in one revolution of the chamber enclosure 20, or there are fewer than two magnets 46m for each chamber 18, the sensor 64 senses a strength of the magnetic signal and generates a positioning signal whose amplitude corresponds with the sensed strength of the magnetic signal. This may generally be referred to as an analog positioning technique.

In the analog positioning technique, the main microcontroller 38 may determine a current position of the access port 24 from a look-up table using the sensed strength of the magnetic signal and a previous angular position of the sensed magnet. In some embodiments, in which more than one magnet 46m is used in the encoding magnet arrangement 46 during the analog positioning technique, the main microcontroller 38 maintains a count of the number of magnets 46m that passes the sensor 64 or the number of peaks in the positioning signal. As the chamber enclosure 20 continues to rotate, firmware on the main microcontroller 38 maintains a count of the number of magnets (i.e. a magnet count) that passes the sensor 64. The magnet count increments for each peak value in the positioning signal that is received by the main microcontroller 38. Based on the positioning signal, the magnet count, and the previous angular position, the main microcontroller 38 can determine a location of the access port 24 with respect to each of the chamber openings 22.

The look-up table correlates the amplitude of the positioning signal with an angular position of the access port 24. The angular position of the access port 24 may also include directionality information. For example, the angle increases when the chamber enclosure 20 moves in one direction, such as a clockwise direction, and the angle decreases when the chamber enclosure 20 moves in another direction, such as a counter-clockwise direction. A current location of the access port 24 may then be determined based on a direction of rotation for the access port 24 and by comparing a current angular position with a previous angular position that is stored in memory. The look-up table may be generated by the ingestible medical device 10 and/or programmed into the ingestible medical device 10 during calibration.

A degree of accuracy, or a resolution, at which the access port 24 may be positioned over a chamber opening 18 or an area between the chamber openings 18 may be limited by the number of bits of the A/D Converter 212 of the main microcontroller 38. The resolution may be determined from the ratio of a revolution of the chamber enclosure 20 (e.g.,) $360°$ to $2^{(Number\ of\ Bits\ in\ A/D\ Converter)}$.

Figure 5:
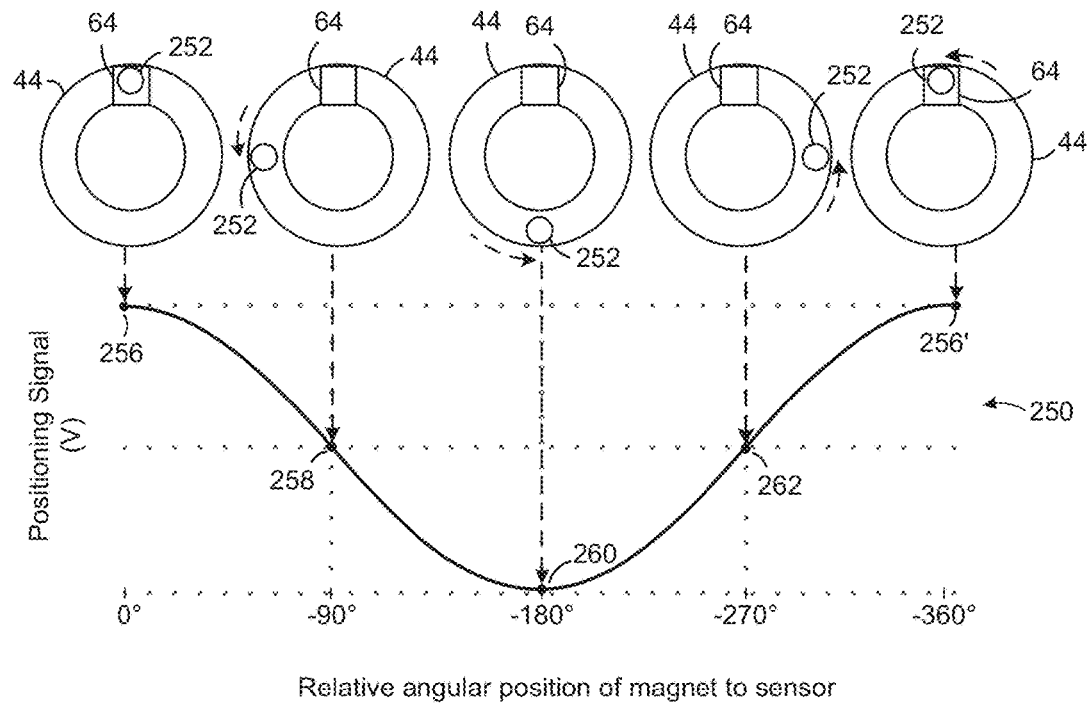
FIG. 5 is a plot of a positioning signal generated by a sensor during rotational operation of the ingestible medical device in one example embodiment.

Referring now to FIG. 5, illustrated therein is a positioning signal 250 generated by the sensor 64, in accordance with an example embodiment. In this embodiment, one magnet 252 is used in the encoding magnet arrangement 46 and a sinusoidal waveform is generated in the positioning signal 250.

For ease of exposition, the magnet 252 is illustrated as it rotates with the chamber enclosure 20 (not shown) over the secondary PCB 44 which is stationary. Similarly, only the sensor 64 is illustrated on the secondary PCB 44. As illustrated in FIG. 5, the magnet 252 rotates in a counter-clockwise direction and thus, the relative angular position of the magnet 252 decreases as the magnet 252 rotates toward the sensor 64. Also, the relative angular position is denoted as a negative value to represent that the magnet 252 is rotating in a counter-clockwise direction.

When the relative angular position of the magnet 252 is 0° or −360°, the magnet 252 is aligned with the center of the sensor 64 so that the sensor 64 senses the strongest magnetic signal from the magnet 252 and thus, the sensor generates the largest amplitude 256 and 256', respectively, in the positioning signal 250. As the magnet 252 rotates away from the sensor 64, the sensor 64 senses a decreasing magnetic strength from the magnet 252 and thus, the corresponding amplitude of the positioning signal 250 decreases. As the magnet 252 continues to rotate, the position of the chamber enclosure 20 relative to the sensor 64 can be determined by comparing a current angular position of the magnet 252 with a previous angular position of the magnet 252. For example, as shown in FIG. 5, it is determined, from the look-up table, that the current amplitude 258 of the positioning signal corresponds to an angular position of −90° since the magnet 252 is rotating in a counter-clockwise direction and the previous angular position is 0°. Similarly, the subsequent amplitude 260 of the positioning signal 250 is determined, from the look-up table, to correspond with an angular position of −180°. However, after passing the relative angular position of −180°, the magnet 252 becomes gradually closer in distance to the sensor 64 and the corresponding magnetic strength, thus, also increases. Accordingly, the amplitude 262 is determined, from the look-up table, to correspond with a relative angular position of −270° since the magnet 252 is rotating in a counter-clockwise direction and the previous angular position is −180°.

In alternative embodiments, a digital positioning technique can be used. In these cases, the number of magnets 46m used in the encoding magnet arrangement 46 is equal to or greater than a total number of open and closed states in one revolution of the chamber enclosure 20 with a distribution that depends on the configuration of the chambers 18. For example, there can be at least two magnets 46m for each chamber 18. In these cases, the sensor 64 senses a magnet 46m within a range of the sensor 64 and generates a positioning signal that corresponds with a location of the sensed magnet 46m relative to the sensor 64 but has a different waveform compared to the previously described positioning signal.

When a magnet 46m is completely aligned with the sensor 64 (e.g., the magnet 46m overlaps the sensor 64), the sensor 64 senses a large magnetic strength from the relative position of the encoding magnet 46m with respect to the sensor 64 and generates a corresponding "high" value in the positioning signal (e.g., a peak on a quasi-sinusoidal or square wave). However, when one of the magnets 46m is not completely aligned with the sensor 64 (e.g., one of the magnets 46m may be near but not overlap the position of the sensor 64), the sensor 64 senses a lower magnetic strength from the relative position of the encoding magnet 46m with respect to the sensor 64 and generates a corresponding "low" value in the positioning signal (e.g., a trough on a quasi-sinusoidal or square wave). The sensor 64 transmits the positioning signal to the main microcontroller 38. In other words, the digital positioning technique operates in an "all-or-nothing" manner. The sensor 64 either generates a "high" value when it is aligned with a magnet 46m or a "low" value when it is not aligned with a magnet 46m. However, there can be other embodiments in which the sensor operates in the opposite manner with respect to the positioning of the magnet 46m with respect to the sensor in which case the signal is interpreted in the opposite manner but still provides the position information.

Since a "high" value (or a "peak") in the positioning signal is generated when one of the magnets 46m completely covers the sensor 64, the number of magnets that are used in the encoding magnet arrangement 46 directly corresponds with the number of peaks in the positioning signal (e.g., a frequency of the positioning signal). Accordingly, in one revolution of the chamber enclosure 20, the number of peaks in the positioning signal increases with each additional magnet that is included in the encoding magnet arrangement 46.

A degree of accuracy or a resolution, at which the access port 24 may be positioned over a chamber opening 22 or an area between adjacent chamber openings, may be determined from a ratio of a revolution of the chamber enclosure 20 (e.g., 360°) to a corresponding number of peaks (or the number of magnets in the encoding magnet arrangement 46) in the positioning signal. For example, if six magnets are used in the encoding magnet arrangement 46, the resolution is 60° (e.g., 360°/6).

As described above, the magnet 46m on the encoding magnet arrangement 46 that is aligned with the sensor 64 when the ingestible medical device 10 is first initialized (e.g., when all chamber openings 22 on the ingestible medical device 10 are sealed) is referred to as a primary magnet 46p. The primary magnet 46p serves as a reference point for determining a location of the access port 24 in relation to the chamber openings 22.

As the chamber enclosure 20 continues to rotate, firmware on the main microcontroller 38 maintains a count of the number of magnets (i.e. a magnet count) that passes the sensor 64. The magnet count increments for each "high" value in the positioning signal that is received by the main microcontroller 38. Based on the positioning signal, the magnet count and a position of the primary magnet 46p relative to the magnet currently positioned near the sensor 64, the main microcontroller 38 can determine a location of the access port 24 with respect to each of the chamber openings 22.

For example, assume there are three chamber openings 22, there are 6 magnets designated as magnets 1 to 6 and there are six angular positions as 1' to 6'. The angular positions 1', 3', and 5' are OPEN positions in which the access port 24 is aligned with one of the chamber openings 22 and the positions 2', 4', and 6' are CLOSED positions in which the access port 24 is not aligned with any of the chamber openings 22. Assuming that magnet 1 corresponds with the location of the access port 24 and starts in position 1', the main microcontroller 38 counts one to move the magnet 1 into position 2'. When the magnet 2 is in front of the sensor 64 at position 1', then it must mean that the magnet 1 is now in position 2'. When the magnet 3 is in the position 1' then magnet 1 must be at the position 3', which is the next CLOSED position and so on and so forth. However, in practical use, the ingestible medical device 10 should start in a closed position (i.e. the access port 24 is not aligned with any of the chamber openings 22), which means that the ingestible medical device 10 starts in the position 2' or the position 6' according to the example just given.

Figure 6:
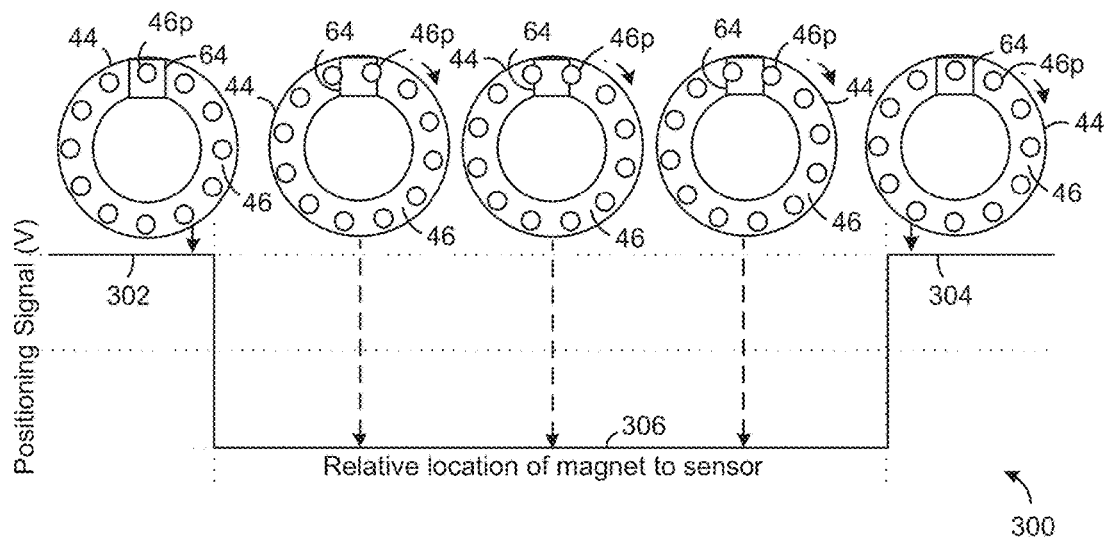
FIG. 6 is a plot of another positioning signal generated by a sensor during rotational operation of the ingestible medical device in another example embodiment.

With reference now to FIG. 6, illustrated therein is a positioning signal 300 that is generated by the sensor 64 when there are multiple magnets in the encoding magnet arrangement 46. For ease of exposition, only the magnets 46m (e.g., twelve magnets) in the encoding magnet arrangement 46 are illustrated as they rotate over the secondary PCB 44. Similarly, on the secondary PCB 44, only the sensor 64 is illustrated. The storage sub-unit 16 in this example includes three chambers 18.

As illustrated in FIG. 6, the encoding magnet arrangement 46 rotates in a clockwise direction. As described above, when a magnet 46m in the encoding magnet arrangement 46 is aligned with a center of the sensor 64, the sensor 64 senses a large magnetic signal and generates a 'high' value in the positioning signal. For example, as illustrated in FIG. 6, the sensor 64 generates a 'high' value 302 in the positioning signal due to the encoding magnet 46p and another 'high' value 304 in the positioning signal due to the rotation of the encoding magnet 46m following the encoding magnet 46p. However, when a magnet 46m in the encoding magnet arrangement 46 is not aligned with the center of the sensor 64, the positioning signal 300 generated by the sensor 64 contains a 'low' value 306.

The magnet count stored in the firmware of the main microcontroller 38 is incremented by one for each high value (e.g., 302 and 304) in the positioning signal received by the main microcontroller 38 from the sensor 64. For example, in FIG. 6, the magnet count may be incremented by 1 when the high value 304 in the positioning signal is received since one magnet that is, the primary magnet 46p, has passed by the sensor 64. Thereafter, the main microcontroller 38 can then determine that the chamber enclosure 20 is aligned with another chamber opening when the sensor 64 generates a high value in the positioning signal 300 and the magnet count is 4 and 8. Similarly, the main microcontroller 38 can then determine that the chamber enclosure 20 is aligned with a non-recessed area on the storage sub-unit 16 when the sensor 64 generates a high value in the positioning signal 300 and the magnet count is 2, 6 and 10. Finally, when the magnet count is 3, 7, or 11, the chamber enclosure 20 partially covers a chamber opening and thus, the sensor generates a low value in the positioning signal 300.

Figure 19:
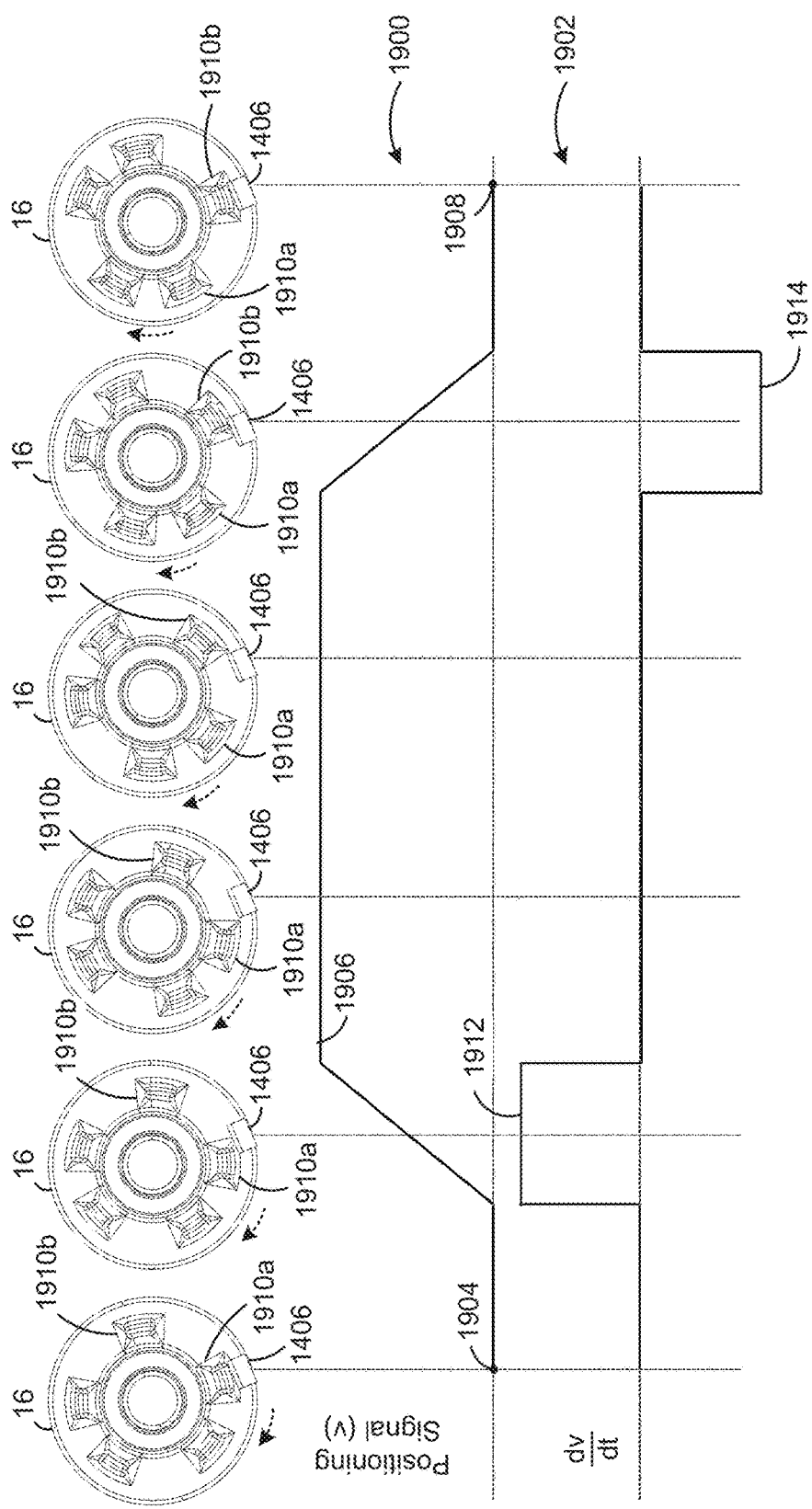
FIG. 19 is a plot of another positioning signal generated by a sensor during rotational operation of the ingestible medical device in another example embodiment.

Referring now to FIG. 19, illustrated therein is a positioning signal 1900 and a derivative signal 1902 that is the derivative of the positioning signal 1900 that is generated by the optical encoder 1406 when there are multiple optical markers 1910, such as protrusion members 1910a and 1910b, provided on the storage sub-unit 16. For ease of exposition, only the optical encoder 1406 is illustrated on the main PCB segment 1402. The storage sub-unit 16 in this example includes three chambers 18 but only two non-recessed areas. In this case, the storage sub-unit 16 includes two adjacent chambers.

As briefly described above, the optical encoder 1406 may be used instead of the magnetic encoder for determining a position of the access port 24. The optical encoder 1406 includes an IR emitter and receiver in this example embodiment although other implementations are possible in other embodiments. The optical encoder 1406 transmits an initial light signal towards the storage sub-unit 16 and detects a reflected light signal, or an amount of the initial light signal that is returned, from a portion of the storage sub-unit 16. The protrusion members 1910a and 1910b are positioned at certain locations on the surface of the storage sub-unit 16 relative to the location of the optical encoder 1406 to modulate the reflected light signal during operation.

As illustrated in FIG. 19, the protrusion members 1910 on the storage sub-unit 16 rotate in a clockwise direction. When a protrusion member 1910 is aligned with the optical encoder 1406, the optical encoder 1406 senses a large reflected signal and generates a 'low' value in the positioning signal 1900. For example, as illustrated in FIG. 19, the optical encoder 1406 generates a 'low' value 1904 in the positioning signal due to the protrusion member 1910a and another 'low' value 1908 in the positioning signal 1900 due to the location of the protrusion member 1910b following the protrusion member 1910a. However, when the protrusion member 1910a is not aligned with the optical encoder 1406, the positioning signal 1900 generated by the optical encoder 1406 increases to a 'high' value 1906.

Similar to the magnet count described above, an optical marker count may be stored and incremented by one for each low value (e.g., 1904 and 1908) in the positioning signal 1900 received by the main microcontroller 38 from the optical encoder 1406. For example, in FIG. 19, the optical marker count may be incremented by 1 when the low value 1904 in the positioning signal 1900 is received since one protrusion member, that is, the protrusion member 1910a, has rotated by the optical encoder 1406. Thereafter, the main microcontroller 38 can then determine that the access port 24 is aligned with another chamber opening when the optical encoder 1406 generates a low value in the positioning signal 1900 and the optical marker count is 3 and 5. Similarly, the main microcontroller 38 can then determine that the access port 24 is aligned with a non-recessed area on the storage sub-unit 16 when the optical encoder 1406 generates a high value in the positioning signal and the optical marker count is 2 and 4.

In some embodiments, the derivative signal 1902 is provided to the main microcontroller 38 instead of the positioning signal 1900. The derivative signal 1902 indicates a change in the positioning signal 1900 as well as a direction of the signal change. As illustrated in FIG. 19, a positive signal change, such as at 1912, can indicate that the protrusion member 1910a is moving away from the sensing region of the optical encoder 1406. A negative change, such as at 1914, can indicate that the protrusion member 1910b is moving towards the sensing region of the optical encoder 1406.

In embodiments in which the storage sub-unit 16 is the rotatable element, alternating light and dark regions may be used as the optical markers instead of the protrusion members 1910. The light and dark regions may be printed directly onto an outer surface of the motor 42.

Referring back to FIG. 4, the motor control sub-unit 204 includes the motor driver 214 and the motor 42. As described above, the motor driver 214 may be a Dual Full Bridge Driver that comprises a DPDT switch and protective circuitry including a resistor-diode combination in a single package. The main microcontroller 38 may control, based on the positioning signal sent from the sensor 64 on the secondary PCB 44, the amount of power delivered to the motor 42 through the Dual Full Bridge Driver 214. When the motor 42 receives power, it will rotate the chamber enclosure 20 by a distance corresponding to the received power. Since the encoding magnet arrangement 46 is embedded in the chamber enclosure 20, the encoding magnet arrangement 46 rotates with the chamber enclosure 20. When the magnets 46m rotate over the sensor 64, the sensor 64 senses a varying magnetic strength from the magnets 46m and encodes this information in the positioning signal which is then sent to the main microcontroller 38 through the A/D Converter 212.

The power supply 40 provides power directly to the main microcontroller 38 and the communication and positioning subunit 202. The power supply 40 provides power to the motor control sub-unit 204 via the motor driver 214, as described above.

Various circuit designs of the main PCB 32 and secondary PCB 44 are possible. Various example embodiments of circuit designs for the main PCB 32 are shown in FIGS. 7A to 7D and an example embodiment of a circuit design for the secondary PCB 44 is shown in FIG. 8. Generally, referring simultaneously to FIG. 4, the circuit designs for the main PCB 32 include the main microcontroller 38, a motor control sub-unit 204 (e.g., an analog high-current switch 214), a component for uploading software to the main microcontroller 38 (e.g., a chip burner 358 or a Flexibly Printed Circuit (FPC) connector 404), a magnetic ON/OFF/RESET switch 39, and a communications and positioning sub-unit 202 (e.g., RF Transceiver 36).

It will be understood that the component for uploading software to the main microcontroller 38 may vary according to design choice. The chip burner 358 is selected if only a few pins are required for transferring the software to the main microcontroller 38. The FPC connector 404, on the other hand, is preferred if more pins are required for programming the main microcontroller 38. Another advantage of the FPC connector 404 is that it can physically lock the programming cable into place so that debugging of the ingestible medical device 10 can be easier.

Figure 7A:
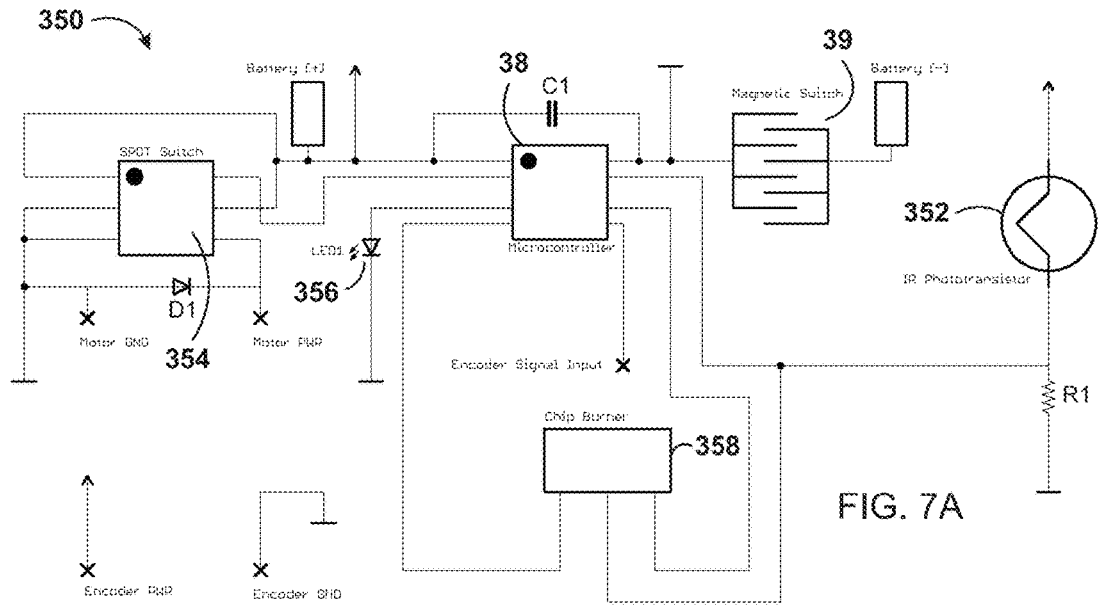
FIGS. 7A to 7D are example embodiments of circuit designs of a main printed circuit board (PCB) that can be used by the ingestible medical device.
Figure 8:
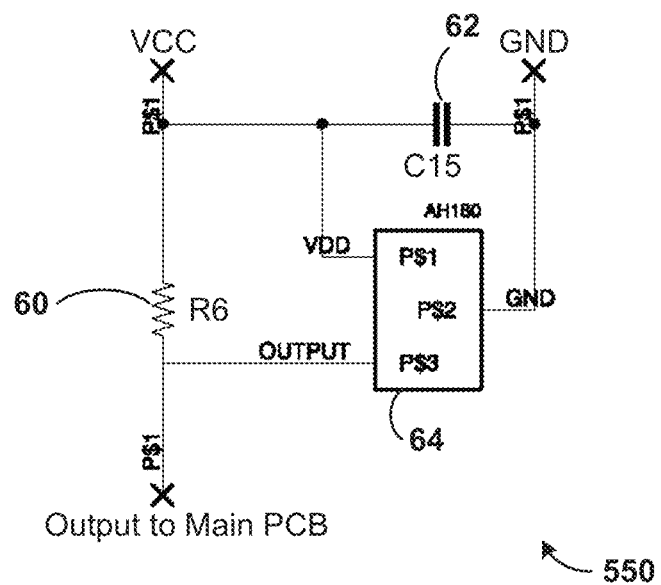
FIG. 8 is an example embodiment of a circuit design of a secondary PCB that can be used by the ingestible medical device.

FIG. 7A generally illustrates one example embodiment 350 of a circuit design of the main PCB 32. In this example embodiment, the main microcontroller 38 is a PIC12F1822 microcontroller, the communication sub-unit 202 includes an infrared phototransistor 352, and the intermediary device connecting the main microcontroller 38 to the motor 42 is a SPDT switch 354. The microcontroller 38 is protected by a single protective diode 356 which controls current directionality. A chip burner 358 is used for uploading software to the microcontroller 38. Since the SPDT switch 354 is used in this example embodiment, the motor 42 may move only in one direction. With the infrared phototransistor 352, instructions and/or operating parameters may be received from a base station via infrared programming once a software program is loaded into the microcontroller 38. The software program may be written in assembly language, which helps maximize the resources of the main microcontroller 38. Example values for the components C1, R1 and D1 of FIG. 7A are provided in Table 4, below.

TABLE 4

| Example Electronic Component Values for FIG. 7A | |
|---|---|
| Components | Range |
| R1 | 18.2 kΩ to 100 kΩ |
| C1 | 100 nF |
| D1 | 10 V to 40 V, 30 mA to 100 mA |

Figure 7B:
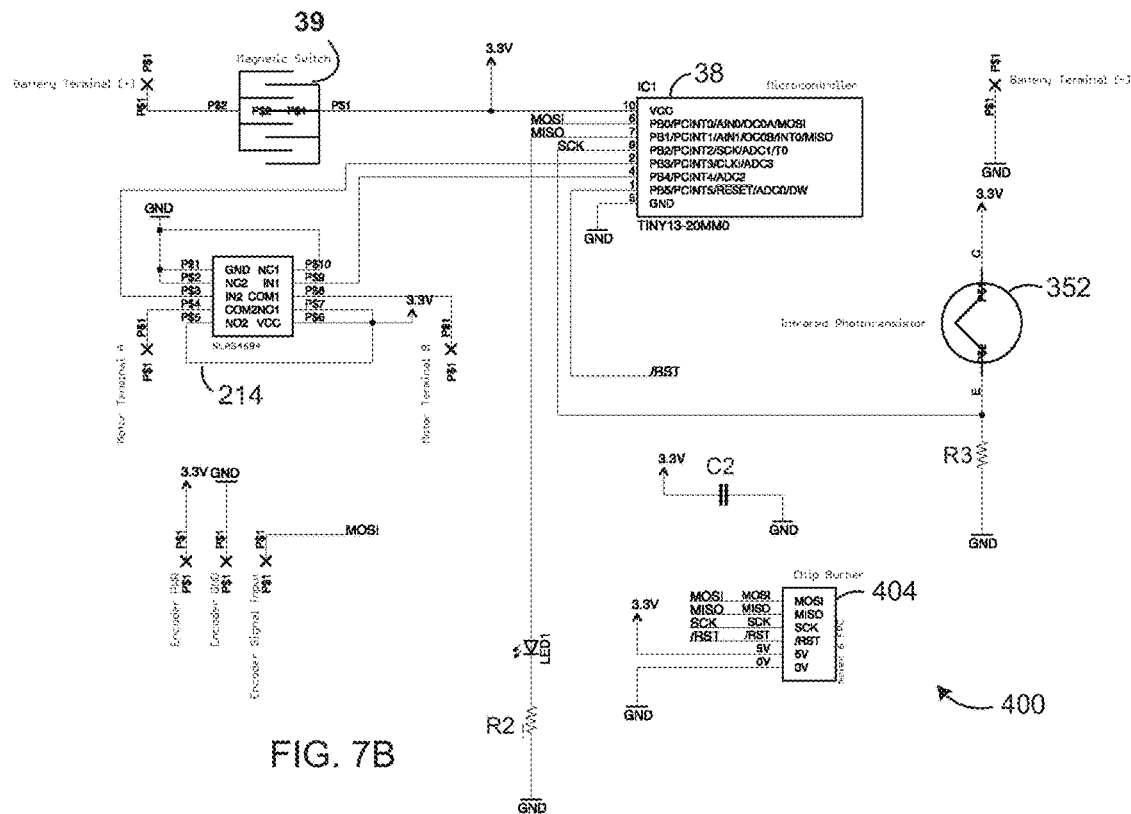

Referring now to FIG. 7B, generally illustrated therein is another example embodiment 400 of a circuit design of the main PCB 32. In this example embodiment, the main microcontroller 38 is the ATtiny13A microprocessor by ATMEL™, the communication sub-unit 202 includes an infrared phototransistor 352, and the intermediary device connecting the main microcontroller 38 to the motor 42 is a motor driver 214. It will be understood that the main microcontroller 38 may be selected from any microcontroller with similar operating characteristics and functions as in this example embodiment. As described above, the DPDT switch in the Dual Full Bridge Driver 214 enables the motor 42 to move in a bidirectional manner. In this example embodiment, the software program may be written in the C or C++ programming language, which provides for ease of use and improved portability, onto the main microcontroller 38. An FPC connector 404 is included into the circuit 400 for uploading software to the microcontroller 38. The circuit 400 also includes an LED 402 which is activated so that the ingestible medical device 10 is more easily identified when excreted from the body. The pins below the DPDT switch are used for the secondary PCB 44. The capacitor above the FPC connector 404 is used to couple the system voltage to the system ground to minimize fluctuations/noise in the circuit. Example values for the components R2, R3 and C2 of FIG. 7B are provided in Table 5, below.

TABLE 5

Example Electronic Component Values for FIG. 7B

| Components | Range |
| --- | --- |
| R2 | 30 Ω to 120 Ω |
| R3 | 100 kΩ |
| C2 | 100 nF |

Figure 7C:
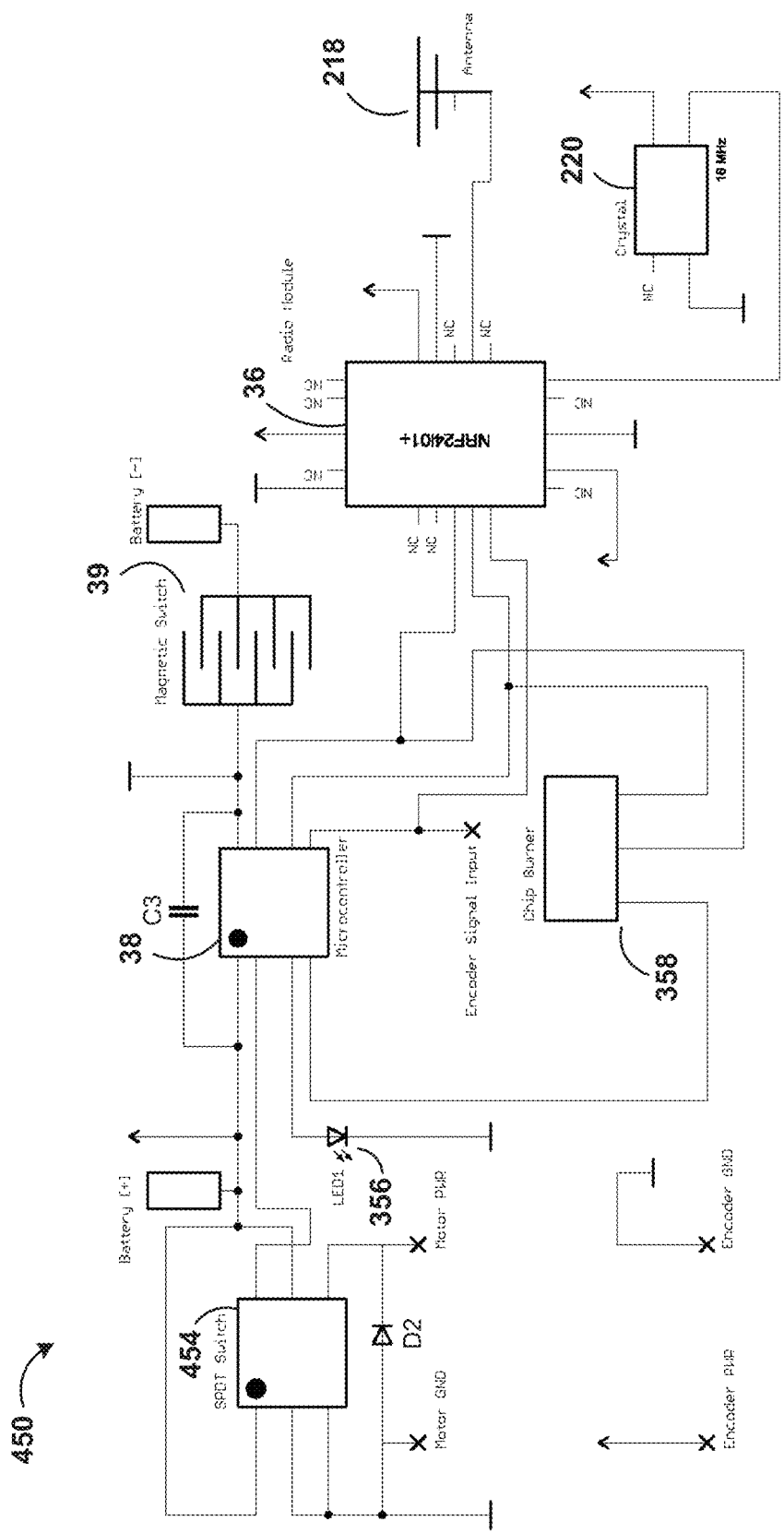

Referring now to FIG. 7C, generally illustrated therein is another example embodiment 450 of a circuit design of the main PCB 32. In this example embodiment, the main microcontroller 38 is protected by the single protective diode 356 which controls current directionality, the communication sub-unit 202 includes an RF transceiver (e.g., an nRF24AP1+ or AT86RF231 transceiver), an antenna 218 and a crystal oscillator 220, and the intermediary device connecting the main microcontroller 38 to the motor 42 is a SPDT switch 454. Similar to the example circuit design in FIG. 7A, the chip burner 358 is used for uploading software to the microcontroller 38. Unlike the example circuit designs in FIGS. 7A and 7B, the transceiver 36 enables transmission and reception of instructions from a base station in real-time. The transceiver 36 can operate based on the ANT™ wireless communication protocol but can also be configured to operate using the Zigbee standard (based on IEEE 802.15.4 for Wireless Personal Area Networks or WPANs). Example values for the components C3 and D2 of FIG. 7C are provided in Table 6, below.

TABLE 6

Example Electronic Component Values for FIG. 7C

| Components | Range |
| --- | --- |
| C3 | 100 nF |
| D2 | 10 V to 40 V, 30 mA to 100 mA |

Figure 7D:
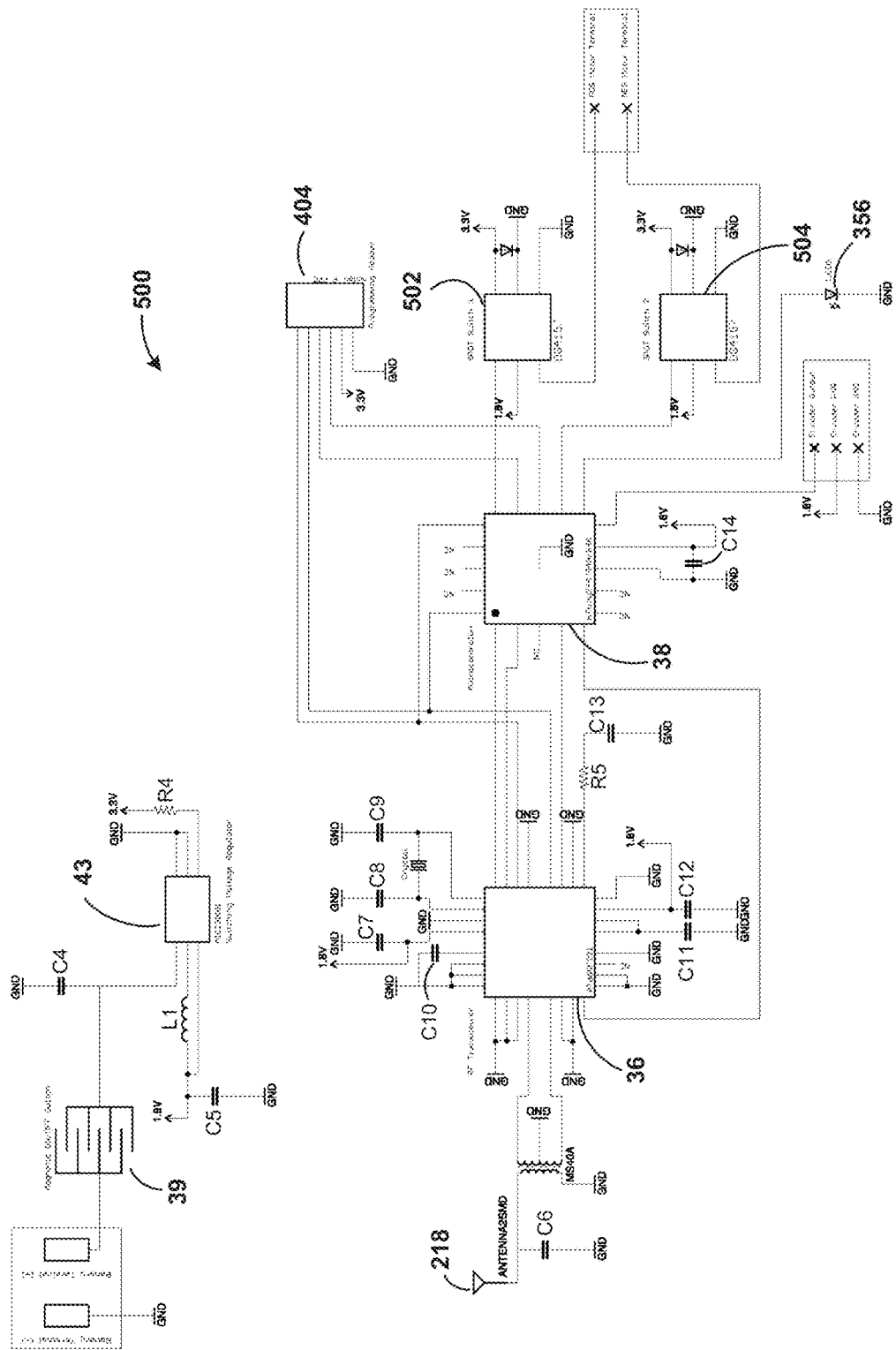

Referring now to FIG. 7D, generally illustrated therein is another example embodiment 500 of a circuit design of the main PCB 32. In this example embodiment, the main microcontroller 38 may be selected from any of the microcontrollers ATtiny24A, ATtiny44A and ATtiny84A provided by ATMEL™, the communication sub-unit 202 includes an RF transceiver 36 (e.g., an AT86RF231 transceiver), and the intermediary device connecting the main microcontroller 38 to the motor 42 includes two SPDT switches 705. It will be understood that, in operation, two SPDT switches 502 and 504 implemented to be equivalent to one DPDT switch. Therefore, similar to the DPDT switch in the Dual Full Bridge Driver 214 in the example circuit design in FIG. 7B, the two SPDT switches 502 and 504 enable the motor 42 to move in a bidirectional motion. To further protect the main PCB 32 circuit, a switching voltage regulator 43 is coupled to the magnetic ON/OFF/RESET switch 39. Also, similar to the example circuit design in FIG. 7C, the RF transceiver 36 and the antenna 218 enable transmission and reception of instructions from a base station in real-time. However, the transceiver used in FIG. 7D supports the Zigbee™ wireless communication protocol instead of the ANT™ protocol. Also, the microcontroller is protected by a single protective diode 356 which controls current directionality. The FPC connector 404 is included into the circuit 400 for uploading software to the microcontroller 38. Example values for the components C4 to C14, R4, R5 and L1 of FIG. 7D are provided in Table 7, below.

TABLE 7

Example Electronic Component Values for FIG. 7D

| Components | Range |
| --- | --- |
| C4 | 100 nF |
| C5 | 100 nF |
| C6 | 0.47 pF |
| C7 | 1 µF |
| C8 | 12 pF |
| C9 | 12 pF |
| C10 | 1 µF |
| C11 | 1 µF |
| C12 | 1 µF |
| C13 | 2.2 pF |
| C14 | 100 nF |
| L1 | 0.47 µH |
| R4 | 4.7 kΩ |
| R5 | 4.7 kΩ |

Referring now to FIG. 8, illustrated therein is an example embodiment 550 of a circuit design of the secondary PCB 44. As described above with reference to FIG. 3E, the secondary PCB 44 includes a sensor 64 and one or more passive electronic components (e.g., a capacitor 62 and a resistor 60). Example values for the components R6 and C15 of FIG. 8 are provided in Table 8, below.

TABLE 8

Example Electronic Component Values for FIG. 8

| Components | Range |
| --- | --- |
| R6 | 50 kΩ |
| C15 | 0.1 µF |

Figure 9A:
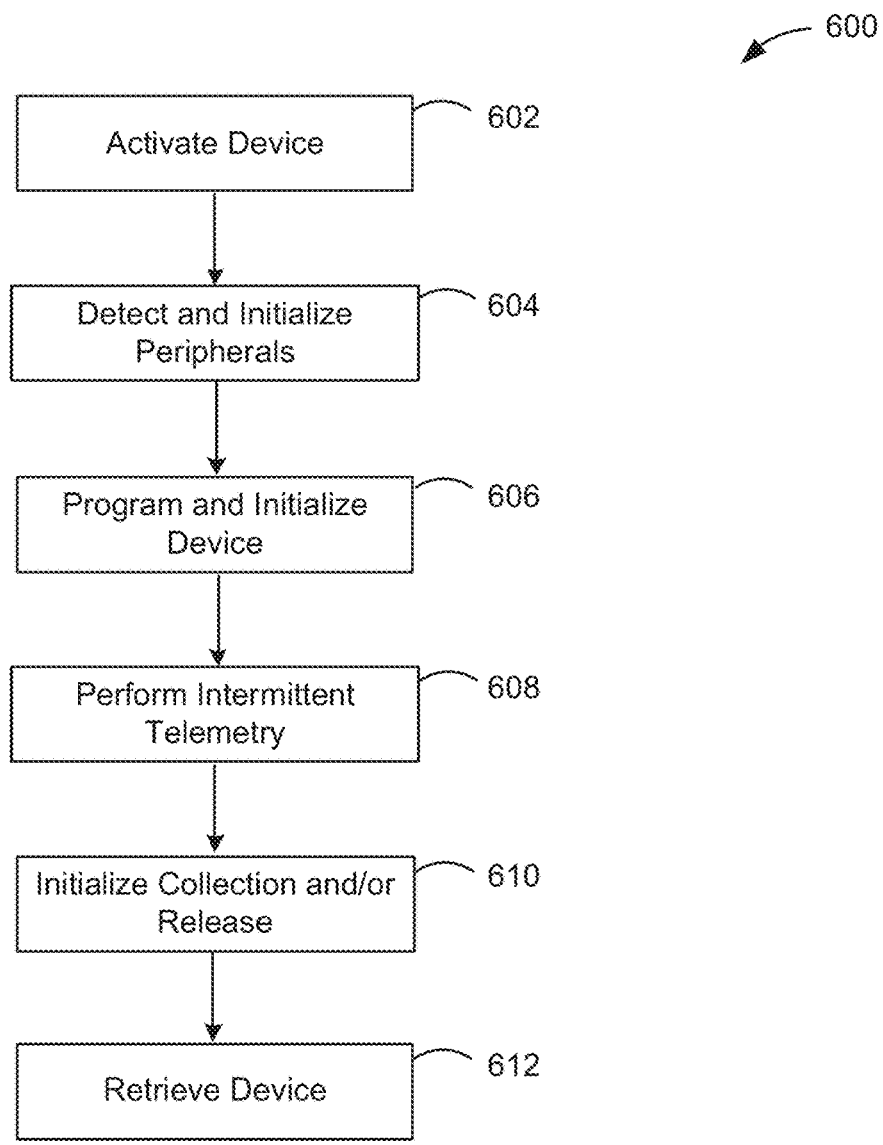
FIGS. 9A to 9F are flowcharts of an example embodiment of various methods of operation for the ingestible medical device.

Referring now to FIG. 9A, shown therein is a high-level flowchart of an example operational method 600 of the ingestible medical device 10. At 602, the ingestible medical device 10 is activated. The ingestible medical device 10 is activated by removing it from its packaging since the packaging includes a small magnet that interacts with the magnetic switch 39 in the ingestible medical device 10 to keep the magnetic switch 39 in an 'OFF' position in which the ingestible medical device 10 is not activated. The small magnet may be selected to be any magnet having a strong magnetic field.

The small magnet may keep the ingestible medical device 10 in the 'OFF' position because the magnetic switch 39 creates an open circuit in the ingestible medical device 10. The open circuit occurs when the small magnet (e.g., a magnet with a strong magnetic field) is brought in close proximity to the ingestible medical device 10 since the small magnet effectively stops current flow in the ingestible medical device 10. Therefore, when the ingestible medical device 10 is removed from its packaging, the magnetic switch 39 no longer interacts with the small magnet on the packaging and the magnetic switch 39 switches to an 'ON' position to activate the ingestible medical device 10. Current may then flow through the electrical pathways in the ingestible medical device 10 (e.g., pathways on the main PCB 32). Accordingly, the magnetic switch 39 is used as a master 'ON'/'OFF' mechanism for the ingestible medical device 10 because in its 'OFF' position no energy may be consumed. As a result, the life of the power supply 40 in the ingestible medical device 10 may be extended significantly.

In some embodiments, an MK24 reed sensor from MEDER™ Electronics may be used as the magnetic switch 39. Alternatively, in some embodiments, the magnetic switch 39 may be a magnetically actuated, normally closed, Single-Pole Single Throw (SPST-NC) switch. In some embodiments, a MEMS magnetic switch, such as one manufactured by MEMSCAP™, may be used as the magnetic switch 39.

In some embodiments, a magnetic switch 39 is not required when the main microcontroller 38 can be placed into a low power state.

In alternative embodiments, the ingestible medical device 10 can be activated by removing or moving an insulating material located between the power supply 40 and the main PCB 32 so that the power supply 40 comes into contact with the main PCB 32.

In alternative embodiments, a thermal switch can be used for activating the ingestible medical device 10. The thermal switch comprises a beam formed by joining together two different metals. The two metals have different thermal conductivity and thus, the two metals expand at different rates as the temperature of the thermal switch increases. As a result, the beam bends and makes contact with an electrical lead to complete the electrical pathway between the power supply 40 and the main PCB 32. In some embodiments, the two metals are selected from metals that can operate at body temperature (e.g., around 37° C.).

After activating the ingestible medical device 10, the main microcontroller 38 begins to detect and initialize peripheral components and/or devices. As well, after activating the ingestible medical device 10, a programming loop for programming and initializing the ingestible medical device 10 is also executed.

At 604, the main microcontroller 38 in the ingestible medical device 10 detects and initializes peripheral devices. As described above, the main microcontroller 38 detects, through one or more groups of GPIOs 208, whether one or more peripheral devices are present on a bus by sending out a series of requests to specific addresses associated with the one or more groups of GPIOs 208. In response, any peripheral device that is present then sends an acknowledging signal to the main microcontroller 38 within a designated time frame. If the main microcontroller 38 does not receive a response within the designated time frame, the main microcontroller 38 operates as if no peripheral device is present.

The main microcontroller 38 then initializes the peripheral devices that are present. The initialization process may vary with different peripheral devices. Generally, the initialization process includes setting one or more parameters (e.g., reference voltages, mode and speed of operation) and formatting of data output. Other peripheral devices that may be included in the ingestible medical device 10 may need to be initialized by setting reference temperatures, pressures, and/or pH calibration.

An example of formatting data output includes selecting frequency channels at which the transceiver 36 may transmit data information when a wireless communication system is included in the ingestible medical device 10. In a further example, if the transceiver 36 uses a spread spectrum protocol, the main microcontroller 38 further initializes the transceiver 36 by setting parameters for performing cyclic redundancy checks (CRC). The CRC can include determining a frequency hopping sequence and/or calculating transmission errors. In other embodiments, other error checking techniques can be used.

After the main microcontroller 38 initializes the peripheral devices, the main microcontroller 38 generally places the peripheral devices in a low-energy state, or may even completely power down the peripheral devices with non-volatile memory, in order to avoid unnecessary consumption of power.

After initializing the peripheral devices, the main microcontroller 38 may poll the transceiver 36 for a start signal from the base station (e.g., a dock). This start signal may generally be followed by operational instructions from the base station. The base station can be a dock that acts as a peripheral device to an external computer and may communicate with the external computer through a COM Port of the external computer using the SPI protocol. Generally, the base station includes a microcontroller and a transceiver. The transceiver is selected to facilitate communication between the ingestible medical device 10 and the base station.

In some embodiments, the base station may provide a cradle for the ingestible medical device 10 in which the ingestible medical device 10 is inserted so that it can be programmed. In some other embodiments, the base station may include a secondary base unit that is worn by the patient to continuously log data and/or track the position of the ingestible medical device 10 as the ingestible medical device 10 passes through the patient.

Figure 9B:
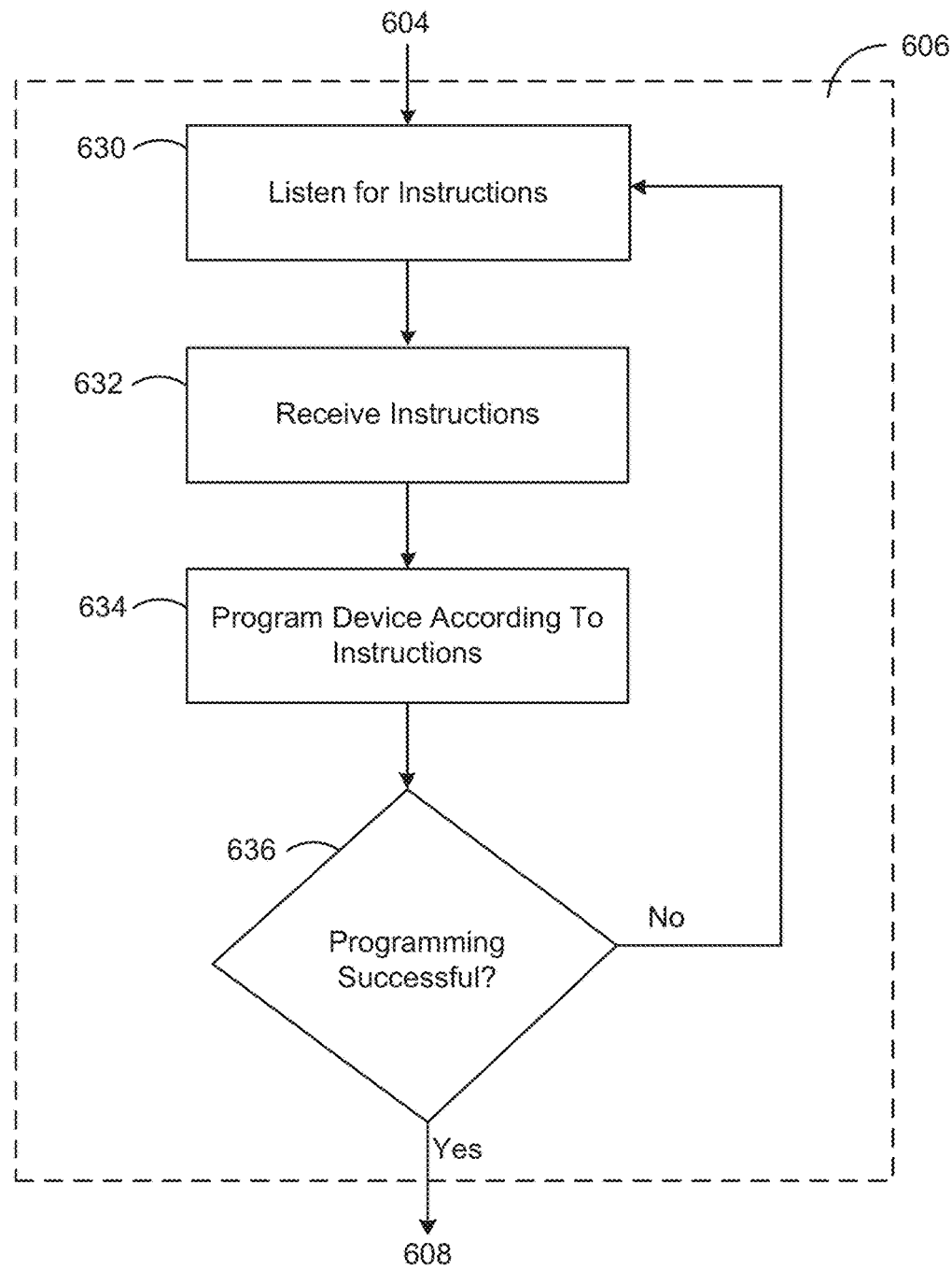

At 606, the main microcontroller 38 programs and initializes the ingestible medical device 10. The main microcontroller 38 may begin to program and initialize the ingestible medical device 10 immediately after being activated once it receives instructions. Referring now to FIG. 9B, shown therein is a flowchart illustrating the 606 of programming and initializing the ingestible medical device 10. Continuing from 604, the main microcontroller 38 places the ingestible medical device 10 in a "listening" state for awaiting instructions at 630.

At 632, the main microcontroller 38 receives instructions from the base station wirelessly through IR or RF transmission depending on the particular implementation of the ingestible medical device 10. In embodiments which utilize IR communication, the IR transmission may be based on modulated infrared light (e.g., between the wavelengths 850 to 930 nm). In embodiments which utilize RF communication, the RF transmission can utilize the Zigbee™ protocol or the ANT™ protocol depending on the particular type of the transceiver 36.

At 634, the main microcontroller 38 configures the ingestible medical device 10 according to the instructions. The instructions may include data identifying a mode of operation (e.g., a type of task, such as collecting of samples and/or releasing of substances), operating parameters (e.g., sampling times, sampling intervals, error logging, sampling locations, etc.), parameters for managing peripheral devices in the ingestible medical device 10 and operating parameters associated with performing a particular test or treatment procedure on an intended patient.

At 636, if programming has been determined to be successful, then the operational method 600 proceeds to 608. At this point the ingestible medical device 10 may be ingested by the intended patient and may proceed to operate according the received instructions and parameters. However, if the main microcontroller 38 determines that the ingestible medical device 10 has not been successfully programmed, the base station can resend the instructions and the main microcontroller 38 continues to "listen" for instructions. The most likely issue to occur would be non-successful programming due to interference in which case the data is resent. However, if there are too many unsuccessful attempts made then the device 10 may be considered to be faulty and should be replaced. It will be understood that any error detection schemes, such as CRC or Checksum, can be used for ensuring that the data received matches the data sent during a wireless communication.

Figure 9C:
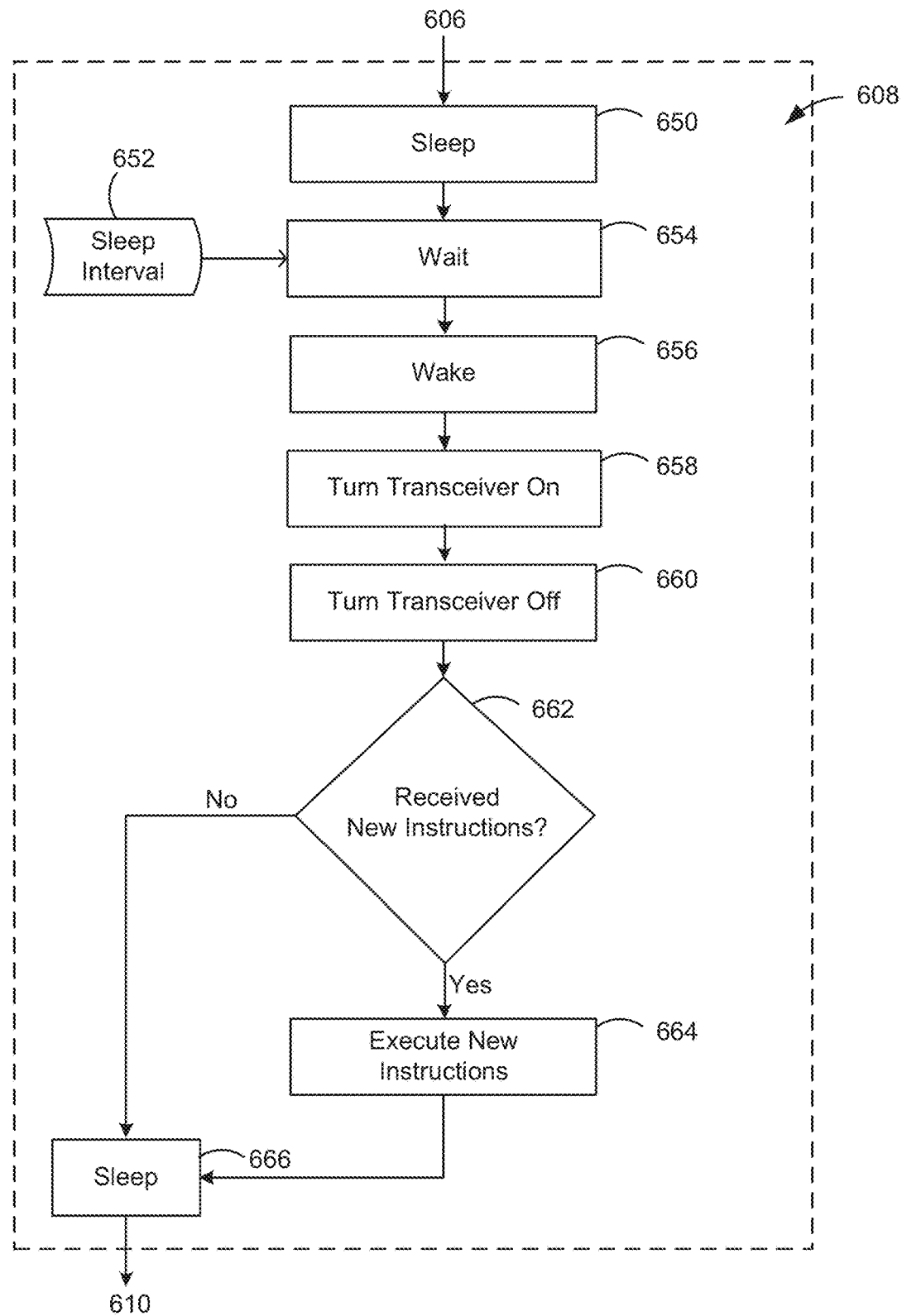

Referring again to FIG. 9A, at 608, the main microcontroller 38 in the ingestible medical device 10 performs intermittent telemetry. Referring now to FIG. 9C, shown therein is a flowchart illustrating an implementation of the 608.

After the main microcontroller 38 programs and initializes the ingestible medical device 10 and the ingestible medical device 10 is ingested by the intended patient, the main microcontroller 38 places the ingestible medical device 10 in a low energy state (e.g., sleeping state) at 650. Following a sleep interval at 652, the main microcontroller 38 waits for a period of time at 654 and then "wakes" the ingestible medical device 10 at 656. At 658, the transceiver 36 is intermittently turned on in order to poll for new instructions from the base station (e.g., new instructions to override previously received instructions) and/or to transmit data to the base station. At 660, the transceiver 36 is turned off to reduce power consumption.

At 662, if the main microcontroller 38 determines that new instructions have been received, the main microcontroller 38 proceeds to execute the new instructions at 664. However, if the main microcontroller 38 determines that new instructions have not been received at 662, the main microcontroller 38 then returns the ingestible medical device 10 to a low energy state or a sleeping state at 666.

Referring again to FIG. 9A, at 610, the main microcontroller 38 initializes operation of the ingestible medical device 10 to collect and/or release a substance. The main microcontroller 38 may initialize operation of the ingestible medical device 10 after waiting a predetermined time interval. The predetermined time interval may be provided as part of the operating instructions provided by the base station. For example, the main microcontroller 38 may receive instructions to only initialize operation of the medical device for collecting samples only after a predetermined time interval of 10 minutes has elapsed (e.g., so that the ingestible medical device 10 may have traveled inside the patient's or subject's body to a target location).

Figure 9D:
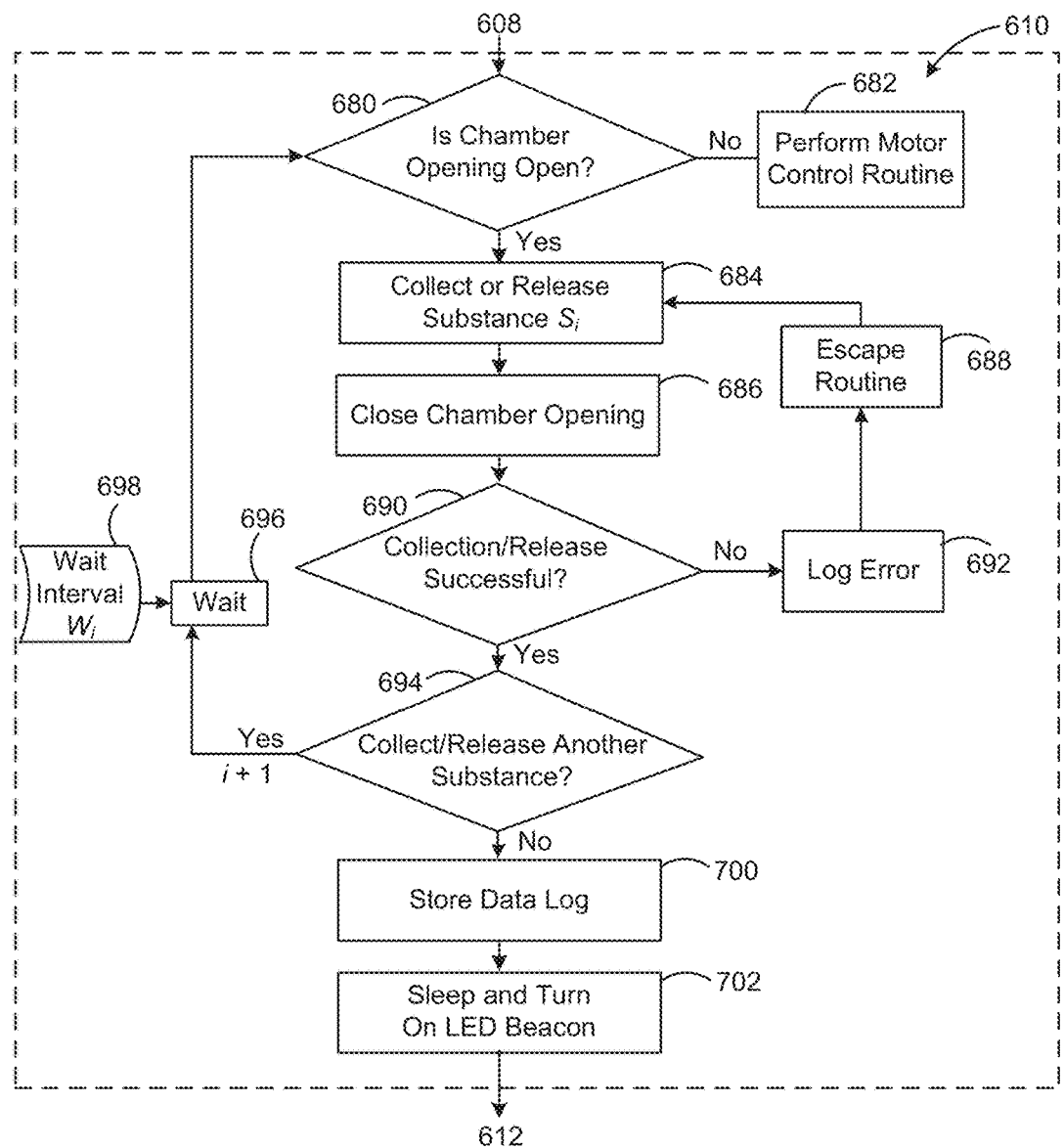

Referring now to FIG. 9D, shown therein is a flowchart illustrating an example embodiment of 610. At 680, in order to collect and/or release a substance, the main microcontroller 38 determines if a chamber opening 22 is not covered by the chamber enclosure 20, e.g., if a chamber opening 22 is aligned with the access port 24 of the chamber enclosure 20. The main microcontroller 38 can determine whether the chamber opening 22 is open from a value of a STATE variable (this is described in more detail below). If the main microcontroller 38 determines that the chamber opening 22 is open to its surroundings, the ingestible medical device 10 proceeds with its operation. If the main microcontroller 38 determines that the chamber opening 22 is not open to its surrounding, the ingestible medical device 10 proceed to 682 in order to rotate the chamber enclosure 20 to align the access port 24 with the chamber opening 22.

Figure 9E:
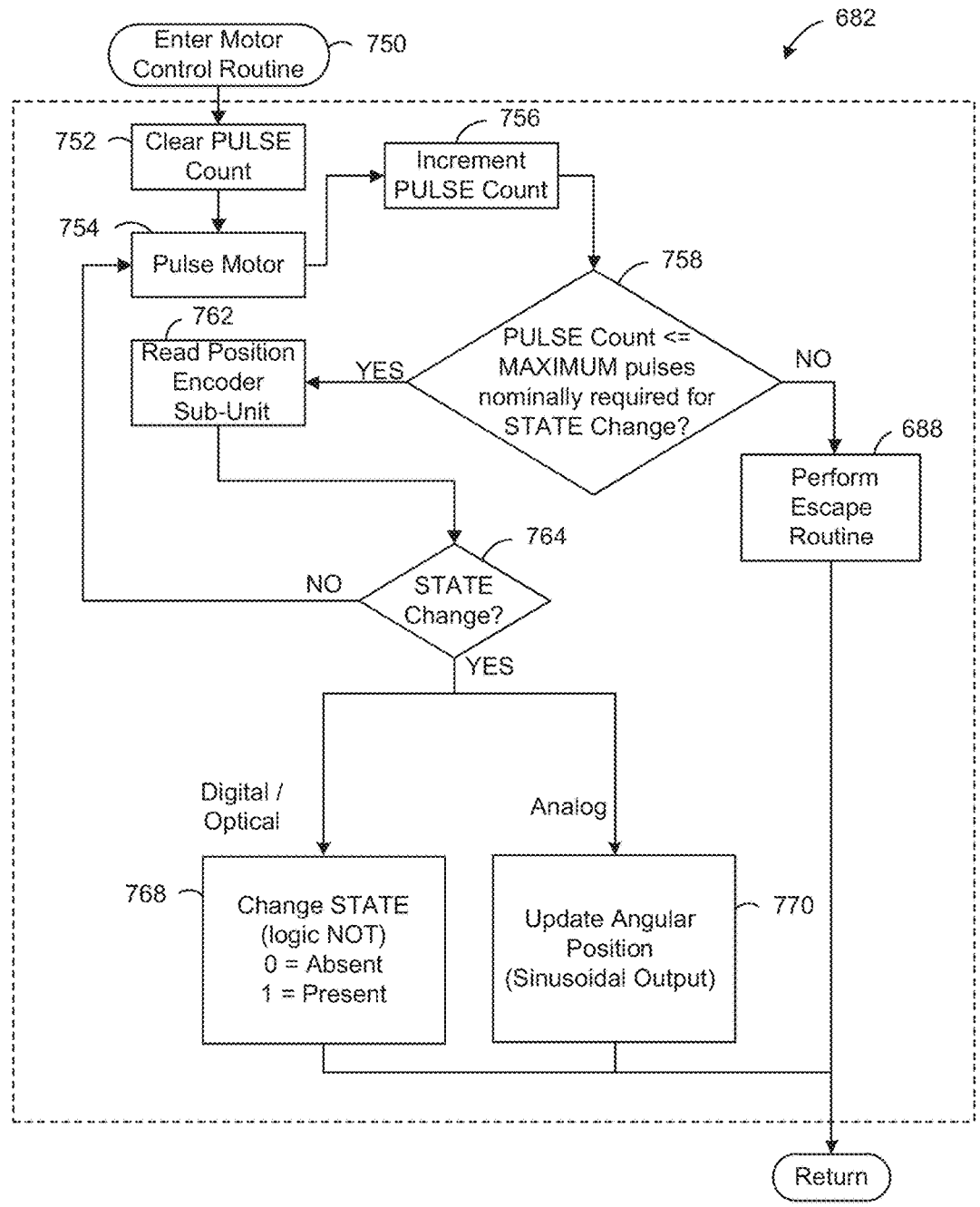

Referring now to FIG. 9E, shown therein is a flowchart illustrating an example embodiment of the motor control routine 682. The main microcontroller 38 initializes the motor control routine 682 for rotating the chamber enclosure 20. The firmware in conjunction with the memory associated with the main microcontroller 38 stores one or more values associated with rotating the chamber enclosure 20. Example values include a PULSE count and a STATE value, which may be stored in registers located in the memory of the main microcontroller 38.

The PULSE count generally corresponds with a number of pulses that the main microcontroller 38 has sent the motor 42. The PULSE count is updated each time the chamber enclosure 20 is rotated by the motor 42. A pulse does not necessarily correspond with a given arc of movement since this is dependent on the resistance faced by the motor 42. Therefore, one cannot say that 1 pulse is necessarily always equal to X degrees of movement. Instead, the PULSE count is a count of how many bursts of energy are sent to the motor 42.

The STATE value generally corresponds with whether or not the access port 24 is aligned with a chamber opening 22. For example, an 'OPEN' state is when a chamber opening 22 is aligned with the access port 24 and a 'CLOSED' state is when a chamber opening 22 is sealed or covered by the chamber enclosure 20. In the digital positioning technique, the STATE value may be updated as a magnet passes by the sensor 64, in other words as the magnet enters or leaves a sensing range of the sensor 64. In the analog positioning technique, the STATE value corresponds to specific voltage values in the positioning signal and can be updated after determining a current relative angular position of the access port 24.

The optical encoding technique is similar to the digital positioning technique. In the optical encoding technique, the STATE value may be updated as the optical markers 1910 on the storage sub-unit 16 pass by the optical encoder 1406, in other words as the optical markers 1910 enter or leave a sensing range of the optical encoder 1406.

Generally, when an operating parameter (e.g., arrival at a target location, a predetermined time interval elapsed, etc.) indicates that the ingestible medical device 10 is to begin collecting or releasing a substance, the main microcontroller 38 supplies a series of electrical pulses to the motor 42 for controlling the rotation of the motor 42 and accordingly, a rotation of the chamber enclosure 20. Between each pulse in the series of electrical pulses, the main microcontroller 38 determines the status of the motor 42 and the chamber enclosure 20 based on the STATE value.

As illustrated in FIG. 9E, the main microcontroller 38 enters the motor control routine at 750 and clears the PULSE count at 752 before proceeding to send a series of pulses to the motor 42. The main microcontroller 38 sends an electrical pulse to the motor 42 at 754 and increments the PULSE count at 756 accordingly. Generally, the duration and/or frequency of the electrical pulse may be modulated (e.g., by Pulse-Width Modulation (PWM)) for controlling the rotational speed and/or the rotational direction of the motor 42.

The PULSE count value is important for several reasons. First, a minimum number of pulses are required in order to rotate a magnet 46*m* that is being sensed by the sensor 64, out of the range of the sensor 64. The PULSE count is used to ensure that the minimum number of pulses is met before the STATE value is changed. There are typically a minimum number of pulses that are used to clear the motor 42 from the sensor 64.

A record of the number of electrical pulses before a change is recorded in the STATE value enables the ingestible medical device 10 to map out the positioning signal detected by the secondary PCB 44 as a function of pulses sent from the main microcontroller 38 to the motor 42. As a result, a parametrically defined function of distance (e.g., arc-length) to a number of pulses and current may be generated. This provides the main microcontroller 38 with the ability to self-calibrate and self-regulate in order to eliminate small manufacturing variations that can occur between different implementations of the ingestible medical devices 10. As well, the parametrically defined function allows the ingestible medical device 10 to more easily adapt to different coefficients of friction and sample viscosity when in use.

Furthermore, the PULSE count may be used by the main microcontroller 38 for error detection. At 758, if any rotation of the chamber enclosure 20 requires a number of pulses that exceeds a statistical norm (e.g., a current draw exceeds a maximum current threshold value) for changing the STATE value (e.g., at 1020), the main microcontroller 38 responds by varying the size of the electrical pulse and/or calling an escape routine at 760. The escape routine 760 is described in more detail below with reference to FIG. 9F.

The contents of the GI tract may vary widely in viscosity and composition. Accordingly, at different locations in the GI tract, the motor 42 may be subject to various strains and therefore generally uses a varying range of power (e.g., the range of power may be implemented through PWM) to move a given distance in a viscous environment compared to a non-viscous environment.

When the ingestible medical device 10 encounters abnormally viscous or particulate matter, the main microcontroller 38 starts to increase the amount of power delivered to the motor 42 through a time-proportioned PWM. During the time-proportioned PWM, the motor 42 receives an increasing percentage of power in a given period of time. For example, during normal operation, the motor 42 receives 70% of the power 100% of the time, but during time-proportioned PWM, the motor 42 receives 100% of the power 70% of the time. In this way, power supplied to the motor 42 is continuously ramped up until the ingestible medical device 10 bypasses or removes the viscous or particulate matter. Generally, the error detection at 758 relies on a proportional relationship between a current drawn by the motor 42 and a rotational motion of the chamber enclosure 20. The current being drawn by the motor 42 may be measured by placing a shunt resistor in series with the motor 42, and using the A/D Converter 212 to measure the voltage drop across the shunt resistor.

During normal operation, an increasing ratio of current drawn by the motor to the rotational motion of the motor may indicate increasing viscosity of the substances in the environment and thus, a need to adjust the current supplied to the motor 42. This can be detected if the main microcontroller 38 determines that the number of pulses exceeds the statistical norm for changing the STATE value because there is an increase in sample viscosity. In this case, the main microcontroller 38 may gradually scale up (e.g., through PWM) the duration and/or frequency of the electrical pulses sent to the motor 42 to a maximum value corresponding to a maximum current threshold value.

However, if this ratio continues to increase beyond the maximum current threshold value (e.g., when the rotational motion is nearly zero mm/s), the ratio may indicate that the access port 24 is unable to close or open due to an obstructing substance. For example, the environment surrounding the ingestible medical device 10 may include substances that may be too thick for the ingestible medical device 10 to operate in and/or a substance may be blocking the access port 24 from properly closing or opening. An error is then be logged along with other data information (e.g., a time and/or a position at which the error was encountered, a type of error encountered, etc.). If the maximum current threshold is reached without resolving the problem (e.g., that the number of pulses exceeds the statistical norm for changing the STATE value), the main microcontroller 38 may proceed to call the escape routine at 760.

Generally, the maximum current threshold value may correspond to any one of the following factors that has the lowest current rating minus a safety margin. The factors include a discharge capacity of the power supply 40 (e.g., how quickly the power supply 40 may be discharged without causing damage), one or more electrical characteristics associated with the electronic components through which the maximum current may travel (e.g., the maximum current that may be sustained by each component in a pathway of the current), and one or more electrical characteristics associated with the electrical pathways on the main PCB 32.

Still referring to FIG. 9E, if the main microcontroller 38 determines that the number of pulses do not exceed the statistical norm for changing the STATE value, the main microcontroller 38 reads the positioning signal provided by the position encoder sub-unit at 762. At 764, the main microcontroller 38 may toggle the positioning signal from the sensor 64 for determining whether the STATE value has changed as a result of pulsing of the motor 42.

As described above with reference to FIGS. 5 and 6, and 19, the STATE value may correspond with the information in the positioning signal provided by the sensor 64 or by the optical encoder 1406, respectively. For example, in the analog positioning technique described with reference to FIG. 5, the STATE value is 'OPEN' when the current relative angular position of the access port 24 corresponds with an angular position of a chamber opening 22 and the STATE value is 'CLOSED' when the current relative angular position of the access port 24 does not correspond with any angular positions of the chamber openings 22. Similarly, in the digital positioning technique described with reference to FIG. 6, the STATE value is 'OPEN' when the positioning signal has a 'high' value and the magnet count indicates that the access port 24 is aligned with a chamber opening, and the STATE value is 'CLOSED' when the positioning signal has a low' value.

As described above with reference to FIG. 19, the optical encoding technique operates in a similar manner as the digital positioning technique. In the optical encoding technique, the STATE value is 'OPEN' when a positioning signal has a low' value and the optical marker count indicates that the access port 24 is aligned with a chamber opening, and the STATE value is 'CLOSED' when the positioning signal has a 'high' value.

If the main microcontroller 38 determines that there is a change in state at 764, the STATE value is changed according to whether the analog positioning technique is used (at 770) or the whether the digital positioning technique or the optical encoding technique is used (at 768).

Referring back to FIG. 9D, after the main microcontroller 38 determines that the chamber opening 22 is not covered by the chamber enclosure 20, the ingestible medical device 10 then operates to collect and/or release a substance $S_i$ at 684. Thereafter, the chamber opening 22 is closed by calling the motor control routine 682 at 686.

At 690, the main microcontroller 38 then determines whether or not the collection and/or release was successful, that is whether an error has occurred that prevents the chamber opening 22 from being properly covered or uncovered by the chamber enclosure 20 as the case may be. If the main microcontroller 38 determines that the collection and/or release is not successful, an error is logged at 692 for reference later (e.g., when the ingestible medical device 10 is retrieved for analysis). To deal with the error, the main microcontroller 38 can initialize the escape routine at 688 (described in FIG. 9F) for correcting the error. If the error is corrected, the ingestible medical device 10 continues to operate to collect and/or release the substance at 684 and 686.

If the main microcontroller 38 determines that the collection and/or release of the substance $S_i$ is successful at 690, the main microcontroller 38 determines whether another substance is to be collected and/or released based on the operating instructions at 694. If the main microcontroller 38 determines that no additional substance is to be collected and/or released, the main microcontroller 38 stores the operating results and/or data at 700, places the ingestible medical device 10 in a low energy state and turns on the LED Beacon at 702 for easier identification of the ingestible medical device 10 during extraction of the ingestible medical device 10 from the body of the patient or subject.

However, if the main microcontroller 38 determines that another substance is to be collected and/or released at 690, the ingestible medical device 10 continues to operate. For ease of exposition, the substance number i is incremented by 1 for each additional collection and/or release of a substance from a different chamber of the ingestible medical device 10. It will be understood that the main microcontroller 38 may not need to maintain a count of the collection and/or release of the substances. The ingestible medical device 10 may continue to operate after waiting at 696 for a predetermined wait interval W, at 698. The predetermined wait interval may vary with each collection and/or release of substance $S_i$, and generally may be provided from the operating instructions.

In some embodiments, the transceiver 36 in the ingestible medical device 10 may facilitate real-time telemetry during collection and/or release of a substance $S_i$. For example, the transceiver 36 may transmit data associated with the operation of the ingestible medical device 10 and/or samples collected to the base station in real-time.

In some embodiments, the operation of the ingestible medical device 10 may be triggered manually using ultrasound technology and/or fluoroscopy technology as a guidance system. These guidance systems may be used to see the position of the ingestible medical device 10 and used to know when to trigger the ingestible medical device 10 for operation by using an RF signal.

In some embodiments, a position of the ingestible medical device 10 inside the body can be determined using ultrasound and/or fluoroscopy technology. In some alternate embodiments, the position of the ingestible medical device 10 can be determined by triangulation, using one or more RF signal receivers and an intensity of a RF signal received from the ingestible medical device 10 or using a MEMS microphone and an acoustic signal received from the ingestible medical device 10. In some alternative embodiments, the position of the ingestible medical device 10 may be located using an array of external magnetic sensors.

Figure 9F:
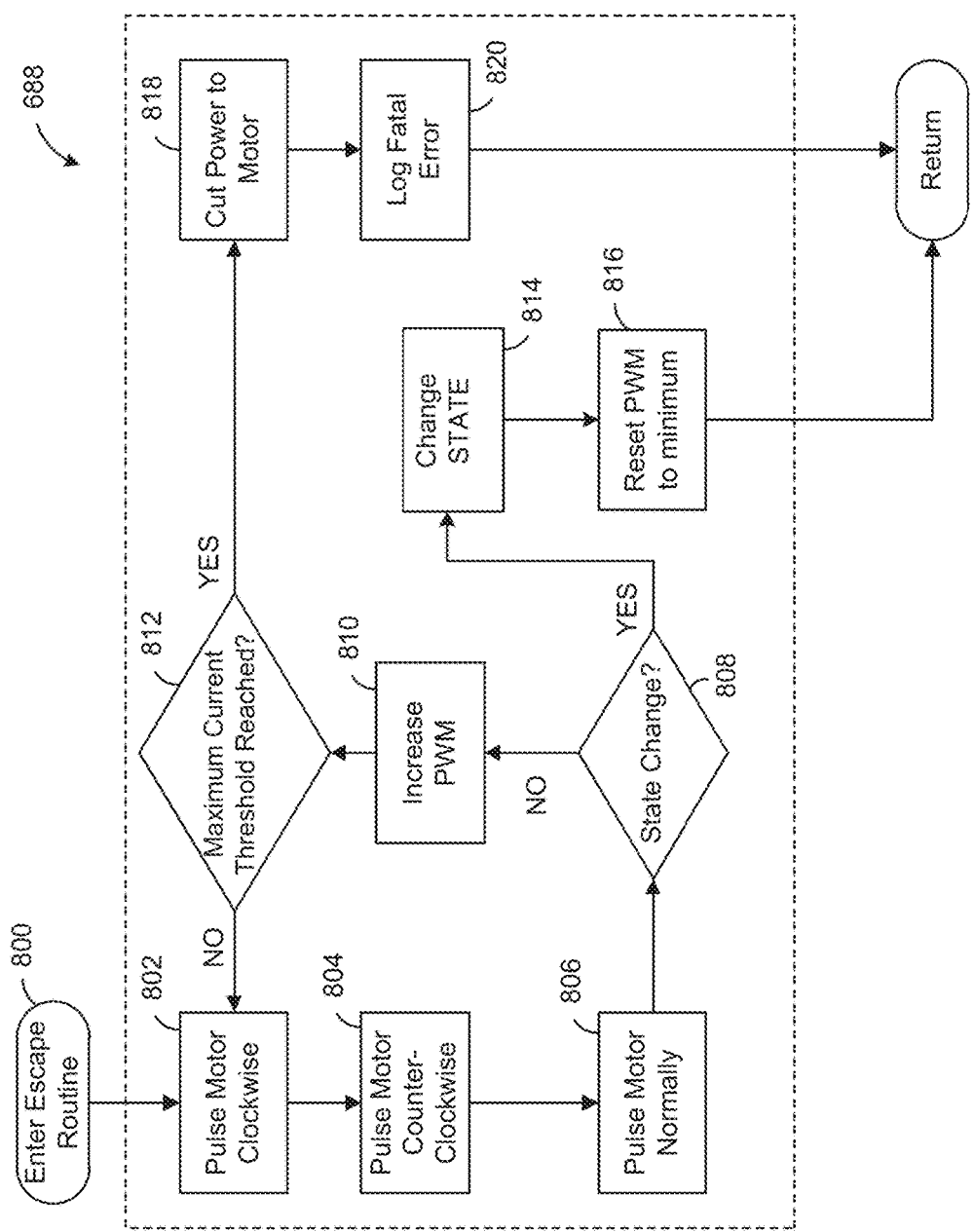

Referring now to FIG. 9F, shown therein is a flowchart of an example embodiment of the escape routine 688. When an error is encountered during operation of the ingestible medical device 10, the ingestible medical device 10 may immediately make a record of the error. This record can be used in later analysis for explaining potential anomalies in the samples and/or results collected from the GI tract of a patient or subject. The recording of the error is usually followed by initiating a corrective action, such as entering the escape routine 688 at 800.

Generally, the focus of the escape routine 688 is to cover a chamber opening 22 that is, to rotate the chamber enclosure 20 in order to seal the chamber opening 22. During the escape routine 688, the main microcontroller 38 may sequentially pulse the motor 42 to rotate the motor 42 in opposing directions. That is, the main microcontroller 38 may first pulse the motor 42 to rotate clockwise at 802 so that the chamber enclosure 20 may also rotate clockwise. The main microcontroller 38 may then pulse the motor 42 to rotate counter-clockwise at 804 so that the chamber enclosure 20 may also rotate counter-clockwise. The order of clockwise and counter-clockwise rotation can be switched in other embodiments.

In some embodiments, the main microcontroller 38 may then not send any pulses to the motor 42 to allow the motor 42 to rest so that the obstructing substance may be released from the access port 24. In some other embodiments, the main microcontroller 38 may continue to pulse the motor 42 normally at 806 to rotate the chamber enclosure 20 in one direction.

As previously described, the DPDT switch in the Dual Full Bridge Driver 214 enables an applied polarity to be arbitrarily switched for facilitating bidirectional motion of the motor 42. In some embodiments, the main microcontroller 38 may rapidly alternate the polarity of the DPDT switch in the Dual Full Bridge Driver 214. The A/D Converter 212 allows for the measurement of the current drawn by the motor 42 at all times by means of a shunt resistor in series between a common leg and the motor 42. If the measured current drawn corresponds to an increased strain on the motor 42, the duty cycle of the DPDT switch in the Dual Full Bridge Driver 214 is altered to reduce the strain on the motor 42.

If the main microcontroller 38 determines that the escape routine 688 is successful, the main microcontroller 38 records the change in state in the STATE value at 808, changes the state at 814, and readjusts the PWM to a value used during normal operation at 816. The main microcontroller 38 then continues to operate the ingestible medical device 10 normally to collect and/or release a substance according to the operating instructions. If the ingestible medical device 10 operates by collecting and/or releasing a substance according to a predetermined timeline, the main microcontroller 38 can continue to operate the ingestible medical device 10 after taking into consideration any extra time that was spent correcting the error (e.g., the extra time is subtracted from the following time interval).

If the main microcontroller 38 determines that the escape routine 668 is not successful at 810, the main microcontroller 38 continues to increase the current provided to the motor 42 at 810 to the maximum current threshold value. In some embodiments, the main microcontroller 38 increases the current provided to the motor 42 in incremental steps. In some alternate embodiments, the main microcontroller 38 determines, for a specific situation, a PWM that can deliver an optimal torque to the motor 42.

If the maximum current threshold value has not been reached at 812, the main microcontroller 38 repeats 802 to 806. If the maximum current threshold value is reached at 812, the main microcontroller 38 stops the ingestible medical device 10 from further operation by cutting power to the motor 42 and other peripherals at 818. However, the main microcontroller 38 may turn on the LED Beacon (e.g., similar to 702) for easier identification at retrieval. The main microcontroller 38 may also turn on the transceiver 36 in order to intermittently transmit location information. For example, the transceiver 36 may send a message to the base station.

The main microcontroller 38 may also record that a fatal error has occurred at 820. The fatal error indicates that the ingestible medical device 10 encountered an error from which it cannot recover and thus the ingestible medical device 10 is unable to continue its normal operation. The ingestible medical device 10 is then moved along by peristaltic motion until it is extracted from the body of the patient or subject and retrieved at 612.

When the ingestible medical device 10 has completed its operation or is unable to continue its normal operation, the main microcontroller 38 may place all peripherals into a low-energy state to conserve power. An LED located on the main PCB 32 may also be pulsed at a very low duty cycle so that the ingestible medical device 10 may be more easily identified and recovered once excreted from the patient. In some embodiments where multiple ingestible medical devices 10 are ingested by the same patient simultaneously, the ingestible medical devices 10 may be differentiated with LEDs of different colors in combination with software identifiers that are programmed into the ingestible medical device 10.

At retrieval, the ingestible medical device 10 may be subject to further analysis depending on its programmed task. For example, if the ingestible medical device 10 was programmed for collecting samples from the patient, the ingestible medical device 10 may be retrieved so that its collected samples are further analyzed. Generally, the samples in the ingestible medical device 10 may be extracted through manual pipetting or an automated technique as is known by those skilled in the art. The extracted samples can be analyzed using various techniques, such as but not limited to, biochemical analysis, for example.

In some embodiments, after the ingestible medical device 10 has been retrieved, the base station can transmit instructions to the ingestible medical device 10 regarding how contents of the ingestible medical device 10 are to be extracted. For example, the ingestible medical device 10 may be placed in the cradle of the base station after it is retrieved. Once in the cradle, a programming component of the base station, such as a radio transceiver or an Infrared transceiver, allows a wireless connection between the ingestible medical device 10 and the base station to be reestablished so that the ingestible medical device 10 can receive instructions regarding the extraction procedure from the base station.

The cradle may include a water-tight and autoclave-tolerant compartment in which the ingestible medical device 10 may be cleaned. The compartment may also be used to extract the samples inside the ingestible medical device 10. Generally, the cleaning and extraction process may involve sequentially pumping fluids into and draining the fluids out of the chambers of the storage sub-unit 16 of the ingestible medical device 10.

Figure 10A:
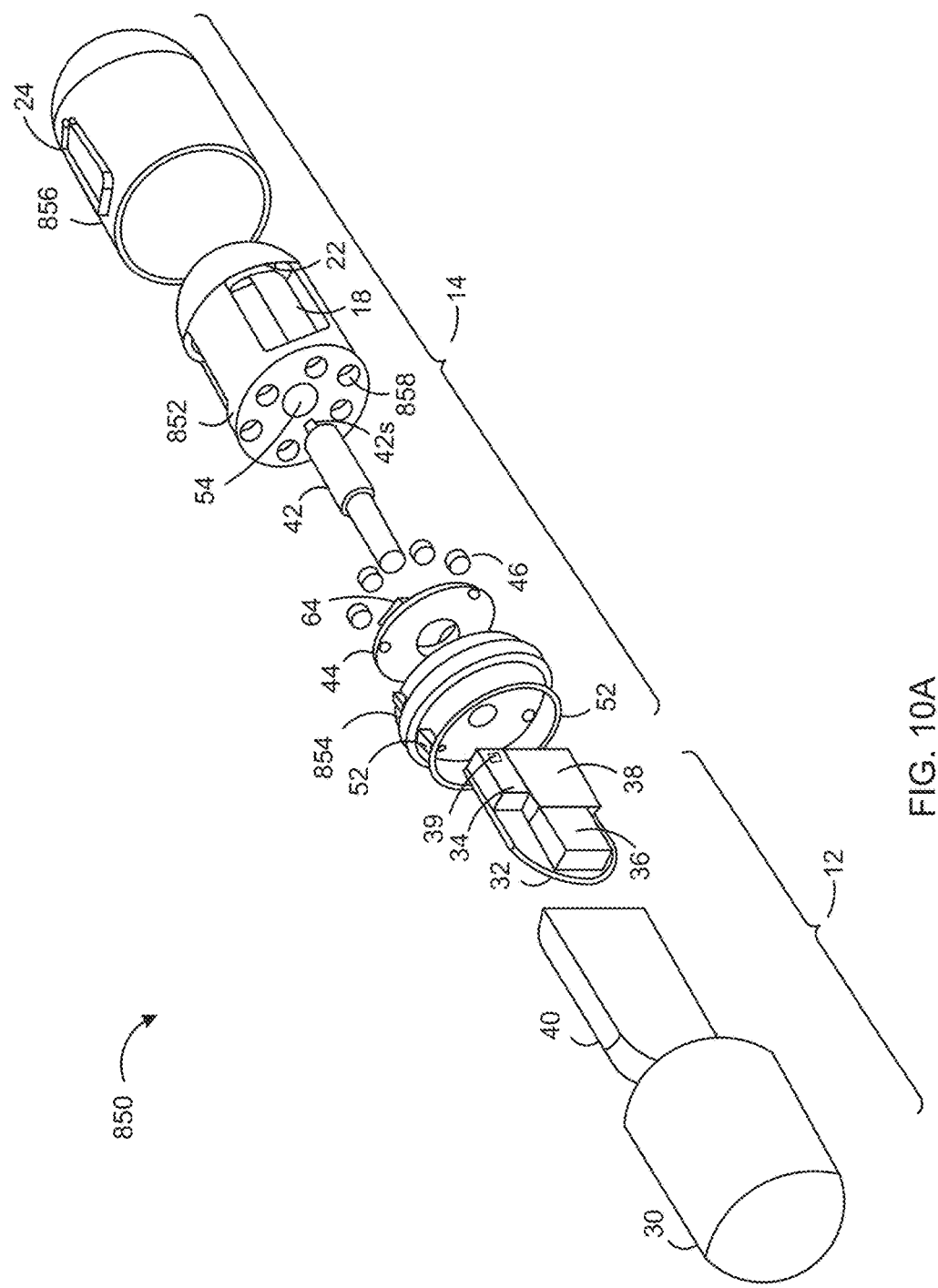
FIG. 10A is a diagram of another example embodiment of an ingestible medical device.

Referring now to FIG. 10A, illustrated therein is a diagram of another example embodiment of an ingestible medical device 850. In this example embodiment, the ingestible medical device 850 includes a rotating storage sub-unit 852 and a stationary chamber enclosure 856, instead of the stationary storage sub-unit 16 and the rotating chamber enclosure 20 of the ingestible medical device 10.

As illustrated in FIG. 10A, many of the components in the ingestible medical device 850 are similar to the components used in the ingestible medical device 10 described above. These similar components are referred to by the same reference numerals for consistency. In comparison with the ingestible medical device 10, several components in the ingestible medical device 850 are physically different, such as the storage sub-unit 16 and the chamber enclosure 20 of the ingestible medical device 10 which are now replaced by a midsection joint 854, a storage sub-unit 852 and a chamber enclosure 856 in the medical device 850. Additionally, several components, such as the secondary PCB 44 and the encoding magnet arrangement 46 in the ingestible medical device 10 are altered in the medical device 850.

Similar to the storage sub-unit 16 of the ingestible medical device 10, the storage sub-unit 852 includes one or more chambers 18 with corresponding chamber openings 22. However, unlike the storage sub-unit 16, the storage sub-unit 852 now includes one or more apertures 858 in which the magnets of the encoding magnet arrangement 46 may be embedded. Example embodiments of the storage sub-unit 852 of the ingestible medical device 850 are shown in each of FIGS. 10B and 10O.

Figure 10B:
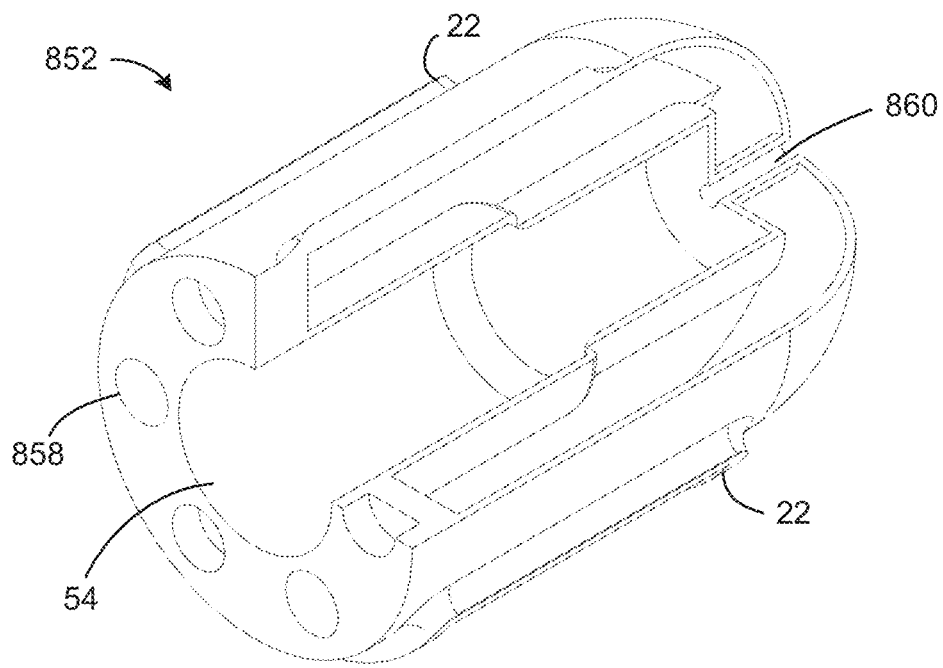
FIGS. 10B and 10O are example embodiments of a rotatable storage sub-unit of the ingestible medical device shown in FIG. 10A.

Referring now to FIG. 10B, illustrated therein is a partial view of an example embodiment of the storage sub-unit 852 of the ingestible medical device 850 shown in FIG. 10A. As shown in FIG. 10B, the motor compartment 54 in the storage sub-unit 852 ends with a truncated aperture 860 in order to couple the storage sub-unit 852 with a shaft 42s of the motor 42 for rotating the storage sub-unit 852.

Another example embodiment of the rotatable storage sub-unit 852 is shown in FIG. 10O as storage sub-unit 852p which can include a polymer band 862 covering a circumferential wall. The polymer band 862 is gradually dissolved to expose each of the underlying chambers 18 during an operation of the ingestible medical device 850. The polymer band 862 can be designed to selectively react with certain chemicals. The polymer band 862 can also contain a reagent for an in-vivo experiment or a drug. The polymer band 862 also demonstrates how space can be used for multifunction/multistage processes on a single chamber opening. Due to these properties of the polymer band 862, this example storage sub-unit 852p can be used for a specific application of the ingestible medical device 850.

Referring back to FIG. 10A, unlike the chamber enclosure 20 of the ingestible medical device 10, the chamber enclosure 856 of the ingestible medical device 850 is now stationary and thus is releasably coupled to the midsection joint 854. The midsection joint 854 is similar to the top portion of the storage sub-unit 16 of the ingestible medical device 10 and includes engagement members 52 for releasably coupling with the end enclosure 30.

Also, as illustrated in FIG. 10A, the secondary PCB 44 is now coupled with the midsection joint 854 for interacting with the encoding magnet arrangement 46 embedded in the storage sub-unit 852. As well, the sensor 64 on the secondary PCB 44 is aligned with the center of the access port 24 since the chamber enclosure 856 is now stationary. Correspondingly, the primary magnet 46*p* of the encoding magnet arrangement 46 is aligned with a center of a chamber opening 22, which may be referred to as a primary chamber opening for use as frame of reference.

Despite the above described variations for the ingestible medical device 850, the ingestible medical device 850 generally operates in the same manner as the ingestible medical device 10 except that in the medical device 850 the storage sub-unit 852 is the rotational element.

Figure 11A:
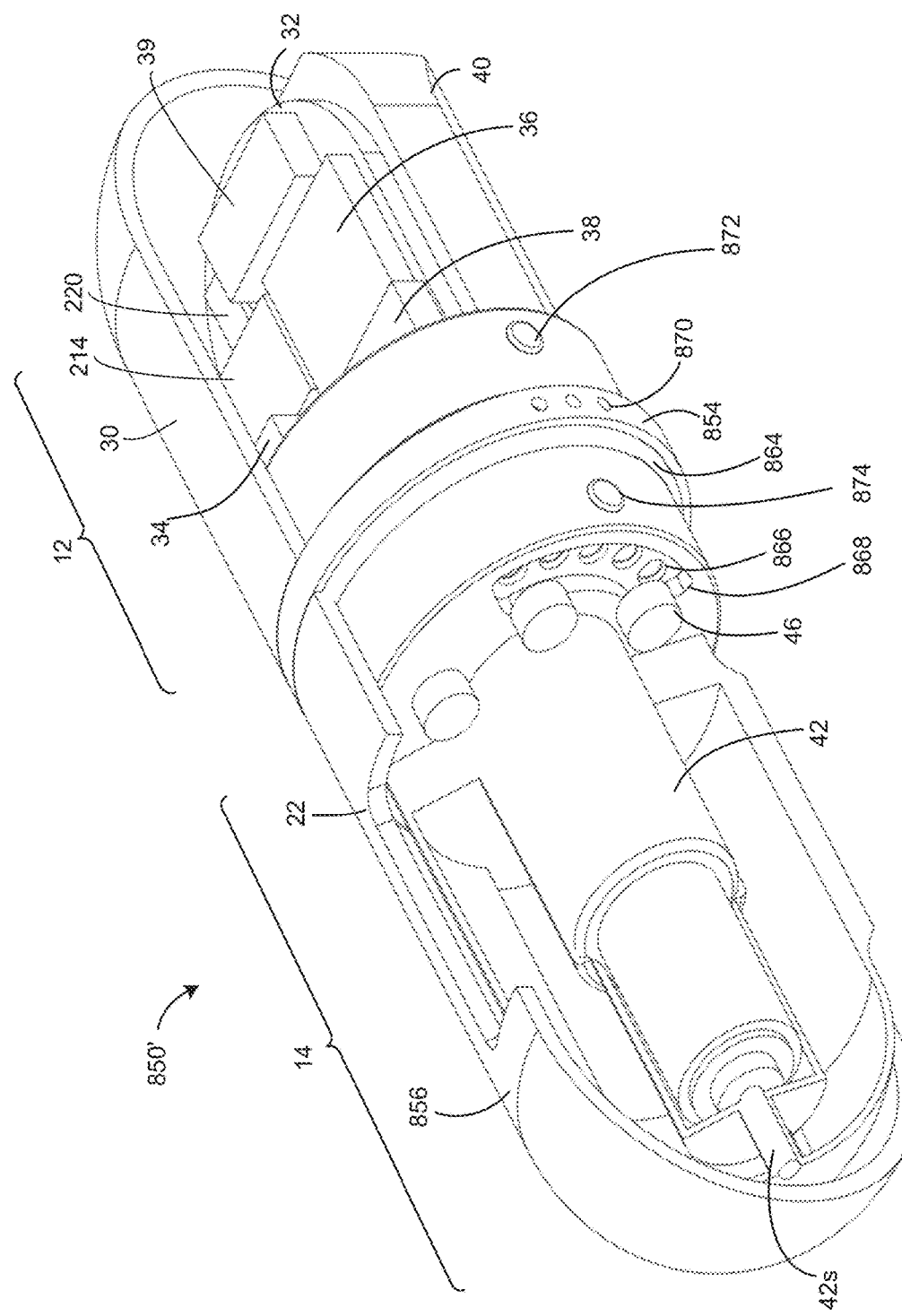
FIG. 11A is a partial view of another example embodiment of an ingestible medical device.

In some alternate embodiments, the ingestible medical device 850 can be structurally varied. Referring now to FIG. 11A, illustrated therein is a partial view of another example embodiment of an ingestible medical device 850'.

The ingestible medical device 850', as illustrated in FIG. 11A, comprises many similar components as the ingestible medical device 850 in FIG. 10A, with several mechanical differences. In comparison with the ingestible medical device 850, the ingestible medical device 850' includes several additional components, such as coupling seals 864 on either sides of the midsection joint 854 (both seals 864 are more clearly illustrated in FIG. 11C), a programming and charging connector 866 on the secondary PCB 44 for receiving firmware from the base station and for charging the power source 40, apertures 868 on one end of the midsection joint 854 for coupling with the programming and charging connector 866, and apertures 870 at a center of the midsection joint 854 for coupling to an auxiliary sensor connector 876 (the auxiliary sensor connector is more clearly shown in FIG. 11B) for connecting to auxiliary environmental sensors. In some embodiments, the coupling seals 864 can be rubber gaskets. Furthermore, each end of the circumferential wall of the midsection joint 854 includes engaging members 872 and 874 for locking the end enclosure 30 and chamber enclosure 856, respectively, into place. One end of the motor 42 is also coupled to the midsection joint 854.

Figure 11B:
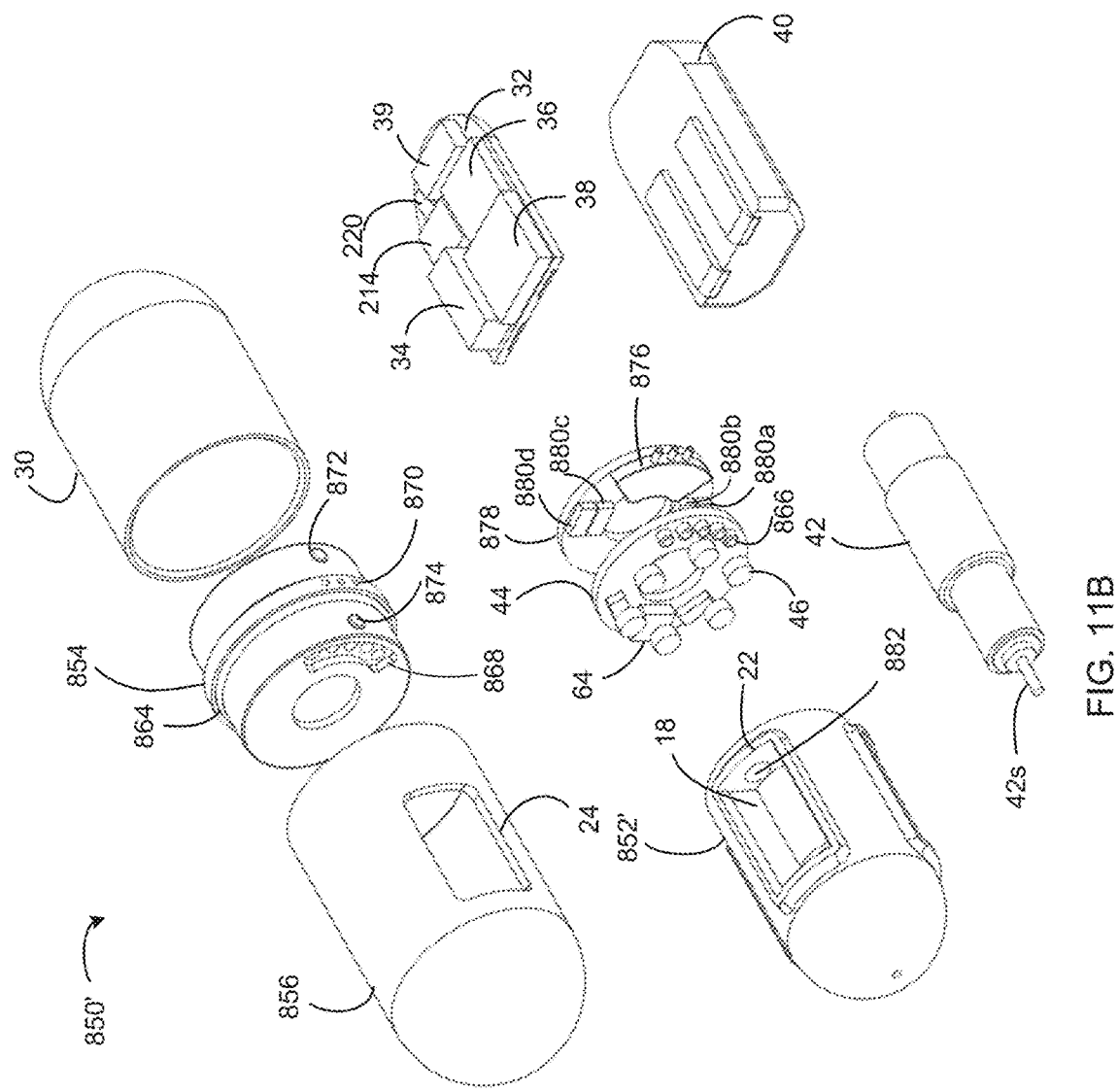
FIG. 11B is an exploded view of the ingestible medical device of FIG. 11A.

Referring now to FIG. 11B, illustrated therein is an exploded view of the ingestible medical device 850' of FIG. 11A. An environmental sensor PCB 878 is included in this example embodiment and is housed inside one end of the midsection joint 854.

Figure 11C:
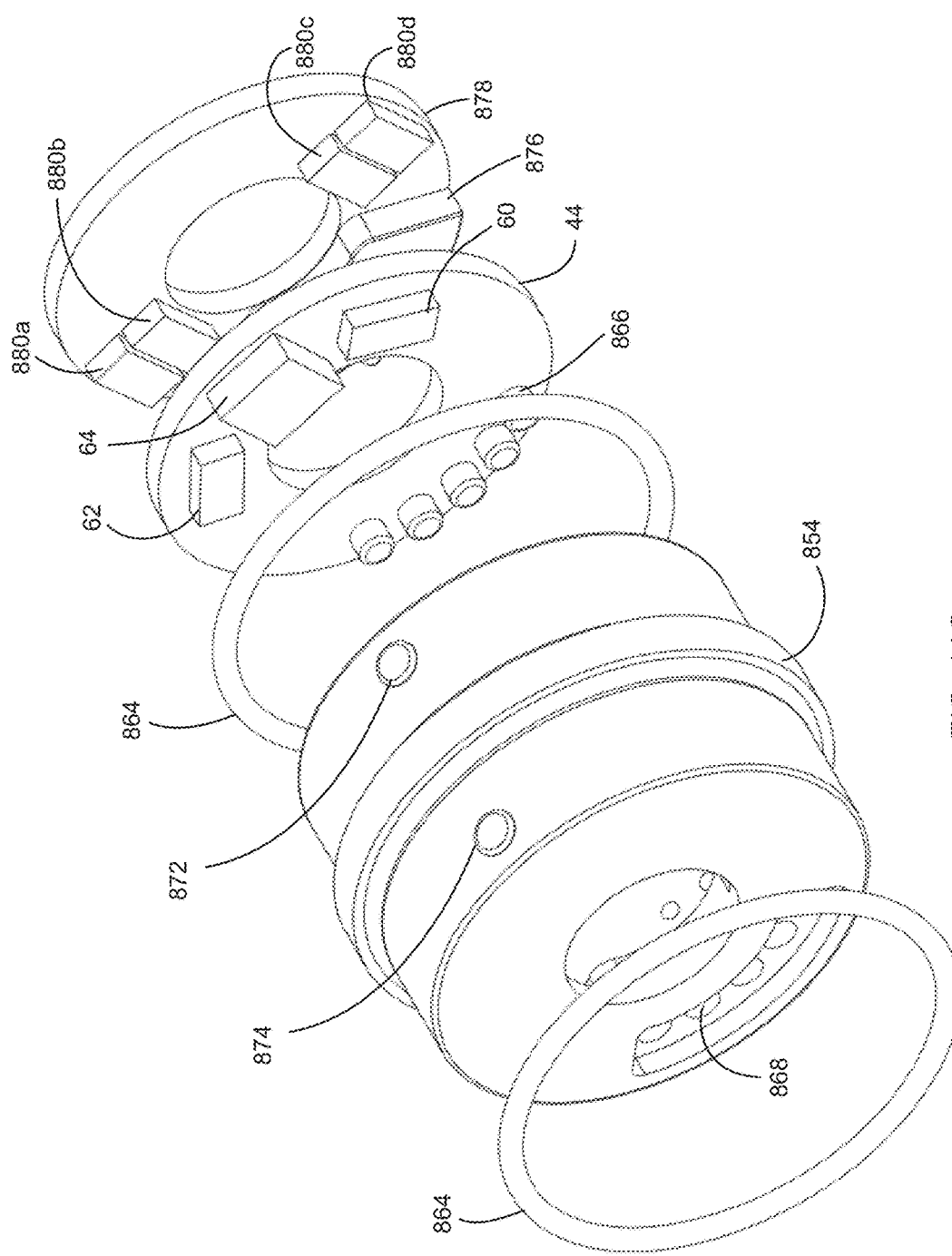
FIGS. 11C to 11E are views of the various components of the ingestible medical device shown in FIG. 11A.

Referring now to FIG. 11C, illustrated therein is an exploded view of the midsection joint 854. As illustrated in FIG. 11C, the environmental sensor PCB 878 includes the auxiliary sensor connector 876 and multiple environmental sensors 880*a* to 880*d*. The environmental sensors 880*a* to 880*d* can be at least one of a pressure sensor, a temperature sensor, a pH sensor, and the like.

Referring back to FIG. 11B, in some embodiments, each chamber 18 in the storage sub-unit 852' includes a chamber seal 882. The chamber seal 882 can be manufactured from silicone polymer or rubber. The chamber seal 882 acts as an access point to the corresponding chamber 18 that it is covering. As will be described in more detail below, after the ingestible medical device 10 is retrieved, the second portion 14 can be detached from the first portion 12 so that the chambers 18 can be accessed through the corresponding chamber seals 882 using needle engagement elements located on the base station. By being detachable, the second portion 14 can undergo sterilization processes that would otherwise damage the electronic components in the first portion 12.

The coupling seals 864 seal the ingestible medical device 10 so that the first portion 12 and the second portion 14 are protected from the external environment. As well, the coupling seals 864 enable the ingestible medical device 10 to be easily closed (sealed) and opened (unsealed) so that the first portion 12 and the second portion 14 can be conveniently accessed.

Figure 10C:
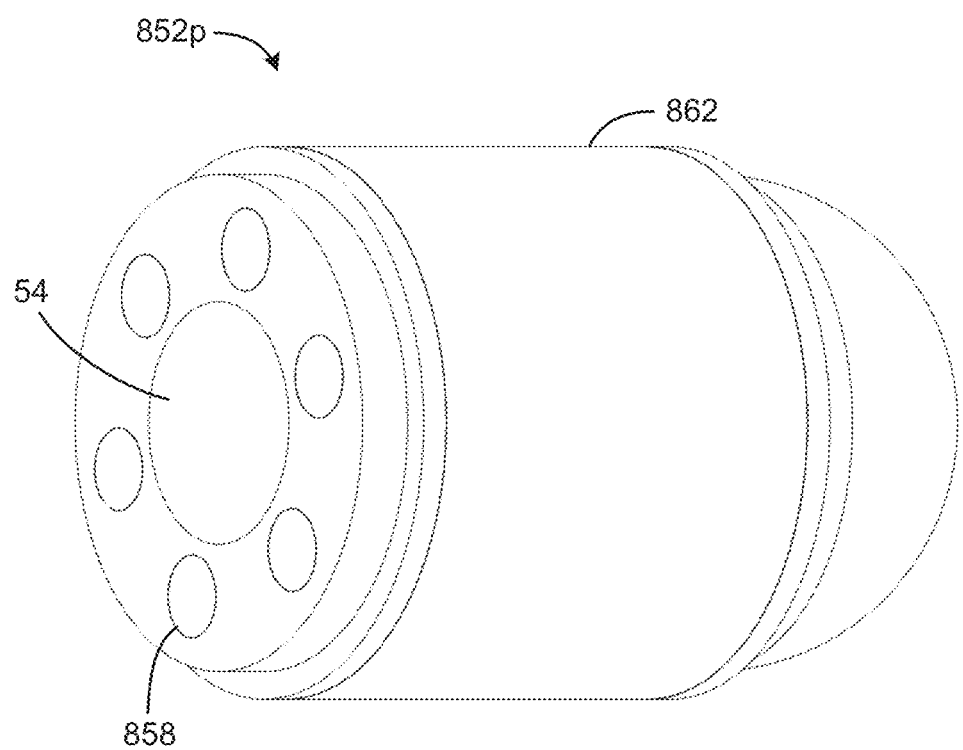
Figure 11D:
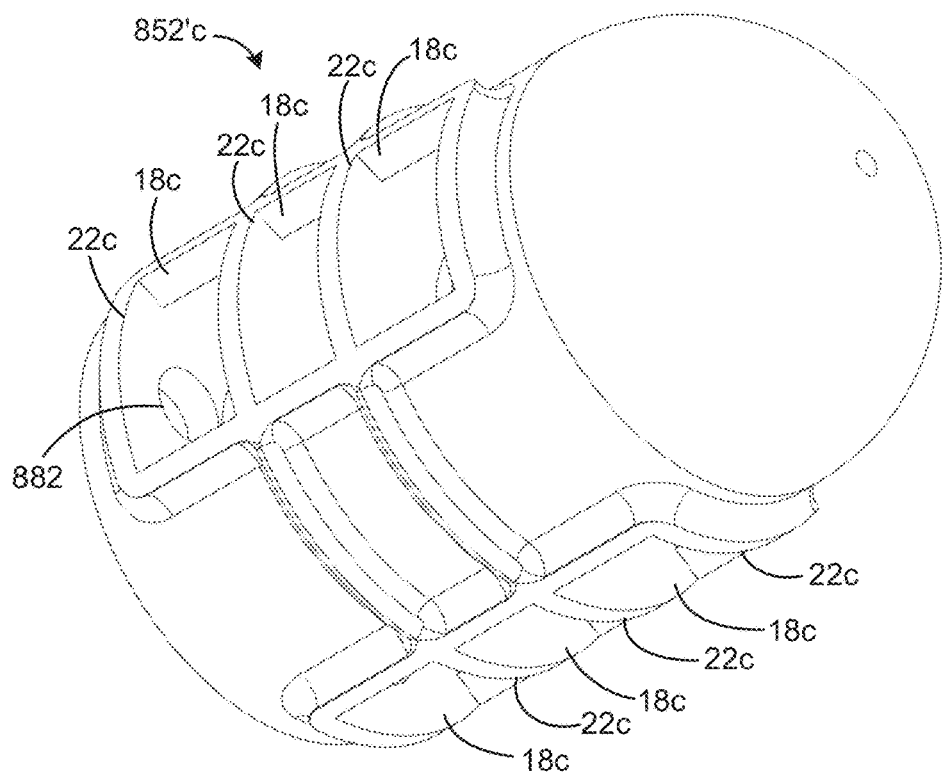
Figure 11E:
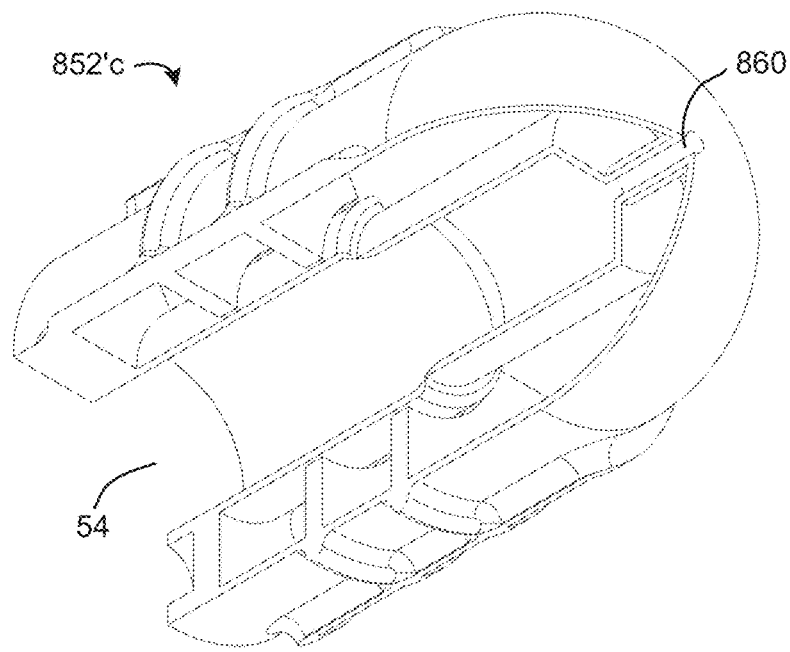

In some embodiments, the storage sub-unit 852' can be detachable and disposable. Generally, the storage sub-units 852' are highly configurable and so, it is possible to have a variety of different storage sub-units 852' which can be advantageously dedicated for conducting different tasks (e.g., conducting a biopsy of a tissue inside the body) and storing different assays. For example, chambers 18 in a storage sub-unit 852' can be divided into multiple compartments, as illustrated in FIGS. 11D and 11E. In another example, the storage sub-unit 852' can include a polymer band around its circumferential wall, as illustrated in FIG. 10C, that reacts chemically with its outer environment to gradually expose access to the chambers 18.

Referring now to FIGS. 11D and 11E, illustrated therein are different views of a storage sub-unit 852'*c*. As illustrated in FIG. 11D, each chamber 18 in the storage sub-unit 852'*c* is divided into multiple compartments 18*c* and each compartment 18*c* has a corresponding compartment opening 22*c*. This storage sub-unit 852'*c* enables the ingestible medical device 850' to carry multiple reagents for release into the body and to carry the multiple reagents separately. A chamber seal 882 is also provided in each chamber 18 for accessing the chambers 18. A partial view of the storage sub-unit 852'*c* is provided in FIG. 11E. As described above, in this example embodiment, the storage sub-unit 852'*c* is rotated by the motor 42 and thus, the motor compartment 54 inside the storage sub-unit 852'*c* ends with the truncated aperture 860 for coupling with the motor 42.

Figure 12B:
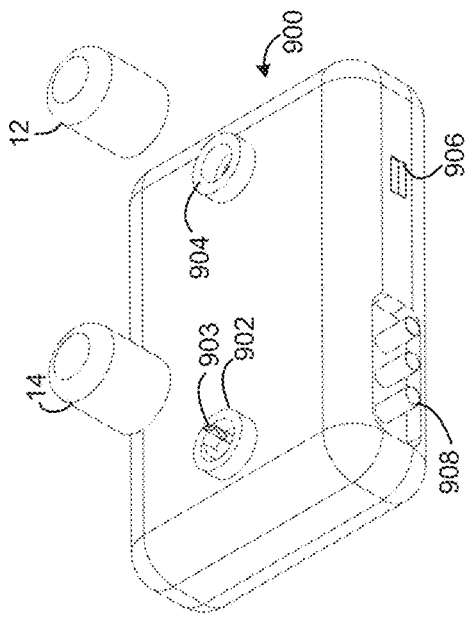
FIGS. 12A to 12C are views of an example embodiment of a base station.
Figure 12D:
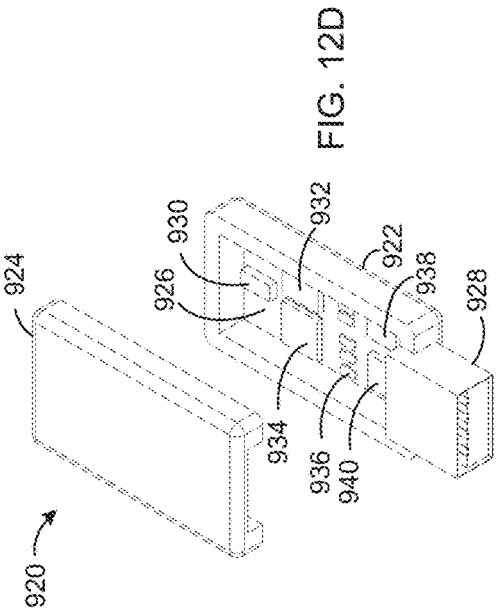
FIG. 12D is an example embodiment of a communications device that can be used with the base station.
Figure 12A:
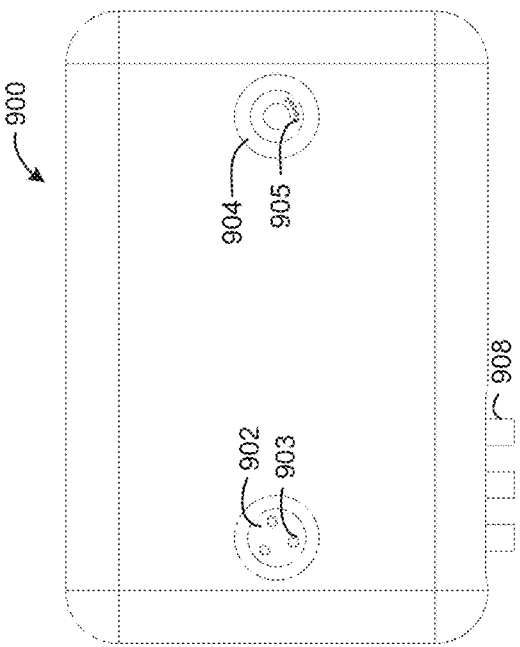
Figure 12C:
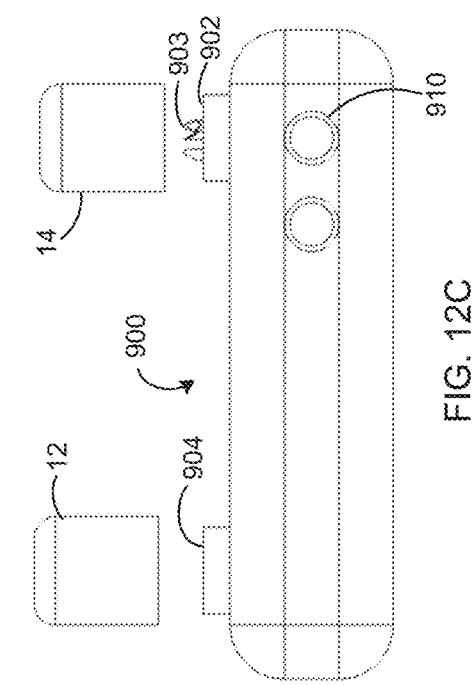

After the ingestible medical device 850' completes its operation and is retrieved, the first portion 12 and the second portion 14 can be detached from each other for post-processing on a base station 900, as illustrated in FIGS. 12A to 12C. The base station 900 may also be used for preparing the ingestible medical device 850' for operation, such as by programming and/or charging the ingestible medical device 850' or loading reagents into the chambers 18.

Figure 20A:
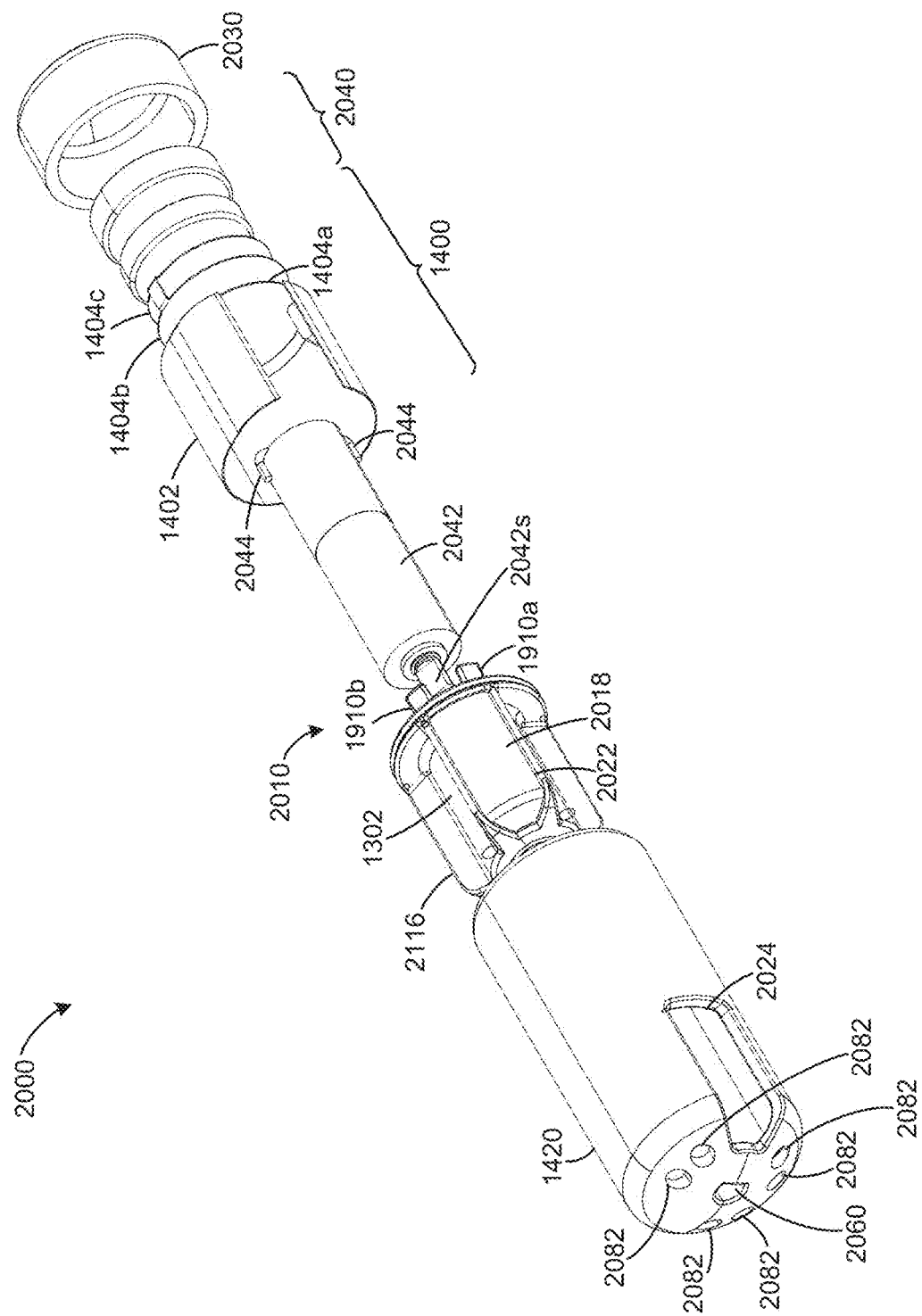
FIG. 20A is an exploded view of another example embodiment of an ingestible medical device.

Referring now to FIG. 20A, illustrated therein is an exploded view of an ingestible medical device 2000. Similar to the ingestible medical devices 850 and 850' described above with reference to FIGS. 10A to 100 and 11A to 11E, respectively, the ingestible medical device 2000 also includes a rotating storage sub-unit 2016 and a stationary chamber enclosure 1420. The ingestible medical device 2000 includes the flexible PCB 1400 as described above with reference to FIGS. 14A to 14F and therefore, the stationary chamber enclosure 1420 encloses both the rotating storage sub-unit 2016 and the flexible PCB 1400. It will be understood that the other embodiments described herein could similarly use the flexible PCB 1400 where possible.

As illustrated in FIG. 20A, some components in the ingestible medical device 2000 are analogous to the components used in the ingestible medical device 10 described above. These analogous components are referred to by similar reference numerals for consistency and will not generally be described. In comparison with the ingestible medical device 10, several components in the ingestible medical device 2000 are physically different. For example, the storage sub-unit 16, the chamber enclosure 20, the main PCB 32, the power supply 40 and the end enclosure 30 of the ingestible medical device 10 are now replaced by the storage sub-unit 2016, the chamber enclosure 1420, the flexible PCB 1400, the power supply 2040 and the end enclosure 2030 in the ingestible medical device 2000. Also, several components, such as the secondary PCB 44 and the encoding magnet arrangement 46 in the ingestible medical device 10 are not used in the ingestible medical device 2000. Instead, the optical encoder 1406 and the protrusion members 1910 on the storage sub-unit 2016 (see FIGS. 14A and 20J, for example) replace the secondary PCB 44 and the encoding magnet arrangement 46.

Figure 20C:
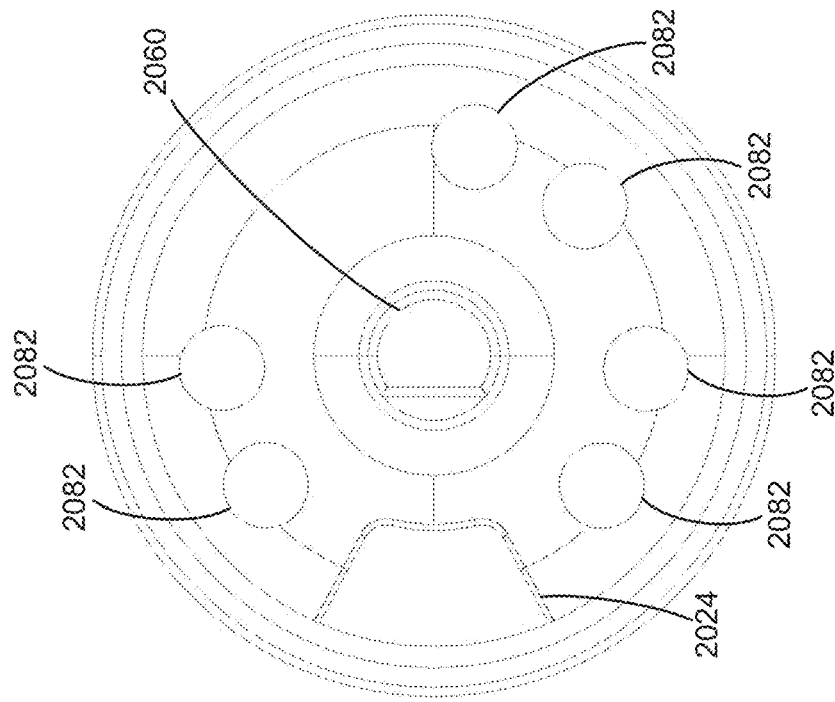
FIGS. 20B to 20L are views of the various components of the ingestible medical device shown in FIG. 20A.
Figure 20B:
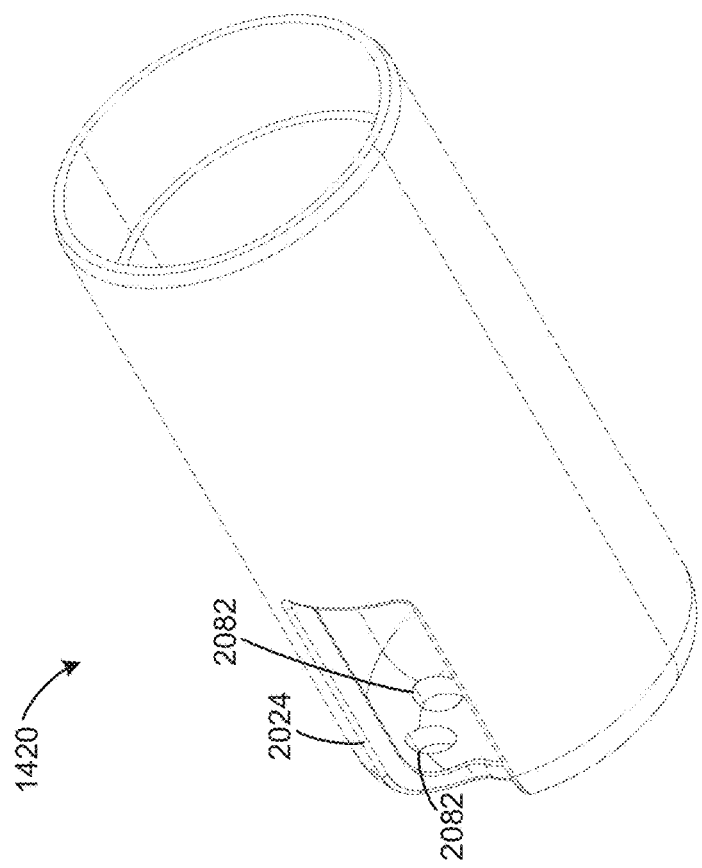

Referring simultaneously to FIGS. 20B and 20C, illustrated therein are different views of the chamber enclosure 1420. Generally, each chamber 2018 in the storage sub-unit 2016 includes at least one chamber aperture 2082 and the chamber aperture 2082 may be sealed. In some embodiments, each chamber 2018 may be associated with two chamber apertures 2082. The chamber aperture 2082 can be sealed with a silicone polymer or rubber material. The chamber aperture 2082 acts as an access point to the corresponding chamber 2018. As will be described in more detail below, after the ingestible medical device 2000 is retrieved, the chambers 2018 of the ingestible medical device 2000 can be accessed through the corresponding chamber apertures 2082 using needle engagement elements such as those located on the base station 900.

Also, as illustrated in FIGS. 20A and 20C, the chamber enclosure 1420 includes a truncated aperture 2060 for receiving and engaging the shaft 2042s of the motor 2042.

Referring simultaneously to FIGS. 20D to 20H, illustrated therein are partial views of an example embodiment of the storage sub-unit 2016 of the ingestible medical device 2000.

Similar to the storage sub-unit 16 of the ingestible medical device 10, the storage sub-unit 2016 includes one or more chambers 2018 each with a corresponding chamber opening 2022. The storage sub-unit 2016 also includes non-recessed areas 1302 that separate at least two chambers 2018. The non-recessed areas 1302 may be solid arcs formed with the material used for fabricating the storage sub-unit 2016. For example, the non-recessed areas 1302 may be formed using materials with a low hardness level as measured using the durometer or any other soft biocompatible materials described above. In a specific example, the non-recessed areas 1302 may be formed using silicone polymer.

In order to maximize a volume of sample collection, the arc spanned by each of the non-recessed areas 1302 may be smaller than an arc spanned by the chambers 2018. Also, some chambers 2018 may not be separated by a non-recessed area 1302. For example, similar to the ingestible medical device 1310 of FIGS. 13A to 13E, the storage sub-unit 2016 of the ingestible medical device 2000 can include three chambers 2018 and two non-recessed areas 1302. Two adjacent chambers 2018 are not separated by a non-recessed area 1302. Therefore, when the storage sub-unit 2016 is in operation, the storage sub-unit 2016 may rotate in the bidirectional motion as described with reference to FIGS. 13A to 13E.

Also, unlike the storage sub-unit 16, dividers between each of the chambers 2018 in the storage sub-unit 2016 extend to the chamber enclosure 1420. The chamber enclosure 1420, therefore, can act as a seal or a wall for enclosing any sample or substance that is collected into or stored in the chambers 2018. Since the dividers engage the chamber enclosure 1420, the dividers can also clear away any substance or sample that may remain on an inner wall of the chamber enclosure 1420. The dividers can therefore assist in avoiding cross-contamination between the samples being collected or substances being released.

As described above, the chamber enclosure 1420 may be fabricated using a CNC machined polycarbonate material and the storage sub-unit 2016 can be fabricated using a silicone polymer material, such as a UV light-curable medical-grade silicone polymer. By using a soft or rigid material, such as silicone polymer or any of the other materials described above, the storage sub-unit 2016 can be fabricated with conventional manufacturing techniques, such as injection molding or with a 3D-printed mold. In comparison with the CNC machined polycarbonate material of the chamber enclosure 1420, the silicone polymer material is softer. The interaction between the dividers of the storage sub-unit 2016 and the chamber enclosure 1420 can therefore have a sealing effect due to the soft-to-rigid contact due to the materials used for these two elements.

Figure 20F:
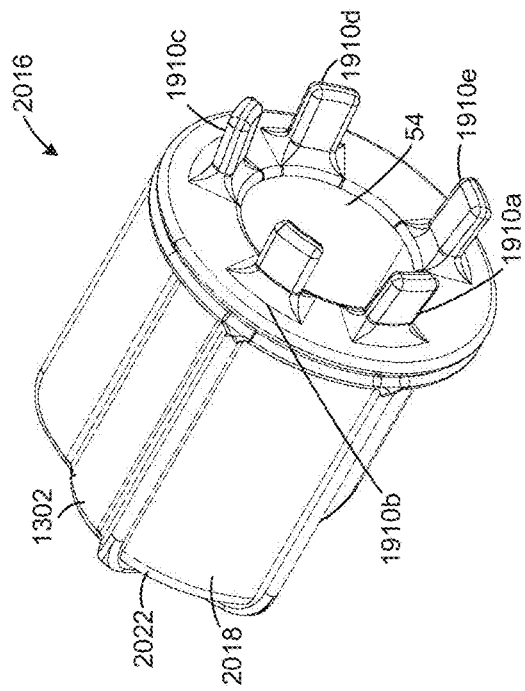

Unlike the storage sub-unit 16, the storage sub-unit 2016 includes one or more protrusion members 1910. As shown in FIG. 20F, the storage sub-unit 2016 includes protrusion members 1910a to 1910e. As described above with reference to FIG. 19, the protrusion members 1910, or other optical markers, can be used in combination with the optical encoder 1406 for determining a position of the storage sub-unit 2016 in relation to an access port 2024.

Figure 20G:
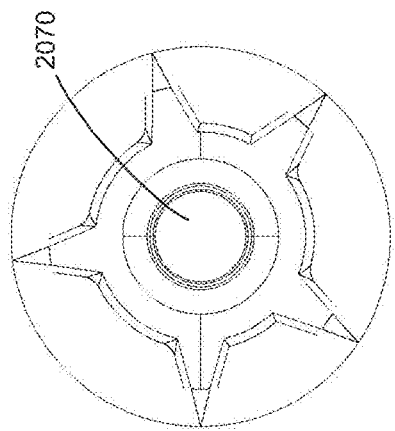
Figure 20D:
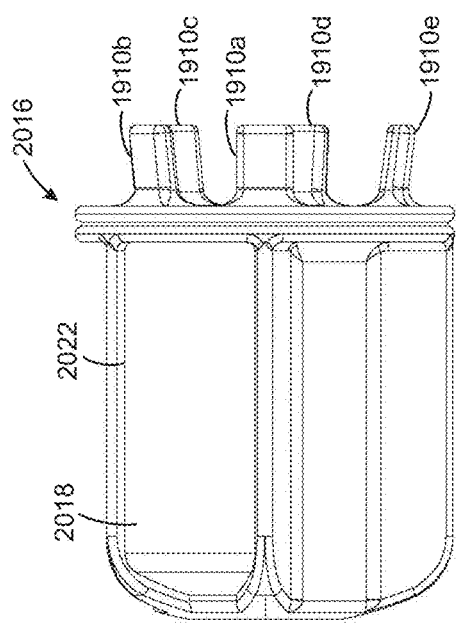
Figure 20E:
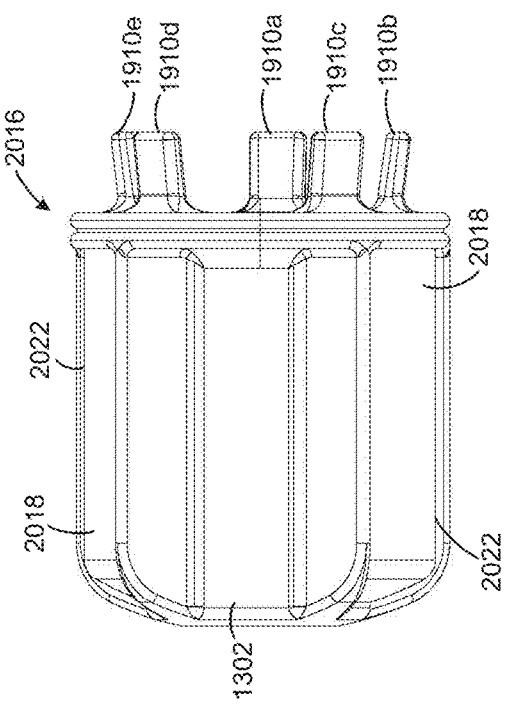

Also, as shown in FIGS. 20A and 20G, the motor compartment 54 in the storage sub-unit 2016 ends with an aperture 2070 for allowing the motor shaft 2042s to engage the truncated aperture 2060 of the chamber enclosure 1420. Accordingly, the motor 2042 is coupled to the storage sub-unit 2016 for rotating the storage sub-unit 2016 such that the body of the motor 2042 and the storage sub-unit 2016 both rotate while the motor shaft 2042s is held in place in the truncated aperture 2060. The motor 2042 can be coupled to the storage sub-unit 2016 by pressure fit and/or chemical bonding or adhesion.

Figure 20J:
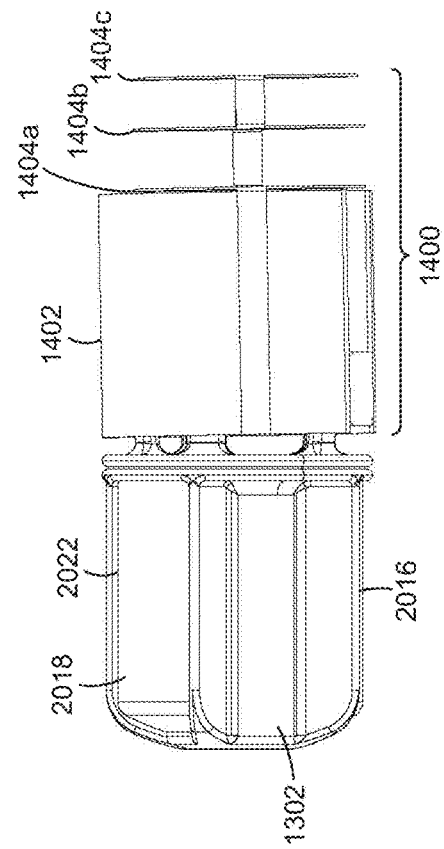
Figure 20H:
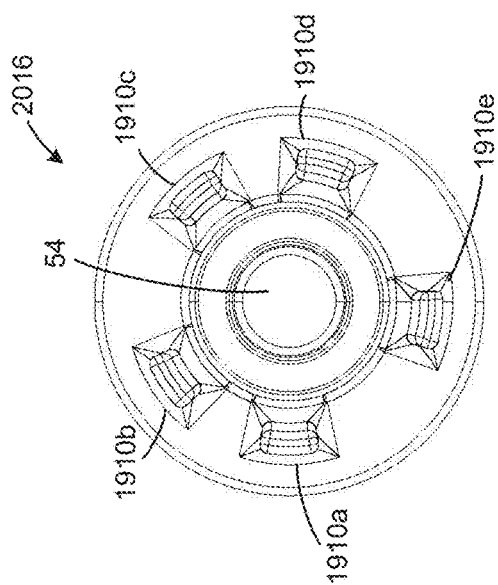
Figure 20I:
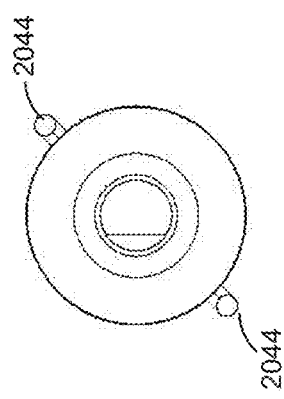

Referring now to FIG. 20I, illustrated therein is a front view of the motor 2042. At an outer circumference of the motor 2042, there are at least two leads 2044. The leads 2044 may be separated from each other by a short circumferential distance in order to minimize any stress that may be caused on the flexible PCB 1400 as the motor 42 rotates. Power is supplied to the motor 2042 via the leads 2044. The leads 2044 connect to the motor driver 214 via contacts located on the main PCB 32, such as the motor contact terminal 1412 located on the flexible PCB 1400 (FIG. 14C).

Figure 20K:
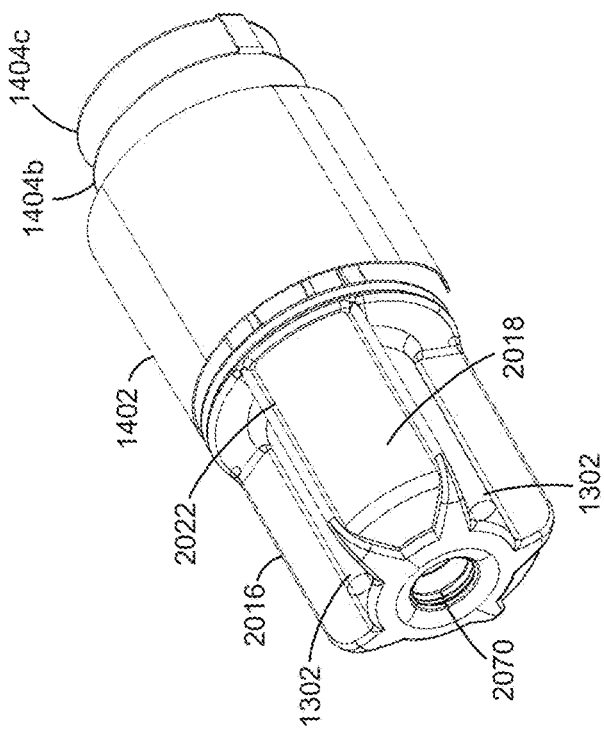
Figure 20L:
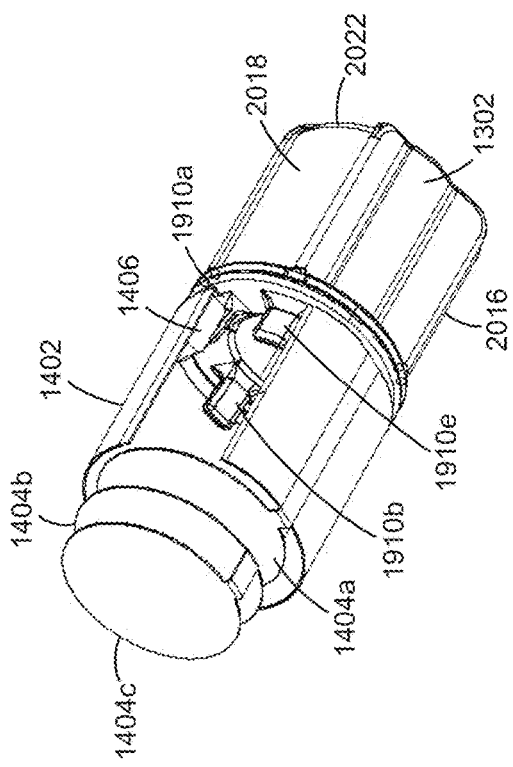

Referring now to FIGS. 20J to 20L, illustrated therein are different views of the storage sub-unit 2016 with the flexible PCB 1400. As generally illustrated in FIG. 20J, when the flexible PCB 1400 is conformed to fit within the chamber enclosure 1420, the longitudinal axis of the flexible PCB 1400 is generally aligned with a rotational axis of the storage sub-unit 2016. The optical encoder 1406, as illustrated in FIG. 20L, is located on a region of the main PCB segment 1402 so that the optical encoder 1406 can more effectively sense the protrusion members 1910 as the protrusion members 1910 rotate with the storage sub-unit 2016.

Referring again to FIG. 20A, the power supply 2040 can include multiple battery cell groups, such as the first battery cell group and the second battery cell group. The battery cell groups can be coin cell batteries, such as silver oxide battery cells. Also, since the flexible PCB 1400 is used in the ingestible medical device 2000 and can be configured differently than the main PCB 32, the end enclosure 2030 of the ingestible medical device 2000 can be shorter than the end closure 30 of ingestible medical devices 10, 850 and 850'.

Referring simultaneously to FIGS. 12A to 12C, illustrated therein are different views of an example embodiment of the base station 900. In this case, the base station 900 illustrated in FIGS. 12A to 12C can be used with the ingestible medical device 850'. The base station 900 includes a chamber engagement dock 902, a programming and charging dock 904, a Universal Serial Bus (USB) connection port 906, fluid connection ports 908, and one or more base station LEDs 910.

As illustrated in FIG. 12A, the chamber engagement dock 902 includes at least one removable needle engagement element 903, which in this example is a prong. The number of needle engagement elements 903 provided in the chamber engagement dock 902 typically corresponds with the number of chambers 18 in the storage sub-unit 852'. For example, as illustrated in FIG. 12B, three needle engagement elements 903 are provided since the storage sub-unit 852' in this example embodiment has three chambers 18. It will be understood that a different number of needle engagement elements 903 can similarly be provided on the chamber engagement dock 902 depending on the configuration of the chamber apertures 2082 or chamber seals 882 provided on the ingestible medical device.

The needle engagement elements 903 are used for extracting substances from the storage sub-unit 852', 2016 and/or loading substances into the storage sub-unit 852', 2016 through the chamber seals 882 or the chamber apertures 2082, respectively. For example, for retrieving collected samples from the ingestible medical device 850', the storage sub-unit 852' is loaded onto the chamber engagement dock 902 by engaging the needle engagement elements 903 with the corresponding chamber seals 882. The content of each chamber 18 is then aspirated and extracted from the storage sub-unit 852'. Similarly, for retrieving collected samples from the ingestible medical device 2000, the ingestible medical device 2000 can be loaded onto the chamber engagement dock 902 by engaging the needle engagement elements 903 with the corresponding chamber apertures 2082. The content of each chamber 2018 is then aspirated and extracted from the storage sub-unit 2016.

Alternatively, instead of using the needle engagement elements 903, samples may be retrieved from each of the ingestible medical devices 10, 850, 850' and 2000 by sequentially exposing each of the chambers 18. The collected samples may then be washed out of the chambers 18.

Referring simultaneously to FIGS. 12A and 12B, the programming and charging dock 904 includes five electrical contacts 905 for connecting to the programming and charging connector 866 on the secondary PCB 44. It will be understood that the number of electrical contacts 905 used in this embodiment is merely an example and that a different number of electrical contacts 905 can be used. In some embodiments, firmware can be programmed onto the ingestible medical device 850' through the electrical contacts 905 on the programming and charging dock 904. In some embodiments, the power supply 40 can be charged through the electrical contacts 905 on the programming and charging dock 904.

In this case, while a programming and charging dock 904 is shown it should be understood that in alternative embodiments, there can be a charging dock for charging the ingestible medical device 850' and a separate programming component for programming the ingestible device. The programming component can be a radio transceiver or an infrared transceiver.

The fluid connection ports 908 are connections for pumping in reagents and substances or extracting samples from at least one of the chambers 18 of the ingestible medical device 850'. In this example, the fluid connection ports are tube connections. The fluid connection ports 908 are coupled to the needle engagement elements 903.

The LEDs 910 can be used for indicating the status of the docks 902 and 904 on the base station 900 as well as certain commands that are received from an external computer. For example, the LEDs 910 can be used to indicate Emergency Stop and Override commands coming from the computer when extracting or inserting substances into the ingestible medical device 850'.

In some embodiments, a communications device 920, as illustrated in FIG. 12D, can be used for programming the ingestible medical device 850'. The communications device 920 provides transceiver functionality to act as a communication interface for the ingestible medical device 850' so that information can be sent to and received from an external computing device for data logging and/or use with a graphical user interface. The communications device 920 may be a programmable USB dongle device (e.g. programmable USB key). The communications device 920 includes a component casing 922 and an enclosure casing 924. The enclosure casing 924 couples to the component casing 922 for protecting the electrical components located on the component casing 922. The component casing 922 includes a programmable device PCB 926 and a programmable device USB connection port 928 for communicating with the external computing device, such as a personal computer, and for receiving power. The programmable device PCB 926 includes a microcontroller 934, a transceiver 932, an antenna 930, multiple LEDs 936, and other electrical components 938 and 940 for RF and USB communication. The LEDs 936 can be used for indicating a status of the communications device 920, such as when the communications device 920 is receiving programming instructions.

In alternative embodiments, the communications device 920 is not used and rather the external computing device, such as a desktop computer, a laptop, a tablet and the like, are connected to the USB connection port 906a of the base station 900 through a USB cable. In this case, a graphical user interface on the external computer is used to work with the ingestible medical device. The term "work" implies the functions of communication, programming, as well as control of the various chambers to fill the chambers with reagents or substances for distribution as well as remove samples from the chambers. Other functions may also be performed.

In some embodiments, an administrator of the ingestible medical devices 10, 850, 850' and 2000 may configure the operation of the ingestible medical devices 10, 850, 850' and 2000 via the graphical user interface. For example, the administrator may set a rate of sample acquisition, the type of data to be collected and/or a mode of operation (e.g., to collect samples or to release substances). In some further embodiments, the graphical user interface may display information corresponding to an operational status of the ingestible medical devices 10, 850, 850' and 2000. The operational status can include a status of a peripheral component on the ingestible medical devices 10, 850, 850' and 2000 and/or a status of the power supply 40.

With the embodiments of the ingestible medical device 850 and 850' having an internally rotating configuration there is no concern with drag created by viscous fluids on the exterior of the device and the friction between rotating parts is controlled. Also, the ingestible medical device 850' has the advantage of simple and complete seals from the external environment. The ingestible medical devices 850 and 850' can also be more easily reused and recharged as these devices can be sealed and opened and sealed over and over again. Also, with the ingestible medical device 850, contacts can be used for recharging and data transfer. The methods described herein are applicable to both configurations of the ingestible medical devices described herein that use external rotation of the chamber enclosure or internal rotations of the storage sub-unit. Both of these configurations may encounter particulate matter. The escape and wiggle routines are also advantageous as they may be used to meet regulatory approval for non-obstruction and no damage to a patient or subject's GI tract during use.

In general, with the various embodiments described herein, the first portion 12 that includes various electrical components such as control electronics, a power supply, and communication components can be encapsulated such that it is simply cleaned after use so that it can be reused. The second portion 14 that includes components for sample collection and/or substance delivery as well as environmental monitoring can be separately processed from the first portion 12. In fact, there may be various different types of second portions that are usable with the first portion 12 which allows the ingestible medical device to have a modular design. For example, there can be different second portions 14 that are used depending on the particular application of the ingestible medical device and these different second portions can have a different number of chambers, differently sized chambers as well as embodiments in which at least one chambers has a reagent or at least some of the chambers are configured for in-vivo analysis.

At least some of the elements of the various embodiments of the ingestible medical device described herein that are implemented via software may be written in a high-level procedural language such as object oriented programming or a scripting language. Accordingly, the program code may be written in C, C++ or any other suitable programming language and may comprise modules or classes, as is known to those skilled in object oriented programming. Alternatively, or in addition, at least some of the elements of the embodiments of the ingestible medical device described herein that are implemented via software may be written in assembly language, machine language or firmware as needed. In either case, the program code can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Furthermore, at least some of the methods described herein are capable of being distributed in a computer program product comprising a computer readable medium that bears computer usable instructions for one or more processors. The medium may be provided in various forms such as, but not limited to, one or more diskettes, compact disks, tapes, chips, USB keys, external hard drives, wire-line transmissions, satellite transmissions, Internet transmissions or downloads, magnetic and electronic storage media, digital and analog signals, and the like. The computer useable instructions may also be in various forms, including compiled and non-compiled code.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims.

The invention claimed is:

1. An ingestible medical device, comprising:
a housing comprising a chamber which comprises a chamber opening configured to collect a sample and/or distribute a substance; and
a member covering the housing, the member comprising a solid region and a member opening;
an encoder sub-unit configured to generate a position signal based on a distance between the chamber opening and the member opening;
a motor configured to provide relative movement between the housing and the member; and
a microcontroller coupled to the motor and the encoder sub-unit so that, based on the position signal, the microcontroller causes the motor to generate relative movement between the housing and the member based on the position signal.

2. The ingestible medical device of claim 1, wherein the member is rotatable, and the housing is stationary.

3. The ingestible medical device of claim 2, wherein the encoder sub-unit comprises:
an encoder coupled to the member; and
a sensor coupled to the housing and configured to generate the position signal.

4. The ingestible medical device of claim 2, wherein the encoder sub-unit comprises:
a marker supported by the member; and
a sensor coupled to the housing, the sensor being configured to generate the position signal.

5. The ingestible medical device of claim 1, wherein the chamber comprises multiple compartments.

6. The ingestible medical device of claim 1, wherein the housing further comprises a second chamber.

7. The ingestible medical device of claim 6, wherein the chambers are separated from each other.

8. The ingestible medical device of claim 1, wherein the ingestible medical device further comprises a communication sub-unit that is configured to receive operating instructions and operating parameters from an external base station.

9. The ingestible medical device of claim 1, further comprising an environmental sensor printed circuit board with an auxiliary sensor connector and at least one environmental sensor.

10. The ingestible medical device of claim 9, further comprising a main microcontroller configured to initialize operation of the ingestible medical device based on sensor data received from the at least one environmental sensor.

11. The ingestible medical device of claim 10, wherein the main microcontroller is further configured to:
receive the sensor data from the at least one environmental sensor;
store and update a stored operational count value; and
determine, using the received sensor data, if one or more operational thresholds is exceeded in order to determine a location of the ingestible medical device in use, the one or more operational thresholds comprise at least one of a minimum temperature change threshold, a minimum transit time threshold, a minimum operational count threshold and a periodicity threshold.

12. The ingestible medical device of claim 11, wherein the main microcontroller is further configured to:
determine if the sensor data received from the environmental sensor exceeds the minimum temperature change threshold; and
reset the operational count if the sensor data received from the environmental sensor exceeds the minimum temperature change threshold.

13. The ingestible medical device of claim 11, wherein the main microcontroller is further configured to:
   determine if a transit time exceeds the minimum transit time threshold; and
   increase the operational count if the transit time exceeds the minimum transit time threshold, but otherwise continue to receive the sensor data.

14. The ingestible medical device of claim 11, wherein the main microcontroller is further configured to continue to receive the sensor data if the operational count value is determined to not exceed a minimum operational count threshold.

15. The ingestible medical device of claim 1, wherein the ingestible medical device comprises a modular design with a first portion comprising electrical components and a second portion comprising components for at least one of sample collection and substance delivery, or a first portion for providing an enclosure for the ingestible medical device and a second portion comprising electrical components and components for at least one of sample collection and substance delivery.

16. The ingestible medical device of claim 15, wherein the electrical components are located on a flexible printed circuit board, and the flexible printed circuit board is conformed to fit within the member and align with a rotational axis of a rotatable element of the ingestible medical device.

17. A system, comprising:
   an ingestible medical device according to claim 1; and
   a base station comprising a programming component for programming the ingestible medical device.

18. The system of claim 17, wherein the programming component comprises a transmitter configured to transmit at least one member selected from the group consisting of programming instructions and operating parameters to the ingestible medical device.

19. The system of claim 18, wherein the transmitter is an infrared transmitter.

20. The ingestible medical device of claim 1, further comprising a sensor usable to determine a location of the ingestible device within the GI tract of a subject.

21. The ingestible medical device of claim 1, wherein the sensor comprises at least one member selected from the group consisting of a pH sensor, a temperature sensor, an optical sensor, an impedance sensor and a capacitance sensor.

22. The ingestible medical device of claim 1, further comprising at least two different sensors selected from the group consisting of a pH sensor, a temperature sensor, an optical sensor, an impedance sensor and a capacitance sensor.

23. The ingestible medical device of claim 1, further comprising an optical sensor usable to determine a location of the ingestible device within the GI tract of a subject.

24. The ingestible medical device of claim 23, wherein the optical sensor is configured to provide information indicating whether the ingestible device is in the stomach of the subject, the pyloric sphincter of the subject or the small intestine of the subject.

25. The ingestible medical device of claim 1, further comprising a sensor comprising an LED emitter and receiver.

26. The ingestible medical device of claim 25, wherein the sensor is configured to provide information indicating whether the ingestible device is in the stomach of the subject, the pyloric sphincter of the subject or the small intestine of the subject.

27. The ingestible medical device of claim 1, further comprising a sensor comprising an LED emitter and a receiver.

28. The ingestible medical device of claim 27, wherein the sensor is configured to provide information indicating whether the ingestible device is in the stomach of the subject, the pyloric sphincter of the subject or the small intestine of the subject.

29. The ingestible medical device of claim 1, further comprising a sensor comprising a plurality of LED emitters and receivers evenly distributed around the ingestible medical device.

30. The ingestible medical device of claim 29, wherein the sensor is configured to provide information indicating whether the ingestible device is in the stomach of the subject, the pyloric sphincter of the subject or the small intestine of the subject.

31. The ingestible medical device of claim 29, further comprising a sensor configured to provide information indicating whether the ingestible device is in the stomach of the subject, the pyloric sphincter of the subject or the small intestine of the subject.

32. The ingestible medical device of claim 1, further comprising a plurality of LED emitters and receivers evenly distributed around the ingestible medical device,
   wherein the plurality of LED emitters and receivers are usable to determine a location of the ingestible medical device within the GI tract of a subject.

33. The ingestible device of claim 1, further comprising:
   a processor;
   memory; and
   sensors within the chamber,
   wherein the ingestible device is configured to collect data from the sample via the sensors so that the data is storable in the memory.

34. The ingestible device of claim 1, further comprising:
   a processor;
   memory; and
   sensors configured to collect data from a GI tract of a subject so that the data is storable in the memory.

35. The ingestible device of claim 1, wherein the ingestible device is removable from the subject so that the sample is analyzable after the ingestible device is removed from the subject.

36. The ingestible device of claim 1, wherein the housing and comprises a further chamber,
   wherein:
      the chamber is configured to contain a first substance;
      the further chamber is configured to contain a second substance; and
      the ingestible device is configured to reduce cross-contamination between the chambers.

37. The ingestible device of claim 36, wherein the ingestible device comprises a hydrophilic material configured to reduce cross-contamination between the chambers.

38. The ingestible device of claim 37, wherein the hydrophilic material is present in the chamber.

39. The ingestible device of claim 36, wherein the ingestible device comprises a hydrophobic material configured to reduce cross-contamination between the chambers.

40. The ingestible device of claim 39, wherein the hydrophobic material is present in the chamber.

41. The ingestible device of claim 36, further comprising:
   a hydrophilic material present in the chamber; and
   a hydrophobic material present in the further chamber, wherein the hydrophilic and hydrophobic materials are configured to reduce cross-contamination between the chambers.

42. The ingestible device of claim 36, further comprising a divider between the chambers, wherein the divider is configured to reduce cross-contamination between the chambers.

43. The ingestible device of claim 36, wherein the ingestible device is configured to reduce cross-contamination between the chambers.

44. The ingestible medical device of claim 1, wherein the encoder sub-unit comprises:
   an encoder; and
   a sensor configured to generate the position signal based on a position of the encoder.

45. The ingestible medical device of claim 44, wherein the encoder is supported by the member, and the sensor is supported by the housing.

46. The ingestible medical device of claim 45, wherein the encoder comprises a magnet, and the sensor comprises a magnetic sensor.

47. The ingestible medical device of claim 44, wherein the encoder is supported by the housing, and the sensor is supported by the member.

48. The ingestible medical device of claim 47, wherein the encoder comprises a magnet, and the sensor comprises a magnetic sensor.

49. The ingestible medical device of claim 44, wherein the encoder comprises a magnet, and the sensor comprises a magnetic sensor.

50. The ingestible medical device of claim 1, wherein the encoder sub-unit comprises:
   a marker; and
   a sensor configured to generate the position signal based on a position of the marker.

51. The ingestible device of claim 50, wherein the marker is supported by the member, and the sensor is supported by the housing.

52. The ingestible device of claim 51, wherein the marker comprises an optical marker, and the sensor comprises an optical sensor.

53. The ingestible device of claim 50, wherein the marker is supported by the housing, and the sensor is supported by the member.

54. The ingestible device of claim 53, wherein the marker comprises an optical marker, and the sensor comprises an optical sensor.

55. The ingestible device of claim 50, wherein the marker comprises an optical marker, and the sensor comprises an optical sensor.

* * * * *

UNITED STATES PATENT AND TRADEMARK OFFICE
CERTIFICATE OF CORRECTION

PATENT NO. : 10,172,598 B2
APPLICATION NO. : 14/460893
DATED : January 8, 2019
INVENTOR(S) : Yaw Amoako-Tuffour et al.

Page 1 of 1

It is certified that error appears in the above-identified patent and that said Letters Patent is hereby corrected as shown below:

In the Claims

Column 56, Line 48, Claim 36, delete "and comprises" and insert -- comprises --.

Signed and Sealed this
Nineteenth Day of February, 2019

Andrei Iancu
*Director of the United States Patent and Trademark Office*

UNITED STATES PATENT AND TRADEMARK OFFICE
CERTIFICATE OF CORRECTION

| | |
|---|---|
| PATENT NO. | : 10,172,598 B2 |
| APPLICATION NO. | : 14/460893 |
| DATED | : January 8, 2019 |
| INVENTOR(S) | : Amoako-Tuffour et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1112 days.

Signed and Sealed this
Sixth Day of December, 2022

Katherine Kelly Vidal
*Director of the United States Patent and Trademark Office*